US005712274A

United States Patent [19]

Sueoka et al.

[11] Patent Number: 5,712,274

[45] Date of Patent: Jan. 27, 1998

[54] THIENOTRIAZOLODIAZEPINE COMPOUNDS AND THEIR PHARMACEUTICAL USE

[75] Inventors: Hiroyuki Sueoka; Shuji Ehara; Haruhito Kobayashi; Takeshi Arichi, all of Fukuoka; Hirotsugu Komatsu, Saitama, all of Japan

[73] Assignee: Yoshitomi Pharmaceutical Industries, Ltd., Osaka, Japan

[21] Appl. No.: 413,444

[22] Filed: Mar. 30, 1995

Related U.S. Application Data

[63] Continuation-in-part of Ser. No. 403,726, filed as PCT/JP93/01329, Sep. 16, 1993, abandoned.

[51] Int. Cl.[6] .......................... A61K 31/55; C07D 243/06

[52] U.S. Cl. .......................... 514/219; 514/220; 540/555; 540/560

[58] Field of Search .................................... 540/855, 560; 514/219, 220

[56] References Cited

U.S. PATENT DOCUMENTS

| | | | |
|---|---|---|---|
| 4,017,620 | 4/1977 | Kuwada et al. | 424/248.51 |
| 4,992,437 | 2/1991 | Naka et al. | 514/220 |

FOREIGN PATENT DOCUMENTS

| | | |
|---|---|---|
| 0 638 560 | 2/1995 | European Pat. Off. . |
| 94 05673 | 3/1994 | WIPO . |

OTHER PUBLICATIONS

Tahara et al. Chemical Abstract 120:270466 (1993) with STN Printout.

Weber et al, Chem. Abstract 113:191406 (1990) with STN Printout.

Derwent Abstract of JP-A-3-223290 (1990).

Derwent Abstract of JP-A-005756 corresponding to JP-B-57-45755 (1974).

Derwent Abstract of DE-3936828 corresponding to JP-A-243691 (1989).

Derwent Abstract of DE-4006471 corresponding to JP-A-2-275883 (1990).

Derwent Abstract of EP-320,992 corresponding to JP-A-1-197484 (1989).

Derwent Abstrct of JP-A-297479 (1993).

Derwent Abstract of WO89/05812 (1989).

Derwent Abstract of WO93/12117 (1993).

Derwent Abstract of WO94/22872 (1994).

Derwent Abstract of WO93/07129 (1993).

*Primary Examiner*—John M. Ford

*Assistant Examiner*—Brenda Coleman

*Attorney, Agent, or Firm*—Wenderoth, Lind & Ponack

[57] ABSTRACT

Thienotriazolodiazepine compounds of the formula (1)

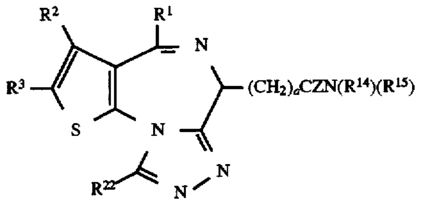

(1)

wherein each symbol is as defined in the specification, pharmaceutically acceptable salts thereof, and pharmaceutical use thereof. The compounds of the present invention are useful as preventive and therapeutic drugs for inflammatory diseases and allergic diseases, in which cell adhesion is involved.

12 Claims, No Drawings

THIENOTRIAZOLODIAZEPINE COMPOUNDS AND THEIR PHARMACEUTICAL USE

This application is a continuation-in-part of application Ser. No. 08/403,726 filed Mar. 17, 1995 now abandoned, which is a U.S. national stage application of PCT/JP93/01329 filed Sep. 16, 1993.

BACKGROUND OF THE INVENTION

1. Field of the Invention

The present invention relates to novel thienotriazolodiazepine compounds having superior inhibitory effect on cell adhesion, pharmaceutically acceptable salts thereof, and pharmaceutical use thereof.

2. Description of Related Art

In various inflammations and allergic diseases, infiltration of so-called inflammatory cells (leukocytes in a wide sense) such as polymorphonuclear leukocytes, macrophages and lymphocytes is deeply concerned with the symptoms of the diseases. Although the adhesion of leukocytes to vascular endothelial cells has been considered the first step of infiltration of leukocytes from earlier days, its mechanism has been uncertain. The recent progress in molecular biology has enabled identification of the molecules concerned with the adhesion, and their functional significance, that is, the phenomenon of leukocyte adhesion via certain adhesion molecules expressed on vascular endothelial cells, and adhesion molecules on leukocytes that specifically bind with said molecules, followed by infiltration of leukocytes into inflammatory cells, has been clarified. While the combinations (shown below) of molecules involved in leukocyte adhesion to vascular endothelial cells are considered to be particularly important, the degree of the involvement of respective adhesion molecules in various inflammations and allergic diseases is not entirely clear.

| vascular endothelial cell side | leukocyte side |
|---|---|
| intercellular adhesion molecule-1 (ICAM-1) | leukocyte function-associated antigen-1 (LFA-1) |
| | Mac-1 |
| ELAM-1 | carbohydrate ligand (sialyl $Le^x$, sialyl $Le^a$) |
| P-selectin | Sulfatide |
| Glycam-1 | L-selectin |
| Sulfatide | |
| vascular cell adhesion molecule-1 (VCAM-1) | very late activated antigen-4 (VLA-4) |

Of these adhesion molecules, ICAM-1 and LFA-1 are known to be deeply involved in not only cell infiltration, but also in adhesion of lymphocytes together and their activation. For example, LFA-1 on T lymphocytes binds with ICAM-1 on macrophages to activate T lymphocytes. Accordingly, a substance which inhibits the binding between ICAM-1 and LFA-1 is expected to have immunosuppressive action in a wide sense.

In connection with diseases, promoted expressions of ICAM-1 and ELAM-1 in inflammatory sites in autoimmune diseases such as inflammatory skin diseases (e.g. contact dermatitis, light eruptions caused by high photosensitivity, and so on) and rheumatoid arthritis have been reported, and involvement of VCAM-1, ICAM-1 and Mac-1 in asthma has been suggested. It has also been reported that cell adhesion via ICAM-1 plays an important role in graft rejection after the organ transplantation, and that adhesion molecules are concerned with tumor metastasis. Recent studies have increasingly revealed that various cell adhesion molecules are deeply concerned with the onset and progress of ulcerative colitis, Crohn's disease, nephritis and so on. Moreover, cell adhesion molecules are known to be deeply involved in the formation and evolution of atherosclerosis, ischemia-reperfusion injury, septic shock and so on.

Using test animals, it has also been reported that expression of adhesion molecules has been promoted in various inflammatory models (e.g. delayed type hypersensitivity model and autoimmune nephritic model) and that anti-ICAM-1 antibody and anti-LFA-1 antibody inhibit inflammatory responses (e.g. adjuvant-induced arthritis, collagen-induced arthritis and so on). Moreover, the role of adhesion molecules in activation of eosinophils in monkey asthmatic models has been clarified. Furthermore, the effect of anti-LFA-1 antibody and anti-ICAM-1 antibody in mouse heterotopic heart transplantation models has been reported, suggesting the importance of adhesion molecules in the graft rejection, as in the case of humans.

Various steroidal agents, non-steroidal antiinflammatory agents, and inhibitors for release of inflammation- and/or allergy-related mediators have been used as therapeutic agents for various inflammatory diseases and allergic diseases. Of these pharmaceutical agents, steroidal agents often cause severe side-effects and other pharmaceutical agents fail to achieve sufficient therapeutic effects.

Under these circumstances, a compound having cell adhesion inhibitory action is expected to be a superior antiinflammatory drug or anti-allergic drug. For example, Proc. Natl. Acad. Sci. U.S.A., vol. 88, pp 355–359 (1991) teaches that N-(fluorenyl-9-methoxycarbonyl)amino acids suppress reactions in various animal inflammatory models by inhibiting adhesion of leukocytes, and an extract from American Federation for Clinical Research Annual Meeting, May 6, 1991, teaches that the same series of compounds inhibit leukocyte adhesion to vascular endothelial cells, by inhibition of adhesion molecule (CD18) expression on leukocytes. As discussed, compounds having inhibitory effect on cell adhesion are expected to be usable as pharmaceutical agents for the prevention and treatment of the above-mentioned diseases and disorders.

International Publication No. WO 89/05812 and Japanese Patent Unexamined Publication No. 223290/1991 disclose thienodiazepine compounds having CCK antagonistic action or gastrin antagonistic action; International Publication Nos. WO 93/12177 and WO 94/22872 disclose thienotriazolodiazepine compounds having inhibitory effect on cell adhesion; International Publication No. WO 93/07129 discloses a thienotriazolodiazepine compound usable as a therapeutic agent for osteoporosis; Japanese Patent Unexamined Publication No. 275883/1990 discloses a thienotriazolodiazepine compound having platelet activating factor (PAF) inhibitory activity and applicable to ulcerative colitis.

However, the compounds described in various known literatures including the above-mentioned are not sufficient to afford satisfactory inhibitory effect on cell adhesion, and the development of an antiinflammatory and anti-allergic drug having stronger cell adhesion inhibitory effect is desired.

SUMMARY OF THE INVENTION

With the aim of searching a cell adhesion inhibitor, in particular, a compound strongly inhibiting adhesion of leukocytes to vascular endothelial cells (leukocyte adhesion inhibitor), the present inventors have established an assay system for cell adhesion by the use of human umbilical vein-derived endothelial cells (HUVEC) and human leukemia cell line and conducted intensive studies. As a result, they have found that a novel thienotriazolodiazepine compound has a strong inhibitory effect on cell adhesion, which resulted in the completion of the invention.

That is, the present invention relates to thienotriazolodiazepine compounds of the formula (1)

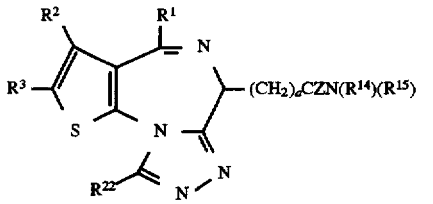

(1)

wherein

- $R^1$ is an alkyl, an alkenyl, an alkynyl, an optionally substituted cycloalkyl, an optionally substituted cycloalkylalkyl, an optionally substituted aryl or an optionally substituted heterocyclic ring;
- $R^2$ is a hydrogen, a halogen, an alkyl or an optionally substituted aralkyl;
- $R^3$ is a hydrogen, a halogen, an alkyl, an alkenyl, an alkynyl or an optionally substituted aralkyl; or
- $R^2$ and $R^3$ may combinedly form an optionally substituted 5 to 7-membered ring, or an optionally substituted 5 to 7-membered heterocyclic ring together with a hetero atom;
- a is an integer of 1 to 6;
- $R^{14}$ and $R^{15}$ are the same or different and each is a hydrogen, a hydroxy, an alkoxy, an aralkyloxy, an aryloxy, an optionally substituted cycloalkyl, an alkyl, a substituted alkyl, an alkenyl, a substituted alkenyl, an alkynyl, a substituted alkynyl, an optionally substituted aryl, an optionally substituted heterocyclic ring, an optionally substituted aralkyl, an optionally substituted heteroarylalkyl or a group of the formula;

$$-N(R^{19})(R^{20})$$

wherein $R^{19}$ and $R^{20}$ are the same or different and each is a hydrogen, an alkyl, an alkenyl, an alkynyl or an optionally substituted aralkyl, or $R^{19}$ and $R^{20}$ may combinedly form an optionally substituted 5 to 7-membered heterocyclic ring together with the adjacent nitrogen atom; or

- $R^{14}$ and $R^{15}$ may combinedly form an optionally substituted 5 to 7-membered heterocyclic ring together with the adjacent nitrogen atom;
- Z is an oxygen atom or a sulfur atom; and
- $R^{22}$ is a hydrogen, a halogen, an alkoxy, an alkyl, an alkenyl, an alkynyl, an optionally substituted cycloalkyl, an optionally substituted cycloalkylalkyl, an optionally substituted aryl, an optionally substituted heterocyclic ring, an optionally substituted aralkyl, an optionally substituted heteroarylalkyl or a group of the formula;

$$-(CH_2)_bCOOR^{23}$$

wherein $R^{23}$ is a hydrogen, an alkyl, an alkenyl or an optionally substituted aralkyl and b is an integer of 1–6, and pharmaceutically acceptable salts thereof.

The present invention also relates to a pharmaceutical composition comprising a therapeutically effective amount of a compound of the formula (1) and a pharmaceutically acceptable additive, and to a method for treating inflammatory diseases and allergic diseases caused by cell adhesion, comprising administering a compound of the formula (1).

The present invention also provides thienotriazolodiazepine compounds of the formula (12)

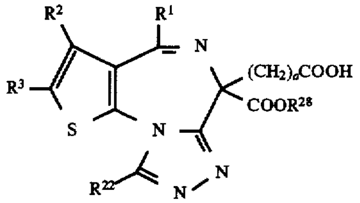

(12)

wherein $R^{28}$ is an alkyl having 1 to 4 carbon atoms such as methyl and ethyl and other symbols are as defined above; and compounds of the formula (11)

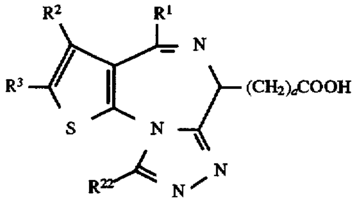

(11)

wherein each symbol is as defined above, and pharmaceutically acceptable salts thereof, which are useful as intermediates for the compounds of the formula (1).

DETAILED DESCRIPTION OF THE INVENTION

In the present specification, each symbol means the following.

Alkyl means a linear or branched alkyl having 1 to 20 carbon atoms, and is exemplified by methyl, ethyl, propyl, isopropyl, butyl, isobutyl, tert-butyl, pentyl, isopentyl, tert-pentyl, hexyl, octyl, 2-ethylhexyl, 2,2-diethyloctyl, 1,1,3,3-tetramethylbutyl, nonyl, decyl, dodecyl, tetradecyl, octadecyl and icocyl. The alkyl preferably has 1 to 6, particularly preferably 1 to 4, carbon atoms.

Alkenyl has 2 to 20 carbon atoms and includes, for example, vinyl, allyl, 1-propenyl, 2-methyl-1-propenyl, 3-methyl-1-butenyl, 2,3-dimethyl-1-butenyl, 3,4,5-trimethyl-1-butenyl, 3-butenyl, 3-hexenyl, 5-dodecenyl, 6-ethyl-3-decenyl, 11,11-dimethyl-7-tetradecenyl, 14-octadecenyl and 8-icocenyl. The alkenyl preferably has 2 to 8, particularly preferably 2 to 4, carbon atoms.

Alkynyl has 2 to 20 carbon atoms and includes, for example, 1-propynyl, 3-methyl-1-butynyl, 1,4-dimethyl-1-hexynyl, ethynyl, propargyl, 3-hexynyl, 3,4-diethyl-1-octynyl, 5-dodecynyl, 6-ethyl-3-decynyl, 11,11-dimethyl-7-tetradecynyl, 14-octadecynyl and 8-icocynyl. The alkynyl preferably has 2 to 8, particularly preferably 2 to 4, carbon atoms.

Optionally substituted cycloalkyl is that where the cycloalkyl moiety has 3 to 10 carbon atoms, and is exemplified by cyclopropyl, 2,3-dimethylcyclopropyl, cyclobutyl, 3-methylcyclobutyl, cyclopentyl, 3,4-dimethylcyclopentyl, cyclohexyl, 4-aminocyclohexyl, 4-methylcyclohexyl, 4-tert-butylcyclohexyl, cycloheptyl, cyclooctyl, norbornyl, 1-adamantyl, bicyclo[3.3.0]octan-1-yl and bicyclo[3.3.1]nonan-9-yl, with preference given to cyclopropyl, cyclopentyl, cyclohexyl, 4-tert-butylcyclohexyl, cycloheptyl and 4-aminocyclohexyl.

Optionally substituted cycloalkylalkyl is that where the cycloalkyl moiety has 3 to 10 carbon atoms and the alkyl moiety has 1 to 6, preferably 1 to 3, carbon atoms, and is exemplified by cyclopropylmethyl, 2,3-dimethylcyclopropyl, cyclobutylmethyl, 3-methylcyclobutylmethyl, cyclopentylmethyl, 3,4-dimethylcyclopentylmethyl, cyclohexylmethyl, 4-methylcyclohexylmethyl, cycloheptylmethyl, cyclooctylmethyl, 2-cyclohexylethyl, 3-cyclohexylpropyl, norbornylmethyl, 1-adamantylmethyl, bicyclo[3.3.0]octan-1-ylmethyl and bicyclo[3.3.1]nonan-9-ylmethyl.

Optionally substituted aryl is exemplified by phenyl, 1-naphthyl and 2-naphthyl, with preference given to phenyl. The aryl may have, on the aromatic ring, 1 to 3 substituents selected from halogen, alkyl, substituted alkyl, alkoxy having 1 to 6 carbon atoms, hydroxy, mercapto, alkylthio, arylthio, aralkylthio, optionally substituted sulfamoyl, optionally substituted amino, optionally substituted heterocyclic ring, nitro, cyano, carboxy, sulfo, alkoxycarbonyl, optionally substituted azo and optionally substituted carbamoyl.

With regard to optionally substituted heterocyclic ring, the hetero atom constituting the ring is nitrogen, oxygen, sulfur or the like, and the ring is an aromatic heterocyclic ring or partially saturated heterocyclic ring or completely saturated heterocyclic ring or fused heterocyclic-ring optionally having 1 to 3 substituents selected from halogen, optionally substituted alkyl, alkoxy having 1 to 6 carbon atoms, hydroxy, mercapto, optionally substituted amino, optionally substituted aminosulfonyl, optionally substituted heterocyclic ring, nitro, cyano, carboxy, alkoxycarbonyl having 1 to 6 carbon atoms, optionally substituted carbamoyl and optionally substituted azo. Examples thereof include pyridyl (e.g. 2-pyridyl, 3-pyridyl and 4-pyridyl), quinolyl (e.g. 2-quinolyl, 3-quinolyl and 4-quinolyl), imidazolyl (e.g. 2-imidazolyl, 4-imidazolyl and 5-imidazolyl), pyrrolyl (e.g. 2-pyrrolyl and 3-pyrrolyl), isoquinolyl (e.g. 1-isoquinolyl, 3-isoquinolyl and 4-isoquinolyl), triazolyl (e.g. 1-triazolyl and 2-triazolyl), 1-pyrazolyl, 2-oxo-1,2,3,4-tetrahydroquinolin-5, 6 or 7-yl, 2-oxoindolin-5 or 6-yl, 2-oxopyrolidine-3 or 4-yl, 2-oxopiperidin-4-yl, 1-benzylpiperidin-4-yl, pyridazinyl (e.g. 3-pyridazinyl and 4-pyridazinyl), pyrimidinyl (e.g. 2-pyrimidinyl, 4-pyrimidinyl and 5-pyrimidinyl), pyrazinyl, indolyl (e.g. 2-indolyl, 3-indolyl, 4-indolyl and 5-indolyl), thienyl (e.g. 2-thienyl and 3-thienyl), furyl (e.g. 2-furyl and 3-furyl), benzofuranyl (e.g. 2-benzofuranyl and 3-benzofuranyl), 1H-benzimidazol-2-yl, 2-thiazolyl, 2-benzothiazolyl, 4-methylpiperazin-1-yl, 1-piperazinyl and 1-perhydropyridazinyl, with particular preference given to pyridyl, imidazolyl, pyridazinyl, pyrimidinyl and pyrazinyl.

Halogen means chlorine, fluorine, bromine and iodine.

Optionally substituted aralkyl is that where the alkyl moiety has 1 to 6, preferably 1 to 4, carbon atoms, and may have, on the aromatic ring, 1 to 3 substituents selected from halogen, optionally substituted alkyl, alkoxy having 1 to 6 carbon atoms, hydroxy, mercapto, alkylthio, arylthio, aralkylthio, optionally substituted sulfamoyl, optionally substituted amino, optionally substituted heterocyclic ring, nitro, cyano, carboxy, alkoxycarbonyl, optionally substituted azo and optionally substituted carbamoyl. Examples thereof include benzyl, 1-phenylethyl, 1-naphthylmethyl, 3-aminobenzyl, 3-dimethylaminobenzyl, 3-carbamoylbenzyl and 3-sulfamoylbenzyl, with particular preference given to benzyl, 3-aminobenzyl and 3-carbamoylbenzyl.

Optionally substituted heteroarylalkyl may have, on its ring, 1 to 3 substituents selected from halogen, optionally substituted alkyl, alkoxy having 1 to 6 carbon atoms, hydroxy, mercapto, alkylthio, arylthio, aralkylthio, optionally substituted sulfamoyl, optionally substituted amino, optionally substituted heterocyclic ring, nitro, cyano, carboxy, alkoxycarbonyl, optionally substituted azo and optionally substituted carbamoyl. The alkyl moiety thereof has 1 to 4, preferably 1 or 2, carbon atoms, and the hetero atom constituting the ring is nitrogen, oxygen or sulfur. Examples thereof include pyridyl(2-pyridyl, 3-pyridyl or 4-pyridyl)-methyl, quinolyl(2-quinolyl or 3-quinolyl) methyl, indolyl(2-indolyl or 3-indolyl)methyl, thienyl(2-thienyl or 3-thienyl)-methyl, furyl(2-furyl or 3-furyl)methyl, benzofuranyl(2-benzofuranyl or 3-benzofuranyl)methyl, 1H-benzimidazol-2-ylmethyl, 2-benzothiazolylmethyl, 2-(2-thienyl)ethyl and 2-(2-furyl)ethyl.

Optionally substituted 5 to 7-membered ring formed by $R^2$ and $R^3$ in combination and optionally substituted 5 to 7-membered heterocyclic ring formed by $R^2$ and $R^3$ together with hetero atom are exemplified by cyclopentene, cyclopentadiene, cyclohexene, cyclohexadiene, cycloheptene, cycloheptadiene, cycloheptatriene, benzene, dihydropyran, dihydrothiapyran and tetrahydropyridine, and examples of the substituent include alkyl such as methyl and ethyl, benzyl and aralkyl such as 2-phenylethyl.

Alkoxy is that where the alkyl moiety has 1 to 6 carbon atoms and may be linear, branched or cyclic. The alkoxy may have 1 to 3 substituents selected from alkoxy having 1 to 6 carbon atoms, halogen, hydroxy, sulfo, mercapto, alkylthio, arylthio, aralkylthio, amidino, guanidino, optionally substituted amino, optionally substituted heterocyclic ring, nitro, cyano, carboxy, alkoxycarbonyl, oxo, optionally substituted sulfamoyl and optionally substituted carbamoyl. Examples of the alkoxy include methoxy, ethoxy, propoxy, isopropoxy, butoxy, tert-butoxy, hexyloxy and cyclohexyloxy.

Aralkyloxy may have, on its aromatic ring, 1 to 3 substituents selected from halogen, optionally substituted alkyl, alkoxy having 1 to 6 carbon atoms, hydroxy, mercapto, alkylthio, arylthio, aralkylthio, optionally substituted sulfamoyl, optionally substituted amino, optionally substituted heterocyclic ring, nitro, cyano, carboxy, alkoxycarbonyl, optionally substituted azo and optionally substituted carbamoyl. Its alkyl moiety has 1 to 4, preferably 1 or 2, carbon atoms, and the aralkyloxy is exemplified by benzyloxy, 2-phenylethyloxy, 1-naphthyloxy and 4-aminobenzyloxy, with particular preference given to benzyloxy and 2-phenetyloxy.

Aryloxy may have, on its aromatic ring, 1 to 3 substituents selected from halogen, optionally substituted alkyl, alkoxy having 1 to 6 carbon atoms, hydroxy, mercapto, alkylthio, arylthio, aralkylthio, optionally substituted sulfamoyl, optionally substituted amino, optionally substituted heterocyclic ring, nitro, cyano, carboxy, alkoxycarbonyl, optionally substituted azo and optionally substituted carbamoyl. Examples of the aryloxy include phenoxy, 1-naphthoxy, 4-aminophenoxy and 4-carbamoylphenoxy, with particular preference given to phenoxy.

Examples of 5 to 7-membered heterocyclic ring formed by $R^{14}$ and $R^{15}$, or $R^{19}$ and $R^{20}$, together with the adjacent nitrogen atom, include morpholine, thiomorpholine, pyrrolidine, piperidine, piperazine, pyrazole and 1H-1,2,4-triazole. The heterocyclic ring may have substituent(s) such as hydroxy, hydroxyalkyl (e.g. hydroxymethyl, 2-hydroxyethyl and 3-hydroxypropyl), amino, alkyl having 1 to 4 carbon atoms (e.g. methyl, ethyl, propyl, isopropyl, butyl, isobutyl and tert-butyl) and benzyl. Examples of the heterocyclic ring include 4-hydroxypiperidin-1-yl, 4-benzylpiperidin-1-yl, 4-methylpiperazin-1-yl, 4-(2-hydroxyethyl)piperazin-1-yl, 3-aminopyrazol-1-yl and 3-amino-1H-1,2,4-triazol-1-yl.

Alkyl having substituent is that where the alkyl moiety has 1 to 6 carbon atoms and may be linear or branched. The alkyl has 1 to 3 substituents selected from alkoxy having 1 to 6 carbon atoms, halogen, hydroxy, sulfo, mercapto, alkylthio, arylthio, aralkylthio, amidino, guanidino, optionally substituted amino, optionally substituted heterocyclic ring, nitro, cyano, carboxy, alkoxycarbonyl, oxo, optionally substituted sulfamoyl, optionally substituted azo and optionally substituted carbamoyl. Examples of the alkyl include hydroxymethyl, 2-hydroxymethyl, 2-aminoethyl, 2-dimethylaminoethyl, 2-(methanesulfonylamino)ethyl, 2-methoxyethyl, 2-amidinoethyl and 2-ethoxycarbonylethyl.

Alkenyl having substituent is that where the alkenyl moiety has 2 to 6 carbon atoms and may be linear or branched. The alkenyl has 1 to 3 substituents selected from alkoxy having 1 to 6 carbon atoms, halogen, hydroxy, sulfo, mercapto, alkylthio, arylthio, aralkylthio, amidino, guanidino, optionally substituted amino, optionally substituted heterocyclic ring, nitro, cyano, carboxy, alkoxycarbonyl, oxo, optionally substituted sulfamoyl and optionally substituted carbamoyl.

Alkynyl having substituent is that where the alkynyl moiety has 2 to 6 carbon atoms and may be linear or branched. The alkynyl has 1 to 3 substituents selected from alkoxy having 1 to 6 carbon atoms, halogen, hydroxy, sulfo, mercapto, alkylthio, arylthio, aralkylthio, amidino, guanidino, optionally substituted amino, optionally substituted heterocyclic ring, nitro, cyano, carboxy, alkoxycarbonyl, oxo, optionally substituted sulfamoyl and optionally substituted carbamoyl.

With regard to the above-mentioned substituents, each means the following.

Halogen as a substituent means chlorine, fluorine, bromine or iodine.

Alkyl having 1 to 6 carbon atoms is exemplified by methyl, ethyl, propyl, isopropyl, butyl, isobutyl, tert-butyl, pentyl, isopentyl, tert-pentyl and hexyl.

Alkoxy having 1 to 6 carbon atoms is exemplified by methoxy, ethoxy, propoxy, isopropoxy, butoxy, isobutoxy, tert-butoxy, pentyloxy, isopentyloxy, tert-pentyloxy and hexyloxy.

Optionally substituted azo may have, on its nitrogen atom, 1 or 2 substituents selected from alkyl having 1 to 6 carbon atoms, cycloalkyl, optionally substituted aryl, aralkyl, heteroaryl and heteroarylalkyl, and is exemplified by phenylazo, 4-(sulfophenyl)azo, (3-carboxy-4-hydroxyphenyl)azo and (N-(2-pyridylsulfamoyl)phenyl) azo.

Optionally substituted sulfamoyl may have, on its nitrogen atom, 1 or 2 substituents selected from alkyl having 1 to 6 carbon atoms, cycloalkyl, aryl, aralkyl, heteroaryl and heteroarylalkyl, and is exemplified by sulfamoyl, methylsulfamoyl, dimethylsulfamoyl and phenylsulfamoyl.

Alkylthio is that where the alkyl moiety has 1 to 6 carbon atoms, and is exemplified by methylthio, ethylthio and isopropylthio.

Arylthio may have, on its aromatic ring, 1 to 3 substituents selected from halogen, optionally substituted alkyl, alkoxy having 1 to 6 carbon atoms, hydroxy, mercapto, alkylthio, arylthio, aralkylthio, optionally substituted sulfamoyl, optionally substituted amino, optionally substituted heterocyclic ring, nitro, cyano, carboxy, alkoxycarbonyl, optionally substituted azo and optionally substituted carbamoyl, and is exemplified by phenylthio and naphthylthio.

Optionally substituted amino may have, on its nitrogen atom, 1 or 2 substituents selected from alkyl having 1 to 6 carbon atoms, aryl, arylalkyl, heteroaryl, heteroarylalkyl, carboxy, alkylcarbonyl having 1 to 6 carbon atoms, alkoxycarbonyl having 1 to 6 carbon atoms, arylcarbonyl, aryloxycarbonyl, aralkylcarbonyl, aralkyloxycarbonyl, heteroarylcarbonyl, heteroarylalkylcarbonyl and sulfonyl, and is exemplified by amino, methylamino, dimethylamino, anilino, benzylamino, pyridylamino, pyridylmethylamino, acetylamino, benzoylamino, ethoxycarbonylamino, mecylamino and a group of the formula

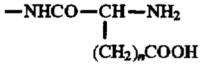

wherein n is an integer of 1 to 4.

Aralkylthio is that where the alkyl moiety has 1 to 6 carbon atoms and may have, on its aromatic ring, 1 to 3 substituents selected from halogen, optionally substituted alkyl, alkoxy having 1 to 6 carbon atoms, hydroxy, mercapto, alkylthio, arylthio, aralkylthio, optionally substituted sulfamoyl, optionally substituted amino, optionally substituted heterocyclic ring, nitro, cyano, carboxy, alkoxycarbonyl, optionally substituted azo and optionally substituted carbamoyl. The aralkylthio is exemplified by benzylthio, 2-phenylethylthio, 1-phenylethylthio and 1-naphthylmethylthio.

Alkylcarbonyl having 1 to 6 carbon atoms is exemplified by acetyl, ethylcarbonyl, propylcarbonyl, isopropylcarbonyl, butylcarbonyl, isobutylcarbonyl, tert-butylcarbonyl, pentylcarbonyl, isopentylcarbonyl, tert-pentylcarbonyl and hexylcarbonyl.

Alkoxycarbonyl having 1 to 6 carbon atoms is exemplified by methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl, tert-pentyloxycarbonyl and hexyloxycarbonyl.

Examples of arylcarbonyl include benzoyl, 1-naphthylcarbonyl and 2-naphthylcarbonyl. The arylcarbonyl may have, on its aromatic ring, 1 to 3 substituents selected from halogen, optionally substituted alkyl, alkoxy having 1 to 6 carbon atoms, hydroxy, mercapto, optionally substituted amino, optionally substituted heterocyclic ring, nitro, cyano, carboxy, alkoxycarbonyl and optionally substituted carbamoyl.

Examples of aryloxycarbonyl include phenoxycarbonyl, 1-naphthyloxycarbonyl and 2-naphthyloxycarbonyl. The aryloxycarbonyl may have, on its aromatic ring, 1 to 3 substituents selected from halogen, optionally substituted alkyl, alkoxy having 1 to 6 carbon atoms, hydroxy, mercapto, optionally substituted amino, optionally substituted heterocyclic ring, nitro, cyano, carboxy, alkoxycarbonyl and optionally substituted carbamoyl.

Aralkyloxycarbonyl is that where the alkyl moiety has 1 to 6, preferably 1 to 4, carbon atoms, and is exemplified by benzyloxycarbonyl, 1-naphthylmethyloxycarbonyl and 3-aminobenzyloxycarbonyl. The aralkyloxycarbonyl may have, on its aromatic ring, 1 to 3 substituents selected from halogen, optionally substituted alkyl, alkoxy having 1 to 6 carbon atoms, hydroxy, mercapto, optionally substituted amino, optionally substituted heterocyclic ring, nitro, cyano, carboxy, alkoxycarbonyl having 1 to 6 carbon atoms and optionally substituted carbamoyl.

With regard to heteroarylcarbonyl, the hetero atom constituting the ring is nitrogen, oxygen, sulfur and the like. The heteroarylcarbonyl may have, on its ring, 1 to 3 substituents selected from halogen, optionally substituted alkyl, alkoxy having 1 to 6 carbon atoms, hydroxy, mercapto, optionally substituted amino, optionally substituted heterocyclic ring, nitro, cyano, carboxy, alkoxycarbonyl and optionally substituted carbamoyl, and is exemplified by pyridylcarbonyl (2-pyridylcarbonyl, 3-pyridylcarbonyl, 4-pyridylcarbonyl), quinolylcarbonyl (2-quinolylcarbonyl, 3-quinolylcarbonyl, 4-quinolylcarbonyl), pyridazinylcarbonyl (2-pyridazinylcarbonyl, 3-pyridazinylcarbonyl, 4-pyridazinyl-carbonyl), pyrimidinylcarbonyl (2-pyrimidinylcarbonyl, 3-pyrimidinylcarbonyl, 4-pyrimidinylcarbonyl) and pyrazinylcarbonyl (2-pyrazinylcarbonyl, 3-pyrazinylcarbonyl, 4-pyrazinylcarbonyl).

Heteroarylalkylcarbonyl may have, on its ring, 1 to 3 substituents selected from halogen, optionally substituted alkyl, alkoxy having 1 to 6 carbon atoms, hydroxy, mercapto, optionally substituted amino, optionally substituted heterocyclic ring, nitro, cyano, carboxy, alkoxycarbonyl having 1 to 6 carbon atoms and optionally substituted carbamoyl. Its alkyl moiety has 1 to 4, preferably 1 or 2, carbon atoms and the hetero atom constituting the ring is nitrogen, oxygen, sulfur and the like. The heteroarylalkylcarbonyl is exemplified by pyridylmethylcarbonyl (2-pyridylmethylcarbonyl, 3-pyridylmethylcarbonyl, 4-pyridylmethylcarbonyl), quinolylmethylcarbonyl (2-quinolylmethylcarbonyl, 3-quinolylmethylcarbonyl, 4-quinolylmethylcarbonyl), pyridazinylmethylcarbonyl (2-pyridazinylmethylcarbonyl, 3-pyridazinylmethylcarbonyl, 4-pyridazinylmethylcarbonyl), pyrimidinylmethylcarbonyl (2-pyrimidinylmethylcarbonyl, 3-pyrimidinylmethylcarbonyl, 4-pyrimidinylmethylcarbonyl) and pyrazinylmethylcarbonyl (2-pyrazinylmethylcarbonyl, 3-pyrazinylmethylcarbonyl, 4-pyrazinylmethylcarbonyl).

Optionally substituted carbamoyl may have, on its nitrogen atom, 1 or 2 substituents selected from alkyl having 1 to 6 carbon atoms, cycloalkyl, aryl, aralkyl, heteroaryl and heteroarylalkyl, and is exemplified by carbamoyl, methylcarbamoyl, dimethylcarbamoyl, ethylcarbamoyl and benzylcarbamoyl.

The compounds of the formula (1) wherein the symbols show the following combination are preferable.

$R^1$ is an optionally substituted cycloalkyl or an optionally substituted aryl;

$R^2$ is an alkyl having 1 to 4 carbon atoms;

$R^3$ is an alkyl having 1 to 4 carbon atoms;

a is an integer of 1 to 4;

$R^{14}$ and $R^{15}$ are the same or different and each is a hydrogen, a hydroxy, an alkoxy, an alkyl, a substituted alkyl, an alkenyl, an optionally substituted aryl or an optionally substituted heterocyclic ring;

or $R^{14}$ and $R^{15}$ may combinedly form an optionally substituted 5 to 7-membered heterocyclic ring together with the adjacent nitrogen atom;

Z is an oxygen atom; and $R^{22}$ is an alkyl having 1 to 4 carbon atoms.

The compounds of the formula (1) wherein the symbols show the following combination are particularly preferable.

$R^1$ is a cyclohexyl, a phenyl or a 4-chlorophenyl;

$R^2$ is a methyl;

$R^3$ is a methyl;

a is 1;

$R^{14}$ is a hydrogen;

$R^{15}$ is a hydrogen, a hydroxy, an alkoxy, an alkyl, a substituted alkyl, an alkenyl, an optionally substituted aryl or an optionally substituted heterocyclic ring;

or $R^{14}$ and $R^{15}$ may combinedly form an optionally substituted 5 to 7-membered heterocyclic ring together with the adjacent nitrogen atom;

Z is an oxygen atom; and $R^{22}$ is a methyl.

While the compounds of the formula (1) include optically active compounds due to the chiral carbon atom at the 6-position, the compounds having S configuration (S-isomer) of the formula

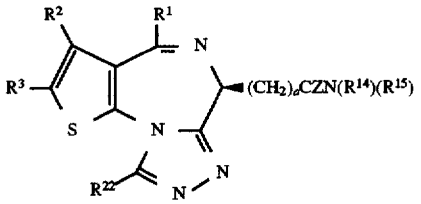

(1a)

wherein each symbol is as defined above, show strong activity.

Examples of the compounds of the formula (1) include (±)-N-(3-pyridazinyl)-4-(4-chlorophenyl)-2,3,9-trimethyl-6H-thieno[3,2-f][1,2,4]triazolo[4,3-a][1,4]diazepine-6-acetamide, (±)-N-(4-pyridazinyl)-4-(4-chlorophenyl)-2,3,9-trimethyl-6H-thieno[3,2-f][1,2,4]triazolo[4,3-a][1,4]diazepine-6-acetamide, (±)-N-(2-aminoethyl)-4-(4-chlorophenyl)-2,3,9-trimethyl-6H-thieno[3,2-f][1,2,4]triazolo[4,3-a][1,4]diazepine-6-acetamide, (±)-N-(3-pyridyl)-4-(4-chlorophenyl)-2,3,9-trimethyl-6H-thieno[3,2-f][1,2,4]triazolo[4,3-a][1,4]diazepine-6-acetamide, (±)-N-(2-dimethylaminoethyl)-4-(4-chlorophenyl)-2,3,9-trimethyl-6H-thieno[3,2-f][1,2,4]triazolo[4,3-a][1,4]diazepine-6-acetamide, (±)-N-methyl-4-(4-chlorophenyl)-2,3,9-trimethyl-6H-thieno[3,2-f][1,2,4]triazolo[4,3-a][1,4]diazepine-6-acetamide, (±)-N-(2-hydroxyethyl)-4-(4-chlorophenyl)-2,3,9-trimethyl-6H-thieno[3,2-f][1,2,4]triazolo[4,3-a][1,4]diazepine-6-acetamide, (±)-3-amino-1-[2-(4-(4-chlorophenyl)-2,3,9-trimethyl-6H-thieno[3,2-f][1,2,4]triazolo[4,3-a][1,4]diazepine-6-yl)-acetyl]pyrazole, (±)-N-(3-hydroxyphenyl)-4-(4-chlorophenyl)-2,3,9-trimethyl-6H-thieno[3,2-f][1,2,4]triazolo[4,3-a][1,4]diazepine-6-acetamide, (S)-N-(4-hydroxyphenyl)-4-(4-chlorophenyl)-2,3,9-trimethyl-6H-thieno[3,2-f][1,2,4]triazolo[4,3-a][1,4]diazepine-6-acetamide, (±)-N-(4-hydroxyphenyl)-4-(4-chlorophenyl)-2,3,9-trimethyl-6H-thieno[3,2-f][1,2,4]triazolo[4,3-a][1,4]diazepine-6-acetamide, (±)-N-(3-aminophenyl)-4-(4-chlorophenyl)-2,3,9-trimethyl-6H-thieno[3,2-f][1,2,4]triazolo[4,3-a][1,4]diazepine-6-acetamide, (±)-N-(4-aminophenyl)-4-(4-chlorophenyl)-2,3,9-trimethyl-6H-thieno[3,2-f][1,2,4]triazolo[4,3-a][1,4]diazepine-6-acetamide, (S)-N-(4-aminophenyl)-4-(4-chlorophenyl)-2,3,9-trimethyl-6H-thieno[3,2-f][1,2,4]triazolo[4,3-a][1,4]diazepine-6-acetamide, (±)-N-carbamoylmethyl-4-(4-chlorophenyl)-2,3,9-trimethyl-6H-thieno[3,2-f][1,2,4]triazolo[4,3-a][1,4]diazepine-6-acetamide, (S)-N-methyl-4-(4-chlorophenyl)-2,3,9-trimethyl-6H-thieno[3,2-f][1,2,4]triazolo[4,3-a][1,4]diazepine-6-acetamide, (R)-N-methyl-4-(4-chlorophenyl)-2,3,9-trimethyl-6H-thieno[3,2-f][1,2,4]triazolo[4,3-a][1,4]diazepine-6-acetamide, (S)-N-(2-hydroxyethyl)-4-(4-chlorophenyl)-2,3,9-trimethyl-6H-thieno[3,2-f][1,2,4]triazolo[4,3-a][1,4]diazepine-6-acetamide, (R)-N-(2-hydroxyethyl)-4-(4-chlorophenyl)-2,3,9-trimethyl-6H-thieno[3,2-f][1,2,4]triazolo[4,3-a][1,4]diazepine-6-acetamide, (S)-N-carbamoylmethyl-4-(4-chlorophenyl)-2,3,9-trimethyl-6H-thieno[3,2-f][1,2,4]triazolo[4,3-a][1,4]diazepine-6-acetamide, (±)-N-pyradinyl-4-(4-chlorophenyl)-2,3,9-trimethyl-6H-thieno[3,2-f][1,2,4]triazolo[4,3-a][1,4]diazepine-6-acetamide, (±)-N-(5-pyrimidinyl)-4-(4-chlorophenyl)-2,3,9-trimethyl-6H-thieno[3,2-f][1,2,4]triazolo[4,3-a][1,4]diazepine-6-acetamide, (S)-N-(2-methoxy-3-pyridyl)-4-(4-chlorophenyl)-2,3,9-trimethyl-6H-thieno[3,2-f][1,2,4]triazolo[4,3-a][1,4]diazepine-6-acetamide, (S)-N-(3-pyridyl)-4-(4-chlorophenyl)-2,3,9-trimethyl-6H-thieno[3,2-f][1,2,4]triazolo[4,3-a][1,4]diazepine-6-acetamide, (±)-N-(2-imidazolyl)-4-(4-chlorophenyl)-2,3,9-trimethyl-6H-thieno [3,2-f][1,2,4]triazolo[4,3-a][1,4]diazepine-6-acetamide, (±)-3-amino-1-(2-(4-(4-chlorophenyl)-2,3,9-trimethyl-6H-thieno [3,2-f][1,2,4]triazolo[4,3-a][1,4]diazepine-6-yl)acetyl)- 1H-1,2,4-triazole, (±)-N-(3-dimethylaminopropyl)-4-(4-chlorophenyl)-2,3,9-trimethyl-6H-thieno[3,2-f][1,2,4]triazolo[4,3-a][1,4]diazepine-6-acetamide, (±)-N-(3-carbamoylphenyl)-4-(4-chlorophenyl)-2,3,9-trimethyl-6H-thieno[3,2-f][1,2,4]triazolo[4,3-a][1,4]diazepine-6-acetamide, (±)-4-(4-chlorophenyl)-2,3,9-trimethyl-6H-thieno[3,2-f][1,2,4]triazolo[4,3-a][1,4]diazepine-6-acetohydroxamic acid, (±)-N-methyl-4-cyclohexyl-2,3,9-trimethyl-6H-thieno[3,2-f][1,2,4]triazolo[4,3-a][1,4]diazepine-6-acetamide, (S)-(−)-N-methoxy-4-(4-chlorophenyl)-2,3,9-trimethyl-6H-thieno[3,2-f][1,2,4]triazolo[4,3-a][1,4]diazepine-6-acetamide and (S)-N-bis(hydroxymethyl)methyl-4-(4-chlorophenyl)-2,3,9-trimethyl-6H-thieno[3,2-f][1,2,4]triazolo[4,3-a][1,4]diazepine-6-acetamide, with preference given to the (S) compounds.

The pharmaceutically acceptable salts of the compounds of the formula (1) are, for example, acid addition salts with inorganic acid (e.g. hydrochloric acid, hydrobromic acid, nitric acid, sulfuric acid and phosphoric acid) or organic acid (e.g. acetic acid, citric acid, succinic acid, fumaric acid, maleic acid, methanesulfonic acid and benzenesulfonic acid), and salts with inorganic base, organic base or amino acid. In view of the object of the present invention, these salts are preferably nontoxic.

The compounds of the formula (1) have at least one chiral carbon atom. Hence, the racemates, optically active compounds and diastereomers thereof are all encompassed in the present invention.

The compounds of the present invention are synthesized as in the following.

Method 1

A compound of the formula

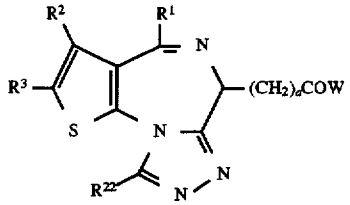

(2)

wherein W is a leaving group such as hydroxy, halogen (e.g. chlorine and bromine), alkoxy (e.g. methoxy and ethoxy), aryloxy (e.g. phenoxy, pentachlorophenoxy and p-nitrophenoxy) and thioester (e.g. phenylthio and 2,6-dimethyl-4-pyridylthio) and other symbols are as defined above, is reacted with a compound of the formula $$HN(R^{14})(R^{15}) \quad (3)$$

wherein each symbol is as defined above, to give a compound of the formula

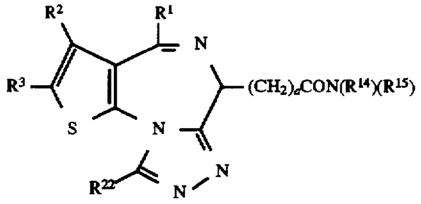

(4)

wherein each symbol is as defined above.

The reaction is carried out in a suitable solvent which does not inhibit the reaction, such as an organic solvent (e.g. tetrahydrofuran, diethyl ether, diisopropyl ether, dioxane, dichloromethane, chloroform, carbon tetrachloride, dichloroethane, ethyl acetate, benzene, toluene, xylene, dimethylformamide, dimethylacetamide and dimethylsulfoxide) in the presence of, where necessary, a base, a thionyl halide, a halide of organic acid or a condensing agent at a temperature of from −60° C. to the boiling point of the solvent.

Examples of the base to be used as necessary include alkali metal hydroxides such as sodium hydroxide and potassium hydroxide, alkali metal carbonates such as sodium carbonate and potassium carbonate, alkali metal hydrogencarbonates such as sodium hydrogencarbonate and potassium hydrogencarbonate, alkali metal hydrides such as sodium hydride, alkali metal alkoxides such as sodium methoxide and potassium tert-butoxide, and organic bases such as triethylamine, pyridine, picolin and N-methylmorpholine. Where necessary, an alkali metal hydroxide, an alkali metal carbonate or an alkali metal hydrogencarbonate may be used in two phases of the above-mentioned organic solvent and water, using a phase transfer catalyst such as tetrabutylammonium bromide and benzyltriethylammonium iodide. Thionyl halide preferably forms a mixed acid anhydride together with the carboxylic acid of the compound of the formula (2) wherein W is hydroxy, and is exemplified by thionyl chloride and thionyl bromide. The halide of organic acid preferably forms a mixed acid anhydride together with the carboxylic acid of the compound of the formula (2) wherein W is hydroxy, and is exemplified by ethyl chloroformate, isobutyl chloroformate and pivaloyl chloride. The condensing agent is preferably one used for amide synthesis, and is exemplified by dicyclohexylcarbodiimide (DCC), N-ethyl-N'-(3-dimethylamino-propyl) carbodiimide hydrochloride (WSC), diphenylphosphoryl azide (DPPA), N-methyl-2-chloropyridinium iodide, benzotriazol-1-yl-oxy-tris(dimethylamino)phosphonium hexafluorophosphate (Bop reagent), 2-chloro-1,3-dimethylimidazolium chloride (DMC) and molecular sieve.

Method 2

A compound of the formula

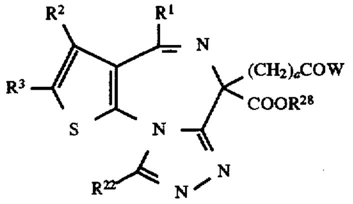

(5)

wherein $R^{28}$ is an alkyl such as methyl and ethyl, and other symbols are as defined above, is reacted with the compound of the formula (3) in an inert solvent such as tetrahydrofuran, dioxane, dichloromethane, benzene, toluene, dimethylformamide and dimethylsulfoxide in the presence of, where necessary, a base such as triethylamine, pyridine and N-methylmorpholine, a thionyl halide (e.g. thionyl chloride), a halide of organic acid (e.g. isobutyl chloroformate and pivaloyl chloride) or a condensing agent [e.g. N-ethyl-N'-(3-dimethylaminopropyl)-carbodiimide hydrochloride (WSC), benzotriazol-1-yl-oxy-tris(dimethylamino) phosphonium hexafluorophosphate (Bop reagent) and 2-chloro-1,3-dimethylimidazolium chloride (DMC)]to give a compound of the formula

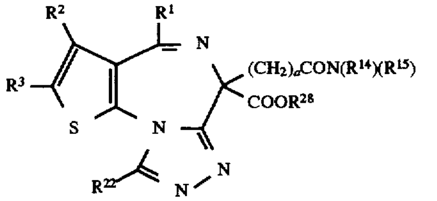

(6)

wherein each symbol is as defined above. This compound is subjected to hydrolysis in water or a mixed solvent of water and a suitable solvent (e.g. methanol, ethanol, tetrahydrofuran and dioxane) in the presence of a base such as lithium hydroxide, sodium hydroxide, potassium hydroxide, sodium carbonate, potassium carbonate, sodium hydrogencarbonate and barium hydroxide at a temperature of from 0° C. to the boiling point of the solvent, and further to decarboxylation using an acid (e.g. hydrochloric acid, sulfuric acid, hydrobromic acid, acetic acid, trifluoroacetic acid and trifluoromethanesulfonic acid) to give a compound of the formula (4).

Method 3

A compound of the formula (4) is reacted with a thiocarbonylating agent such as phosphorus pentasulfide, thiourea, sodium hydrosulfide and 2,4-bis(4-methoxyphenyl)-1,3-dithia-2,4-diphosphetane-2,4-disulfide (Lawesson's reagent) using an organic solvent such as tetrahydrofuran, diethyl ether, diisopropyl ether, dioxane, dichloromethane, chloroform, carbon tetrachloride, dichloroethane, benzene, toluene and xylene at a temperature of from 0° C. to the boiling point of the solvent to give a compound of the formula

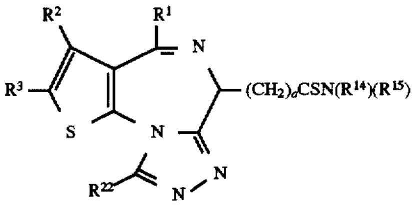

(7)

wherein each symbol is as defined above.

A compound of the formula (2) or (5) wherein W is hydroxy is synthesized as in the following.

Method 4

A compound of the formula

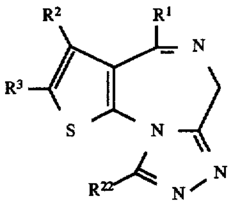

(8)

wherein each symbol is as defined above, is reacted with dialkyl carbonate such as diethyl carbonate in the presence of a base such as sodium hydride, potassium tert-butoxide, lithium diisopropylamide and butyl lithium to introduce alkoxycarbonyl such as ethoxycarbonyl at the 6-position of thieno[3,2-f][1,2,4]triazolo[4,3-a][1,4]diazepine ring, and reacted with a haloester of the formula $$Q-(CH_2)_aCOOR^{27} \quad (9)$$

wherein Q is a halogen such as chlorine and bromine, $R^{27}$ is an alkyl such as methyl and ethyl and a is as defined above, to give a compound of the formula

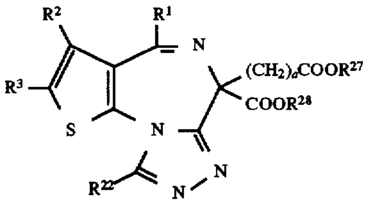

(10)

wherein $R^{28}$ is an alkyl such as methyl and ethyl and other symbols are as defined above.

A compound of the formula (10) is subjected to hydrolysis in water or a mixed solvent of water and a suitable solvent (e.g. methanol, ethanol, tetrahydrofuran and dioxane) in the presence of a base such as lithium hydroxide, sodium hydroxide, potassium hydroxide, sodium carbonate, potassium carbonate, sodium hydrogencarbonate and barium hydroxide at a temperature of from 0° C. to the boiling point of the solvent, and further to decarboxylation by making the reaction system acidic using an acid such as hydrochloric acid, sulfuric acid, acetic acid, hydrobromic acid, trifluoroacetic acid and trifluoromethanesulfonic acid, whereby a compound of the formula

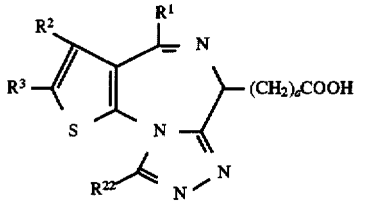

(11)

wherein each symbol is as defined above, is obtained.

From the compound of the formula (10), a compound of the formula

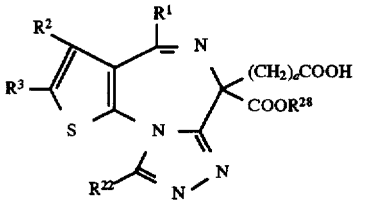

(12)

wherein each symbol is as defined above, which is an intermediate for the compound of the formula (11) can be obtained depending on the conditions of the hydrolysis.

Method 5

The compound of the formula (11) can be directly obtained by reacting the compound of the formula (8) with the compound of the formula (9) in an inert solvent such as tetrahydrofuran, dioxane, diethyl ether, benzene, toluene and dimethylformamide in the presence of a base (e.g. sodium hydride, potassium tert-butoxide, lithium diisopropylamide and butyl lithium) at a temperature of from −50° C. to 0° C., and subjecting the obtained compound to hydrolysis.

A compound of the formula (2) or (5) wherein W is a group other than hydroxy is synthesized as in the following.

Method 6

A compound of the formula (2) or (5) wherein W is a halogen such as chlorine and bromine can be obtained by treating a compound of the formula (11) or (12) with the use of an acid halogenating agent such as thionyl chloride, thionyl bromide, phosphorus pentachloride and phosphorus pentabromide by a conventional method. A compound of the formula (2) or (5) wherein W is an alkoxy such as methoxy and ethoxy, aryloxy (e.g. phenoxy, pentachlorophenoxy and p-nitrophenoxy) or thioester (e.g. phenylthio and 2,6-dimethyl-4-pyridylthio) can be obtained by esterification or thioesterification of a compound of the formula (11) or (12) with a corresponding alcohol (e.g. methanol and ethanol), phenol (e.g. phenol, pentachlorophenoxy and p-nitrophenoxy) or thiophenol (e.g. thiophenol and 2,6-dimethyl-4-pyridinethiol) without solvent or in a solvent inert to the reaction, by a conventional method.

Optically active compounds of the formula (11) can be obtained, for example, by the following methods.

Method (A)

A compound of the formula (11) or (12) is converted to a diastereomer salt with an optically active amine, and resolved by crystallization or recrystallization.

Examples of the amine to form the salt include (1R,2S)-(−)-2-amino-1,2-diphenylethanol, (1S,2R)-(+)-2-amino-1,2-diphenylethanol, D-(−)-arginine, L-(+)-arginine, brucine, cinchonine, cinchonidine, (+)-dehydroabiethylamine, L-(+)-lysine, (R)-(+)-1-(1-naphthyl)ethylamine, (S)-(−)-1-(1-naphthyl)ethylamine, (R)-(+)-1-phenethylamine, (S)-(−)-1-phenethylamine, quinine and strychnine, and crystallization is performed in a solvent such as methanol, ethanol, 1-propanol, 2-propanol, acetone, ethyl acetate and acetonitrile. The thus-obtained optically active compound of the formula (11) or (12) is subjected to hydrolysis in water or a mixed solvent of water and a suitable solvent (e.g. methanol, ethanol, tetrahydrofuran and dioxane) in the presence of a base such as lithium hydroxide, sodium hydroxide, potassium hydroxide, sodium carbonate, potassium carbonate, sodium hydrogencarbonate and barium hydroxide at a temperature of from 0° C. to the boiling point of the solvent. In the case of the compound of the formula (12), the compound is further subjected to decarboxylation using an acid such as hydrochloric acid, sulfuric acid, hydrobromic acid, acetic acid, trifluoroacetic acid and trifluoromethanesulfonic acid, whereby an optically active compound of the formula (11) can be obtained.

Method (B)

The compound of the formula (11) or (12) is converted to a diastereomer ester with an optically active alcohol and resolved.

The compound of the formula (11) or (12) is esterified with an optically active alcohol such as (R)-(−)-2-butanol, S-(+)-2-butanol, (+)-menthol, (−)-menthol, (R)-(+)-1-phenylethanol and (S)-(−)-1-phenylethanol by a conventional method; resolved by column chromatography, recrystallization and the like; and subjected to hydrolysis in water or a mixed solvent of water and a suitable solvent (e.g. methanol, ethanol, tetrahydrofuran and dioxane) in the presence of a base such as lithium hydroxide, sodium hydroxide, potassium hydroxide, sodium carbonate, potassium carbonate, sodium hydrogencarbonate and barium hydroxide at a temperature of from 0° C. to the boiling point of the solvent. In the case of the compound of the formula (12), the compound is further subjected to decarboxylation using an acid such as hydrochloric acid, sulfuric acid, hydrobromic acid, acetic acid, trifluoroacetic acid and trifluoromethanesulfonic acid, whereby an optically active compound of the formula (11) can be obtained.

Method (C)

A compound of the formula (10), (11) or (12) is converted to a diastereomer salt with an optically active sulfonic acid and resolved by crystallization or recrystallization.

Examples of the optically active sulfonic acid to form the salt include (+)-10-camphorsulfonic acid, (−)-10-camphorsulfonic acid, (+)-3-bromocamphor-8-sulfonic acid and (−)-3-bromocamphor-8-sulfonic acid. The crystallization is performed in a solvent such as methanol, ethanol, 1-propanol, 2-propanol, acetone, ethyl acetate and acetonitrile. The thus-obtained optically active compound of the formula (10), (11) or (12) is subjected to hydrolysis in water or a mixed solvent of water and a suitable solvent (e.g. methanol, ethanol, tetrahydrofuran and dioxane) in the presence of a base such as lithium hydroxide, sodium hydroxide, potassium hydroxide, sodium carbonate, potassium carbonate, sodium hydrogencarbonate and barium hydroxide at a temperature of from 0° C. to the boiling point of the solvent. In the case of the compound of the formula (10) or (12), the compound is further subjected to decarboxylation using an acid such as hydrochloric acid, sulfuric acid, hydrobromic acid, acetic acid, trifluoroacetic acid and trifluoromethanesulfonic acid, whereby an optically active compound of the formula (11) can be obtained.

Method (D): Asymmetric hydrolysis by enzyme

A compound of the formula (12) is subjected to asymmetric hydrolysis using a lipase derived from microorganisms, a lipoprotein lipase derived from microorganisms, an esterase derived from animal tissues or an esterase derived from plant tissues. While the pH and the reaction temperature of the hydrolysis by enzymes vary depending on the enzyme to be used, the hydrolysis is generally performed at pH 4–9 at 10°–50° C. The thus-obtained optically active compound of the formula (12) is further subjected to decarboxylation using an acid (e.g. hydrochloric acid, sulfuric acid, hydrobromic acid, acetic acid, trifluoroacetic acid and trifluoromethanesulfonic acid), whereby an optically active compound of the formula (11) can be obtained.

Method (E): Synthesis using an optically active starting material

A compound of the formula

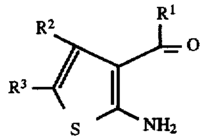
(13)

wherein each symbol is as defined above, and a compound of the formula

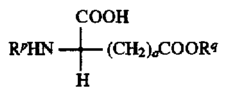
(14)

wherein $R^p$ and $R^q$ are each a protecting group used for amino acid synthesis, such as tert-butyloxycarbonyl, benzyloxycarbony 1, 9-fluorenylmethyloxycarbonyl, acetyl and phthaloyl for $R^p$, and methyl, ethyl, tert-butyl, benzyl and cyclohexyl for $R^q$, and a is as defined above, which is derived from an optically active amino acid (e.g. D- and L-aspartic acid, D- and L-glutamic acid and D- and L-2-aminoadipic acid) are reacted in an inert solvent such as tetrahydrofuran, dioxane, dichloroethane, benzene, toluene, dimethylformamide and dimethylsulfoxide in the presence of, where necessary, a base such as triethylamine, pyridine and N-methylmorpholine, thionyl halide (e.g. thionyl chloride), a halide of organic acid (e.g. isobutyl chloroformate and pivaloyl chloride), or a condensing agent (e.g. N-ethyl-N'-(3-dimethylaminopropyl)carbodiimide hydrochloride (WSC), benzotriazol-1-yl-oxy-tris(dimethylamino) phosphonium hexafluorophosphate (Bop reagent) and 2-chloro-1,3-dimethylimidazolium chloride (DMC) to give a compound of the formula

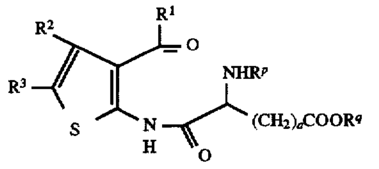
(15)

wherein each symbol is as defined above. This compound is deprotected and subjected to dehydrocyclization to synthesize a compound of the formula

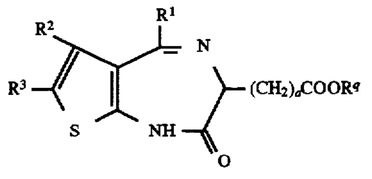
(16)

wherein each symbol is as defined above. Then, the compound of the formula (16) is converted to a compound of the formula

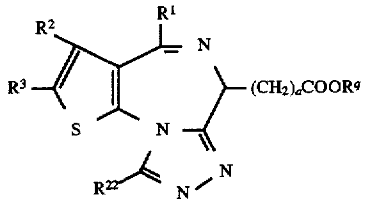
(17)

wherein each symbol is as defined above, by a conventional method to be described later and deprotected, whereby an optically active compound of the formula (11) can be obtained.

The compounds (1) of the present invention thus obtained can be separated and purified from reaction mixtures by a method known per se, such as recrystallization and column chromatography.

The compounds of the formula (1) are treated with inorganic acid (e.g. hydrochloric acid, hydrobromic acid, sulfuric acid, phosphoric acid and nitric acid), organic acid (e.g. acetic acid, propionic acid, succinic acid, glycolic acid, lactic acid, malic acid, tartaric acid, citric acid, maleic acid, fumaric acid, methanesulfonic acid, benzenesulfonic acid, p-toluenesulfonic acid and ascorbic acid), inorganic base (e.g. sodium hydroxide, potassium hydroxide, calcium hydroxide, magnesium hydroxide, zinc hydroxide and ammonium hydroxide), organic base (e.g. methylamine, diethylamine, triethylamine, dicyclohexylamine, triethanolamine, ethylenediamine, trishydroxymethylaminomethane, quinine, guanidine and cinchonine) or amino acid (lysine, ornithine, arginine, alanine) to give salts. The present invention encompasses hydrates and solvates.

When the compounds of the present invention have a chiral carbon atom, they are generally obtained as racemates which are resolved into optical isomers by conventional methods. Such optical isomers can be also produced from an optically active starting material. Respective diastereomers can be purified by fractional crystallization or chromatography.

The compound of the formula (8) used in the above-mentioned Method 4 is synthesized as in the following.

A compound of the formula

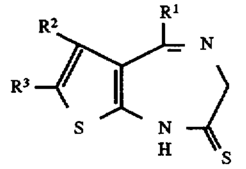
(19)

wherein each symbol is as defined above, which is obtained by reacting a compound of the formula

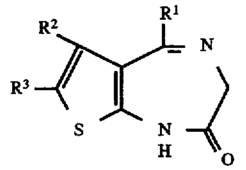
(18)

wherein each symbol is as defined above, with a thionating agent by the method described in U.S. Pat. No. 4,960,770 and U.S. Pat. No. 4,820,703 (corresponding to Japanese Patent Unexamined Publication Nos. 79185/1989 and 156982/1989, respectively) and a compound of the formula $$R^{22}CONHNH_2 \quad (20)$$

wherein $R^{22}$ is as defined above, are reacted, whereby a compound of the formula (8) is obtained.

Alternatively, a compound of the formula

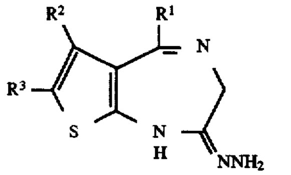

(21)

wherein each symbol is as defined above, which is obtained by reacting a compound of the formula (19) with a hydrazine hydrate, is reacted with a compound of the formula $R^{22}COOH$ (22)

wherein $R^{22}$ is as defined above, a reactive derivative thereof or a compound of the formula $R^{22}C(OR^{29})_3$ (23)

wherein $R^{29}$ is an alkyl such as methyl and ethyl and $R^{22}$ is as defined above, whereby a compound of the formula (8) is produced.

The reaction between the compound of the formula (19) and the compound of the formula (20) generally proceeds in a solvent inert to the reaction (e.g. benzene, toluene, xylene, tetrahydrofuran, dioxane and a mixed solvent thereof), in the presence of an organic acid (e.g. acetic acid and propionic acid), an inorganic acid (e.g. hydrochloric acid and sulfuric acid) or silica gel at a temperature of from room temperature to the refluxing temperature of the solvent used, for 30 minutes to 5 hours. The reaction between the compound of the formula (19) and the hydrazine hydrate generally proceeds in a solvent inert to the reaction (e.g. methanol, ethanol, propanol, isopropyl alcohol and butanol) at 0–40° C. for about 5 minutes to 3 hours.

The reaction between the compound of the formula (21), and the compound of the formula (22), its reactive derivative or the compound of the formula (23) proceeds in a solvent inert to the reaction (e.g. benzene, toluene, xylene, tetrahydrofuran, dioxane and a mixed solvent thereof), in the presence of an organic acid (e.g. acetic acid and propionic acid), an inorganic acid (e.g. hydrochloric acid and sulfuric acid) or silica gel at a temperature from room temperature to the refluxing temperature of the solvent used, for 30 minutes to 6 hours using a Dean-Stark trap.

Experiment 1

Effect on CD11b expression human histiocytic leukemia cell line, U937 cells

Effect on the expression of CD11b antigen, which is the α chain of an adhesion molecule, Mac-1 expressing on the surface of leukocytgic cells, was investigated. U937 cells were suspended in RPMI1640 medium containing 20% fetal calf serum (FCS), plated with phorbol 12,13-dibutyrate (PDB, 10 ng/ml) into 96-well filtration plates, and cultured for 3 days at 37° C. in 5% $CO_2$. After the cells were washed once with RPMI1640 medium, rat anti-human CD11b antibody (2 μg/ml) was added to each well and the plates were incubated for 1 hr on ice. After the cell were washed twice, peroxidase-conjugated anti-rat immunoglobulin antibody (1 μg/ml) was added, and the cells were incubated for 1 hr on ice. After the cells were washed 3 times, substrate for peroxidase (o-phenylenediamine) was added. After the plates were stood for 15 min at room temperature, absorbance at 490 nm was measured with a 96-well microplate reader and was regarded as a indicator of CD11b antigen expression.

Table 1 shows $IC_{50}$ values (μM) obtained by calculating % inhibition when the absorbance in the presence and absence of PDB was taken as 100% and 0%, respectively.

TABLE 1

| Test Compound | Inhibitory effect on CD11b expression ($IC_{50}$, μM) |
|---|---|
| Example 1 | 0.26 |
| Example 2 | 0.15 |
| Example 5 | 0.26 |

As shown in Table 1, these compounds were clarified to inhibit CD11b expression in U937 cells.

Experiment 2

Inhibitory effect on expression of VCAM-1 and ELAM-1 in human umbilical vein-derived endothelial cells (HUVECs)

HUVECs were suspended in 199 medium containing 20% FCS, 20 μg/ml endothelial cell growth factor derived from bovine brain, and 100 μg/ml heparin, plated into 96-well microculture plates coated with collagen, and cultured at 37° C. in 5% $CO_2$. When cells were grown to confluence, the cells received tumour necrosis factor (TNF)-α (20 U/ml for VCAM-1 expression, 100 U/ml for ELAM-1 expression) and cultured for 5 hr. After the cells were washed once with 199 medium, mouse anti-human VCAM-1 monoclonal antibody (2 μg/ml) or rat anti-human ELAM-1 monoclonal antibody (2 μg/ml) was added, and the cells were incubated for 1 hr at room temperature. After the cells were washed twice, peroxidase-conjugated anti-mouse immunoglobulin antibody or anti-rat immunoglobulin antibody was added, and the cells were incubated for 1 hr at room temperature. After the cells were washed 3 times, 2,2'-azino-bis(3-ethylbenzothiazolone-6-sulfonic acid) was added. After the plates were stood for 15 min at room temperature, absorbance at 405 nm with a reference wave length of 490 nm was measured with a 96-well microplate reader and was regarded as a indicator of VCAM-1 or ELAM-1 expression.

Table 2 shows $IC_{50}$ values (μM) obtained by calculating % inhibition when the absorbance in the presence and absence of TNF-α was taken as 100% and 0%, respectively.

TABLE 2

| | Inhibitory effect ($IC_{50}$, μM) on | |
|---|---|---|
| Test Compound | CAM-1 expression | ELAM-1 expression |
| Example 1 | 0.025 | 0.052 |
| Example 2 | 0.037 | 0.079 |
| Example 5 | 0.0045 | 0.014 |

As shown in Table 2, these compounds were clarified to inhibit expression of VACM-1 and ELAM-1 in HUVECs.

Experiment 3

Effect on oxazolone-induced ear edema in mice.

Mice were sensitized by applying 50 μl of oxazolone solution (50 mg/ml in acetone) to their shaved abdomen on day 0. On day 7, 5 μl of oxazolone solution was applied to each surface of the right ear. After 24 hr (day 8), the right and left ears were cut off with a puncher of 6 mm in diameter and weighed with an electronic reading balance. The difference in weight between the oxazolone-treated ear (right) and untreated ear (left) was taken to reflect the extent of ear edema. Test compounds were suspended in 0.5% hydroxypropylmethycellulose solution and administered p.o. (0.1 ml/10 g body weight) on days 0 to 4 (once a day) and day 7 (twice a day).

Table 3 shows the result.

TABLE 3

| Treatment | Test compound | Dose mg/kg) | Increase in ear weight (mg, mean ± S.D.) |
|---|---|---|---|
| Unsensitized | | 0 | 6.8 ± 2.5 |
| Sensitized | | 0 | 17.5 ± 1.0 |
| Sensitized | Example 1 | 0.1 | 16.3 ± 1.0 |
| Sensitized | Example 1 | 0.3 | 15.0 ± 0.6* |
| Sensitized | Example 1 | 1 | 14.2 ± 0.8** |
| Sensitized | Example 2 | 0.3 | 14.3 ± 1.5** |
| Sensitized | Example 2 | 1 | 14.2 ± 0.4** |
| Unsensitized | | 0 | 12.0 ± 1.5 |
| Sensitized | | 0 | 16.2 ± 0.8 |
| Sensitized | Example 5 | 1 | 15.2 ± 0.8 |
| Sensitized | Example 5 | 3 | 14.0 ± 0.6** |
| Sensitized | Example 5 | 10 | 13.3 ± 0.5** |

*: $P < 0.05$,
**: $P < 0.01$ vs. sensitized control (Dunnett's test, N = 6)

As shown in Table 3, these compounds were clarified to inhibit ear edema in mice in a dose-dependent manner and suggested to suppress infiltration of leukocytes into inflammatory site by inhibiting cell adhesion in in vino.

Experiment 4

Effect on thioglycollate (TG) medium-induced infiltration of leukocytes

One ml of TG medium was injected into peritoneal cavity of BALB/c mice on day 0. On day 4, leukocytes infiltrating into the peritoneal cavity were collected with 3 ml of phosphatebuffered saline containing 0.02% EDTA and the density of leukocytes (cells/ml) was counted with an automatic blood cell counter. Total number of leukocytes (X) was calculated from the density of leukocytes (A) with the following formula.

$$X=3A$$

Test compounds were suspended in 0.5% hydroxypropylmethyl-cellulose solution and administered p.o. (0.1 ml/10 g body weight) on days 0 to 3.

Table 4 shows the result.

TABLE 4

| TG medium (ml) | Test compound | Dose (mg/kg/day) | Total number of leukocytes ($\times 10^4$, mean ± S.D.) |
|---|---|---|---|
| 0 | | 0 | 296 ± 88 |
| 1 | | 0 | 1192 ± 183 |
| 1 | Example 1 | 0.03 | 1059 ± 285 |
| 1 | Example 1 | 0.1 | 719 ± 308* |
| 1 | Example 1 | 0.3 | 442 ± 117** |
| 1 | Example 2 | 0.03 | 1064 ± 359 |
| 1 | Example 2 | 0.1 | 594 ± 302** |
| 1 | Example 2 | 0.3 | 570 ± 203** |
| 0 | | 0 | 297 ± 106 |
| 1 | | 0 | 1231 ± 183 |
| 1 | Example 5 | 0.03 | 1221 ± 239 |
| 1 | Example 5 | 0.1 | 990 ± 327 |
| 1 | Example 5 | 0.3 | 596 ± 165** |

*: $P < 0.05$,
**: $p < 0.01$ vs. TG medium-injected control (Dunnett's test, N = 6)

As shown in Table 4, these compounds were clarified to inhibit TG medium-induced infiltration of leukocytes in a dose-dependent manner and suggested to suppress infiltration of leukocytes into inflammatory site by inhibiting cell adhesion in vivo.

Experiment 5

Effect on lipopolysaccharide (LPS)-induced adhesion of leukocytes

It has been reported that, by the administration of LPS to mice, an adhesion molecule, Mac-1-dependent leukocyte adhesion is induced, the leukocytes infiltrate into lung, liver and so on, and in result the number of peripheral blood leukocytes reduces (Morisaki et al., Clin. Immunol. Immunopathol., 61, 365–375, 1991). The effect on LPS-induced leukocyte adhesion was investigated by taking the reduction of peripheral blood leukocytes as an indicator of leukocyte adhesion.

LPS solution (50 ng/ml in saline, 0.5 ml/mouse) was injected into peritoneal cavity of BALB/c mice on day 0. Six hr after the LPS injection, the number of peripheral blood leukocytes was counted with an automatic blood cell counter. Test compounds were suspended in 0.5% hydroxypropylmethylcellulose solution and administered p.o. (0.1 ml/10 g body weight) on days −4 to 0.

Table 5 shows the result.

TABLE 5

| Treatment | Test compound | Dose (mg/kg/day) | Number of peripheral blood leukocytes (× 100/μl, mean ± S.D.) |
|---|---|---|---|
| Saline | | 0 | 67 ± 6 |
| LPS | | 0 | 25 ± 4 |
| LPS | Example 1 | 0.3 | 32 ± 5 |
| LPS | Example 1 | 1 | 50 ± 15** |
| LPS | Example 1 | 3 | 61 ± 13** |
| Saline | | 0 | 79 ± 13 |
| LPS | | 0 | 28 ± 5 |
| LPS | Example 5 | 1 | 46 ± 8 |
| LPS | Example 5 | 3 | 69 ± 18** |
| LPS | Example 5 | 10 | 103 ± 16** |

**: $P < 0.01$ vs. LPS-injected control (Dunnett's test, N = 6)

As shown in Table 5, these compounds were clarified to inhibit the reduction of peripheral blood leukocytes caused by LPS-induced adhesion of leukocytes in a dose-dependent manner and suggested to inhibit cell adhesion in vivo.

Experiment 6

Effect on trinitrobenzenesufonic acid (TNBS)-induced colitis model in rats

Colitis was induced by intrarectal injection of TNBS solution (60 mg/ml in 50% EtOH, 500 μl/rat) to SD rats. Seven days later, rats were sacrificed and large intestine (8 cm from anus) was cut off and weighed. Myeloperoxidase (MPO) activity in the intestinal tissue was measured as follows and taken as an indicator of leukocyte infiltration: the intestinal tissue was homogenized and a cycle of freeze-thawing of the tissue was repeated 3 times. The supernatant obtained by centrifugation was assayed for MPO activity with substrate for peroxidase (o-phenylenediamine). MPO activity in the supernatant was calculated with the commercial MPO as a standard. The increases in intestinal weight and MPO activity as described above were taken as indicators of colitis. Test compound was suspended in 0.5% hydroxypropylmethylcellulose solution and administered p.o. (0.1 ml/10 g body weight) for 5 days beginning on the day of TNBS injection.

Table 6A and 6B show the result of intestinal weight and MPO activity, respectively.

TABLE 6A

| Treatment | Example 1 (mg/kg/day) | Intestinal weight (mg, mean ± S.D.) | Significance* |
|---|---|---|---|
| None | 0 | 425.9 ± 59.6 | |
| TNBS | 0 | 3655.1 ± 1557.6 | Control |

TABLE 6A-continued

| Treatment | Example 1 (mg/kg/day) | Intestinal weight (mg, mean ± S.D.) | Significance* |
|---|---|---|---|
| TNBS | 0.3 | 1328.6 ± 1411.4 | P < 0.01 |
| TNBS | 1 | 574.2 ± 93.1 | P < 0.01 |

*: Dunnett's test

TABLE 6B

| Treatment | Example 1 (mg/kg/day) | MPO activity (U/ml, mean ± S.D.) | Significance* |
|---|---|---|---|
| None | 0 | 0.230 ± 0.045 | |
| TNBS | 0 | 3.283 ± 1.629 | Control |
| TNBS | 0.3 | 1.389 ± 2.806 | P < 0.05 |
| TNBS | 1 | 0.221 ± 0.020 | P < 0.01 |

*: Mann-Whitney's U-test

As shown in Table 6A and 6B, the compound of Example 1 was clarified to significantly inhibit the increase in intestinal weight and the leukocyte infiltration caused by colitis in rats and suggested to be available as therapeutic or prophylactic drug for human inflammatory bowel diseases (ulcerative colitis and Crohn's disease).

Experiment 7

Effect on trinitrobenzenesufonec acid (TNBS)-induced colitis model in rats.

Colitis was induced by intrarectal injection of TNBS solution (60 mg/ml in 50% EtOH, 500 μl/rat) to SD rats. Seven days later, rats were sacrificed, and large intestine (8 cm from anus) was cut off and weighed. Myeloperoxidase (MPO) activity in the intestinal tissue was measured as follows and taken as an indicator of leukocyte infiltration: the intestinal tissue was homogenized and a cycle of freeze-thawing of the tissue was repeated 3 times. The supernatant obtained by centrifugation was assayed for MPO activity with substrate for peroxidase (o-phenylenediamine). MPO activity in the supernatant was calculated with the commercial MPO as a standard. The increases in intestinal weight and MPO activity as described above were taken as indicators of colitis. Test compounds were suspended in 0.5% hydroxypropylmethylcellulose solution and administered intrarectally (o.2 ml/rat) for 5 days beginning on the day of TNBS injection.

Table 7A and 7B show the results of intestinal weight and MPO activity, respectively.

TABLE 7A

| Treatment | Test compound | Dose (mg/site) | Intestinal weight (mg, mean ± S.D.) | Significance* |
|---|---|---|---|---|
| None | | 0 | 431.3 ± 47.2 | |
| TNBS | | 0 | 2304.2 ± 1375.0 | Control |
| TNBS | Example 3 | 0.01 | 501.5 ± 78.3 | P < 0.01 |
| TNBS | Example 3 | 0.1 | 472.0 ± 43.4 | P < 0.01 |
| TNBS | Example 3 | 1 | 460.8 ± 52.3 | P < 0.01 |
| TNBS | Example 4 | 0.01 | 490.8 ± 89.9 | P < 0.01 |
| TNBS | Example 4 | 0.1 | 488.1 ± 24.0 | P < 0.01 |
| TNBS | Example 4 | 1 | 511.8 ± 98.5 | P < 0.01 |

*: Dunnett's test

TABLE 7B

| Treatment | Test compound | Dose (mg/site) | MPO activity (U/ml, mean ± S.D.) | Significance* |
|---|---|---|---|---|
| None | | 0 | 0.457 ± 0.079 | |
| TNBS | | 0 | 6.211 ± 5.106 | Control |
| TNBS | Example 3 | 0.01 | 0.716 ± 0.158 | P < 0.05 |
| TNBS | Example 3 | 0.1 | 0.654 ± 0.109 | P < 0.05 |
| TNBS | Example 3 | 1 | 0.676 ± 0.172 | P < 0.05 |
| TNBS | Example 4 | 0.01 | 0.703 ± 0,313 | P < 0.05 |
| TNBS | Example 4 | 0.1 | 0.511 ± 0.103 | P < 0.01 |
| TNBS | Example 4 | 1 | 0.488 ± 0.103 | P < 0.01 |

*: Mann-Whitney's U-test

As shown in Table 7A and 7B, these compounds were clarified to significantly inhibit the increase in intestinal weight and the leukocyte infiltration caused by colitis in rats and suggested to be available as therapeutic or prophylactic drugs for human inflammatory bowel diseases (ulcerative colitis and Crohn's disease).

Experiment 8

Effect on glomerulonephritis in mice

Rabbit immunoglobulin G solution (4 mg/ml in saline) was mixed with Freund's complete adjuvant at a ratio of 1:1 and the emulsion was prepared. The emulsion was injected into peritoneal cavity of female C57BL/6 mice (0.25 ml/mouse). After 5 days, rabbit anti-mouse glomerular basement membrane (GBM) antiserum obtained by the method of Nagai et al. (Japan. J. Pharmacol., 32, 1117, 1982) was administered i.v. (0.08 ml/mouse). Protein level in urine was measured with ames reagent strips for urinalysis on the consecutive days and scored as follows: negative, 0 point; ±, 1 point, +, 2 point; ++, 3 points; +++, 4 points; ++++, 5 points (Table 8 shows the mean score of each group). Test compounds were suspended in 0.5% hydroxypropylmethylcellulose (HPMC) solution and administered p.o. (0.1 ml/10 g body weight) for 13 days beginning on the day of anti-GBM ant-serum injection.

Table 8 shows the scores on 12 days (the day of last administration) after the anti-GBM antiserum injection.

TABLE 8

| Treatment | Dose (mg/kg/day) | Score (mean ± S.D.) |
|---|---|---|
| Normal rabbit serum + HPMC | | 2.00 ± 0.00 |
| Anti-GBM antiserum + HPMC | | 4.33 ± 0.50 |
| Example 1 | 1 | 2.56 ± 0.53** |
| Example 1 | 3 | 2.22 ± 0.67** |
| Example 2 | 1 | 3.25 ± 0.16* |
| Example 2 | 3 | 2.44 ± 0.53** |
| Example 5 | 1 | 3.44 ± 0.88* |
| Example 5 | 3 | 2.22 ± 0.44** |

*: P < 0.05,
**: P < 0.01 vs. anti-GBM antiserum + HPMC control (Mann-whitney's U-test)

As shown in Table 8, these compounds were clarified to significantly inhibit the increase in protein level in urine caused by glomerulonephritis in mice and suggested to be available as therapeutic or prophylactic drugs for various human nephritis.

Experiment 9

Effect on antigen induced Eosinophils accumulation into lungs in actively sensitized guinea pigs Animals Male Dunkin-Hartley guinea pigs (4W, Japan SLC, Inc.) were used throughout this study.

Drug treatments

Sensitized animals were orally administered (p.o.) with compound or solvent (0.5% hydroxymethylcellulose) 30 min. before final sensitization, 30 min. before antigen exposure and 4.5 h after antigen exposure.

Sensitization and antigen exposure

Egg albumin (EA, 10 μg) was added to $Al(OH)_3$ (10 mg) in sterile physiological saline (0.5 ml) and mixed in a blender. This mixture was injected intraperitoneally into recipients. And after 14 days and 21 days, the procedure was repeated. Seven days after the final sensitization procedure, Mepyramine 10 mg/kg was injected intraperitoneally into the sensitized animals. After 30 min., the animals were exposed to aerosol of 1% EA in sterile physiological saline for 5 min.

Bronchoalveolar lavage and cell counting 24 h after antigen exposure, the animals were killed by exsanguination and tracheae were cannulated. And the lungs were lavaged three times with 10 ml of sterile physiological saline. Lavage fluid (BALF) was centrifuged (800 rpm for 10 min. at 4° C.) and the cell pellet was resuspended in 10 ml of sterile physilolgical saline and total cell numbers in BALF were counted in a hemocytometer (MEK 4200, Nihon-kohden, Ltd.). Differential cell counts were made from centrifuged preparations stained with May-Giemsa stain.

Results

TABLE 9

| Test compound | Dose (mg/kg, p.o.) | Number of eosinophils (× $10^6$) |
|---|---|---|
| Callenge control[1)] | | 31.9 ± 8.4 |
| Normal control[2)] | | 4.9 ± 1.9** |
| Example 1 | 30 | 7.0 ± 1.4** |
| Example 2 | 30 | 11.8 ± 3.8* |

1)Sensitized, solvent administered (p.o.) and antigen exposed

2)Not sensitized, solvent administered (p.o.) and sterile physiological saline exposed

*: P < 0.05, **: P < 0.01 vs. Challenge control

Table 9 shows eosinophils counts in the BALF 24th after antigen exposure. These compounds significantly decreased the number of eosinophils. This result suggests that these compounds would be effective drugs for asthma.

The acute toxicity of the compound of the present invention was examined using 6 male mice. The test compounds were administered orally and the mice were monitored for 6 days. As a result, no death case was observed in a dose of 1,000 mg/kg.

Industrial Applicability

As is evident from the Experimental Examples as described, the compound of the present invention has (1) inhibitory effect on leukocyte adhesion to human umbilical vein-derived endothelial cells (HUVEC) by inhibiting the CD11b expression on leukocytes, (2) inhibitory effect on the VCAM-1, ELAM-1 expression on HUVEC, and (3) inhibitory effect on leukocyte filtration in vivo. These effects suggest that the compound of the present invention is useful as a preventive and therapeutic drug for various diseases in which cell adhesion is involved in the onset and progress thereof. In fact, significant suppression of inflammations has been demonstrated in the experiments using colitic model animals and nyphritic model animals. Furthermore, the compound of the present invention significantly suppressed eosinotaxis, thus suggesting its usefulness as a preventive and therapeutic drug for asthma.

Based on the above-mentioned effects, it is evident that the compound of the present invention is useful as a preventive and therapeutic drug for inflammatory diseases (e.g. inflammatory intestinal diseases such as ulcerative colitis and Crohn's disease, nephritis such as glomerulonephritis, and inflammatory skin diseases such as allergic dermatitis) and allergic diseases (e.g. asthma such as bronchial asthma), in which cell adhesion is involved. In addition, the compound of the present invention can be used for preventing and treating autoimmune diseases [e.g. rheumatoid arthritis and systemic lupus erythematosus (SLE)], ischemic heart diseases (e.g. ischemia-reperfusion injury), septic shock, diabetes and graft rejection in organ transplantation, as well as for the prevention of metastasis of malignant cells. The compound of the present invention has been proved to be low-toxic in the experiments using animals, and therefore, is useful as a highly safe pharmaceutical.

When the compound of the present invention or a pharmaceutically acceptable salt thereof is used as a pharmaceutical, pharmaceutically acceptable additives such as carriers, excipients, diluents and solubilizers (e.g. lactose, corn starch, talc, kaolin, physiological saline and sterilized water) are generally admixed therewith and formulated into the dosage form of, for example, tablet (sugar-coated tablet and film-coated tablet inclusive), capsule, powder, injection, transfusion, suppository or cataplasm, which can be administered safely to patients. While the dose varies depending on sex, age, body weight and symptom of the patients, it is preferably about 1 to 500 mg for an adult per day by oral administration.

BEST MODE FOR EMBODYING THE INVENTION

The present invention is explained in more detail in the following by reference to Starting Material Preparation Examples and Examples. Needless to say, the present invention is not limited to these Examples.

Starting Material Preparation Example 1

4-Chlorophenyl cyanomethyl ketone, morpholine and ethyl methyl ketone are dissolved in ethanol, and sulfur is suspended. The suspension is refluxed under heating for 10 hours. After the completion of the reaction, the solvent is distilled away under reduced pressure, and the residue is dissolved in chloroform. The mixture is washed with water, and dried over anhydrous magnesium sulfate. Chloroacetyl chloride is dropwise added, and the mixture is refluxed under heating for 1 hour. After the completion of the reaction, the resulting mixture is washed with a saturated aqueous solution of sodium hydrogencarbonate and dried over anhydrous magnesium sulfate, and the solvent is distilled away under reduced pressure. Methanol is added to the residue and crystallized to give N-(2-(3-(4-chlorobenzoyl)-4,5-dimethyl)thienyl)chloroacetamide. This compound is dissolved in tetrahydrofuran, and sodium iodide is suspended therein. The suspension is refluxed under heating for 2 hours. The reaction mixture is cooled to −50° C. with dry ice-acetone, and liquid ammonia is added, followed by stirring. After the completion of the reaction, the solvent is distilled away under reduced pressure, and the residue is dissolved in ethyl acetate. After washing with water, the mixture is dried over anhydrous magnesium sulfate, and the solvent is distilled away under reduced pressure. The residue is dissolved in isopropyl alcohol, and acetic acid is added. The mixture is refluxed under heating for 5 hours. The solvent is distilled away under reduced pressure, and the residue is dissolved in chloroform. The mixture is washed with a saturated aqueous solution of $NaHCO_3$, and dried over anhydrous magnesium sulfate. The solvent is distilled away under reduced pressure, and crystallization from ethyl acetate affords 5-(4-chlorophenyl)-6,7-dimethyl-1,2-dihydro-3H-thieno[2,3-e][1,4]diazepin-2-one.

5-(4-Chlorophenyl)-6,7-dimethyl-1,2-dihydro-3H-thieno [2,3-e][1,4]diazepin-2-one is dissolved in chloroform, and diphosphorus pentasulfide is added with stirring. The mixture is refluxed under heating for 3 hours. After the completion of the reaction, the reaction mixture is neutralized with a saturated aqueous solution of sodium hydrogencarbonate, washed with water and dried over anhydrous magnesium sulfate. The solvent is distilled away under reduced pressure, and the residue is suspended in methanol. To the suspension is added 100% hydrazine hydrate under cooling, and the mixture is stirred at room temperature for 2 hours. After the completion of the reaction, precipitated crystals are collected by filtration to give 5-(4-chlorophenyl)-6,7-dimethyl-1,2-dihydro-3H-thieno[2,3-e][1,4]diazepin-2-hydrazone, melting point 226° C. (decomposition). This compound is suspended in toluene, and triethyl orthoacetate is added. The mixture is stirred at 80° C. for 4 hours. After the completion of the reaction, the solvent is distilled away under reduced pressure, and obtained crude crystals are recrystallized from ethyl acetate to give 4-(4-chlorophenyl)-2,3,9-trimethyl-6H-thieno[3,2-f][1,2,4]triazolo[4, 3-a][1,4]diazepine, melting point not less than 250° C.

$^1$H-NMR ($CDCl_3$, ppm) δ:1.64 (s,3H), 2.39 (s,3H), 2.63 (s,3H), 4.06 (d,1H,J=12 Hz), 5.06 (d,1H,J=12 Hz), 7.22–7.44 (m,4H)

Starting Material Preparation Example 2

4-(4-Chlorophenyl)-2,3,9-trimethyl-6H-thieno[3,2-f][1,2,4]triazolo[4,3-a][1,4]diazepine (50 g) is dissolved in diethyl carbonate (500 ml) in a nitrogen stream, and 60% sodium hydride is added at room temperature with stirring. After refluxing under heating for 2 hours, the reaction mixture is cooled with ice water, and ethyl bromoacetate (20 ml) is added. After stirring at room temperature for 4 hours, the reaction mixture is poured on a cool 5% aqueous solution of acetic acid, and extracted with chloroform. After washing with water, the extract is dried over anhydrous magnesium sulfate, and filtered. The filtrate is concentrated under reduced pressure, and the residue is subjected to silica gel column chromatography. The objective fraction is concentrated under reduced pressure, and obtained crystals (95 g) are suspended in ethanol (910 ml). The suspension is stirred at 5° C. under ice-cooling, and a 1N aqueous solution of sodium hydroxide (570 ml) is added. After stirring at room temperature for 7 hours, the resulting mixture is neutralized with acetic acid (90 ml), and concentrated under reduced pressure. The obtained crude crystals are recrystallized from a mixed solvent of ethanol (400 ml)-water (250 ml) to give 71 g of (±)-4-(4-chlorophenyl)-6-ethoxycarbonyl-2,3,9-trimethyl-6H-thieno[3,2-f][1,2,4]-triazolo[4,3-a][1,4]diazepine-6-acetic acid, melting point 198°–202° C.

Starting Material Preparation Example 3

Ethanol (500 ml) is added to (±)-4-(4-chlorophenyl)-6-ethoxycarbonyl-2,3,9-trimethyl-6H-thieno[3,2-f][1,2,4]triazolo-[4,3-a][1,4]diazepine-6-acetic acid (43 g), and the mixture is stirred at room temperature. 2N Sodium hydroxide (182 ml) is added and the mixture is stirred at 50° C. overnight. After the completion of the reaction, ethanol is distilled away, and the residue is adjusted to pH 4–5 with acetic acid. Then, the resulting mixture is stirred at 60° C. for 30 minutes and cooled to room temperature. The mixture is extracted with chloroform, and the organic layer is washed with saturated brine. The layer is dried over anhydrous magnesium sulfate and concentrated under reduced pressure. The obtained crystals are recrystallized from chloroform-methanol to give 20 g of (±)-4-(4-chlorophenyl)-2,3,9-trimethyl-6H-thieno[3,2-f][1,2,4]triazolo-[4,3-a][1,4]diazepine-6-acetic acid, melting point 287°–290° C.

Starting Material Preparation Example 4

(±)-4-(4-Chlorophenyl)-6-ethoxycarbonyl-2,3,9-trimethyl-6H-thieno[3,2-f][1,2,4]triazolo[4,3-a][1,4]diazepine-6-acetic acid (82 g) and cinchonidine (50 g) are thoroughly dissolved in methanol (1 l), and the solvent is distilled away to give an amorphous product. Ethyl acetate (980 ml) is added and the amorphous product is dissolved in a similar way. The mixture is left standing overnight at room temperature, and a salt precipitated is removed by filtering by suction. The solvent is distilled away from the filtrate (S-isomer 76% ee) under reduced pressure, and chloroform (500 ml) is added to the residue. The mixture is washed twice with 10% hydrochloric acid, and the organic layer is dried over anhydrous magnesium sulfate and concentrated under reduced pressure. Ethyl acetate (3720 ml) is added to the residue (62 g), and the residue is completely dissolved. The resulting mixture is left standing overnight at room temperature, and a precipitated racemate is removed by filtering by suction. The solvent is distilled away under reduced pressure from the filtrate, and ethanol (500 ml) is added to the residue (43 g) (94% ee). A 2N aqueous solution (182 ml) of sodium hydroxide is added at room temperature with stirring, and the mixture is stirred at 50° C. overnight. After the completion of the reaction, ethanol is distilled away, and the resulting mixture is adjusted to pH 4 with acetic acid. The mixture is stirred at 60° C. for 30 minutes. The reaction mixture is extracted with chloroform, and the organic layer is washed with saturated brine and dried over anhydrous magnesium sulfate. After the solvent is distilled away, ethanol (1920 ml) is added to the residue (32 g) (92% ee) and the mixture is stirred. The insoluble racemate is removed by filtering by suction, and the solvent is distilled away under reduced pressure from the filtrate. The residue is crystallized from chloroform to give an S-isomer [(S)-4-(4-chlorophenyl)-2,3,9-trimethyl-6H-thieno[3,2-f][1,2,4]triazolo[4,3-a][1,4]diazepine-6-acetic acid](20 g) as white powdery crystals (>99% ee). An R-isomer [(R)-4-(4-chlorophenyl)-2,3,9-trimethyl-6H-thieno[3,2-f][1,2,4]triazolo[4,3-a][1,4]diazepine-6-acetic acid], melting point 166–177° C., is obtained by similarly treating the crystals precipitated as a cinchonidine salt.

Optical purity (ee) is determined by HLPC under the following conditions:

Determining conditions column used . . . Ultron ES-OVM (analytical column)

mobile phase . . .

1/15 aqueous potassium dihydrogenphosphate solution:

1/15 aqueous disodium hydrogenphosphate solution: acetonitrile =333:500:120 flow rate . . . 1 ml/minute

Retention time . . . about 4.5 minutes (S-isomer) about 5.5 minutes (R-isomer)

Starting Material Preparation Example 5

(±)-4-(4-Chlorophenyl)-6-ethoxycarbonyl-2,3,9-trimethyl-6H-thieno[3,2-f][1,2,4]triazolo[4,3-a][1,4]diazepine-6-acetic acid (2.0 g) is dissolved in dimethylformamide (20 ml). 1-Hydroxybenzotriazole (HOBt, 0.81 g), N-dimethylaminopropyl-N'-ethylcarbodiimide hydrochloride (WSC, 1.10 g) and triethyl amine (0.77 ml) are added in order under ice-cooling, and the mixture is stirred. Ten minutes later, a solution of 2-methoxyaniline (0.65 g) dissolved in dimethylformamide (6 ml) is dropwise added to the reaction mixture, and the mixture is stirred at room temperature overnight. The reaction mixture is poured into water and extracted with toluene. The organic layer is washed with a 10% aqueous solution of hydrochloric acid, an aqueous solution of sodium hydrogencarbonate and brine, and dried over anhydrous magnesium sulfate. After removing the solvent, the residue is recrystallized from ethanol to give 1.55 g of (±)-ethyl 4-(4-chlorophenyl)-6-(2-methoxyanilino)-carbonylmethyl- 2,3,9-trimethyl-6H-thieno[3,2-f][1,2,4]triazolo[4, 3-a][1,4]diazepine-6-carboxylate. ½ hydrate, melting point 136°–138° C.

The following compounds are obtained in the same manner as in Starting Material Preparation Example 5.

Starting Material Preparation Example 6

(±)-Ethyl 4-(4-chlorophenyl)-6-(3-pyridylamino) carbonylmethyl-2,3,9-trimethyl-6H-thieno[3,2-f][1,2,4] triazolo[4,3-a][1,4]-diazepine-6-carboxylate. 2 hydrate, melting point 133°–135° C.

Starting Material Preparation Example 7

(±)-Ethyl 4-(4-chlorophenyl)-6-morpholinocarbonylmethyl-2,3,9-trimethyl-6H-thieno[3,2-f][1,2,4]triazolo[4,3-a][1,4]diazepine-6-carboxylate. 1/4 hydrate, melting point 184°–186° C.

Starting Material Preparation Example 8

(±)-Ethyl 4-(4-chlorophenyl)-6-piperidinocarbonylmethyl-2,3,9-trimethyl-6H-thieno[3,2-f][1,2,4]triazolo[4,3-a][1,4]diazepine-6-carboxylate, melting point 231°–233° C.

Starting Material Preparation Example 9

(±)-Ethyl 4-(4-chlorophenyl)-6-[4-(2-hydroxyethyl) piperazin-1-yl]carbonylmethyl-2,3,9-trimethyl-6H-thieno [3,2-f][1,2,4]-triazolo[4,3-a][1,4]diazepine-6-carboxylate, melting point 197°–200° C.

EXAMPLE 1

(S)-4-(4-Chlorophenyl)-2,3,9-trimethyl-6H-thieno[3,2-f] -[1,2,4]triazolo[4,3-a][1,4]diazepine-6-acetic acid (7.0 g) and triethylamine (2.73 ml) are added to a mixed solvent of dimethylformamide (70 ml) and tetrahydrofuran (30 ml). The mixture is cooled to –5° C., and pivaloyl chloride (2.38 ml) is dropwise added at said temperature. Ten minutes later, a solution of methylamine (0.69 g) in dimethylformamide (5 ml) is dropwise added at said temperature, and the mixture is stirred at room temperature for 2 hours. Water is added to the reaction mixture, and the mixture is extracted with ethyl acetate, washed with water and dried over anhydrous magnesium sulfate. The solvent is distilled away, and the residue is recrystallized from water/methanol to give 2.29 g of (S)-N-methyl-4-(4-chloro-phenyl)-2,3,9-trimethyl-6H-thieno[3,2-f][1,2,4]triazolo[4,3-a]-[1,4]diazepine-6-acetamide 1/4 hydrate, melting point 143°–145° C.

$[\alpha]_D^{26}$=+18.4° (c=1 methanol)

EXAMPLE 2

(S)-4-(4-Chlorophenyl)-2,3,9-trimethyl-6H-thieno[3,2-f] -[1,2,4]triazolo[4,3-a][1,4]diazepine-6-acetic acid (7.0 g) and triethylamine (2.73 ml) are added to a mixed solvent of dimethylformamide (70 ml) and tetrahydrofuran (30 ml). The mixture is cooled to –5° C., and pivaloyl chloride (2.38 ml) is dropwise added at said temperature. Ten minutes later, a solution of ethanolamine (1.17 g) in tetrahydrofuran (10 ml) is dropwise added at said temperature, and the mixture is stirred at room temperature for 2 hours. Water is added to the reaction mixture, and the mixture is extracted with ethyl acetate, washed with water and dried over anhydrous magnesium sulfate. The solvent is distilled away, and the residue is purified by column chromatography (chloroform: methanol =50: 1) and recrystallized from ethyl acetate to give 2.29 g of (S)-N-(2-hydroxyethyl)-4-(4-chlorophenyl)-2,3,9-trimethyl-6H-thieno[3,2-f][1,2,4]triazolo[4,3-a][1,4] diazepine-6-acetamide 1/4 hydrate, melting point 254°–255° C.

$[\alpha]_D^{26}$=+24.9° (c=1 methanol)

EXAMPLE 3

(S)-4-(4-Chlorophenyl)-2,3,9-trimethyl-6H-thieno[3,2-f] -[1,2,4]triazolo[4,3-a][1,4]diazepine-6-acetic acid (3.0 g) and triethylamine (1.2 ml) are added to a mixed solvent of dimethylformamide (30 ml) and tetrahydrofuran (15 ml). The mixture is cooled to -10° C., and pivaloyl chloride (1.0 ml) is dropwise added at said temperature. Thirty minutes later, a solution of 4-aminophenol (0.99 g) in dimethylformamide (20 ml) is dropwise added at said temperature, and the mixture is stirred at room temperature for 7.5 hours. After the completion of the reaction, tetrahydrofuran is distilled away, and saturated brine (200 ml) is added. The mixture is extracted with ethyl acetate, and the organic layer is washed with saturated brine, dried over anhydrous magnesium sulfate and concentrated under reduced pressure. The residue is purified by silica gel column chromatography (ethyl acetate: methanol=10:1) and crystallized from isopropyl alcohol to give 620 mg of (S)-N-(4-hydroxyphenyl)-4-(4-chlorophenyl)-2,3,9-trimethyl-6H-thieno[3,2-f][1,2,4] triazolo[4,3-a][1,4]diazepine-6-acetamide as pale-pink powdery crystals, melting point 215°–220° C.

EXAMPLE 4

(S)-4-(4-Chlorophenyl)-2,3,9-trimethyl-6H-thieno[3,2-f] -[1,2,4]triazolo[4,3-a][1,4]diazepine-6-acetic acid (3.0 g), triethylamine (1.56 ml) and p-phenylenediamine (0.97 g) are dissolved in dimethylformamide (30 ml). Benzotriazol-1-yl-oxy-tris(dimethyl)phosphonium hexafluorophosphate (3.6 g) is added, and the mixture is stirred at room temperature for 12 hours. After the completion of the reaction, water (200 ml) is added, and the mixture is extracted with ethyl acetate. The extract is washed with saturated brine and dried over anhydrous magnesium sulfate. After the solvent is distilled away under reduced pressure, the residue is subjected to silica gel column chromatography and obtained crystals are recrystallized from toluene to give 0.56 g of (S)-N-(4-aminophenyl)-4-(4-chlorophenyl)-2,3,9-trimethyl-6H-thieno[3,2-f][1,2,4]triazolo[4, 3-a][1,4]diazepine-6-acetamide, melting point 169°–173° C.

EXAMPLE 5

(S)-(4-Chlorophenyl)-2,3,9-trimethyl-6H-thieno[3,2-f]-[1,2,4]triazolo[4,3-a][1,4]diazepine-6-acetic acid (2.64 g) is dissolved in dimethylformamide (30 ml). N-Dimethylaminopropyl-N'-ethylcarbodiimide hydrochloride (1.51 g) and triethylamine (1.08 ml) are added in order and the mixture is stirred. Five minutes later, 3-aminopyridine (0.66 g) is added to the reaction mixture and the mixture is stirred at room temperature overnight. The reaction mixture is poured into water, and the obtained crystals are purified by column chromatography (chloroform: methanol =50: 1). The crystals are converted to hydrochloride with ethanol/hydrochloric acid in ethyl acetate, and recrystallized from ethanol/ethyl acetate to give 0.88 g of (S)-N-(3-pyridyl)-4-(4-chlorophenyl)-2,3,9-trimethyl-6H-thieno[3,2-f][1,2,4]triazolo[4,3-a][1,4] diazepine-6-acetamide hydrochloride, melting point 198°–201° C.

$[\alpha]_D^{25}$=–22.6° (c=1 methanol)

The following compounds are produced in the same manner as in the above Examples.

EXAMPLE 6

(S)-N-Carbamoylmethyl-4-(4-chlorophenyl)-2,3,9-trimethyl-6H-thieno[3,2-f][1,2,4]triazolo[4,3-a][1,4]diazepine-6-acetamide $^1$H-NMR 270 MHz($CDCl_3$)δ: 1.68 (s,3H), 2.56 (s,3H), 2.67 (s,3H), 3.50 (m,2H), 3.77 (dd, 1H), 4.19 (dd,1H), 4.67 (t,1H), 5.69 (br.s,1H), 7.30 (br.s,1H), 7.37 (dd,4H), 8.00 (t,1H)

EXAMPLE 7

(S)-N-(2-Methoxy-3-pyridyl)-4-(4-chlorophenyl)-2,3,9-trimethyl-6H-thieno[3,2-f][1,2,4]triazolo[4,3-a][1,4]diazepine-6-acetamide $^1$H-NMR 270 MHz($CDCl_3$)δ: 1.69 (s,3H), 2.41 (s,3H), 2.68 (s,3H), 3.66 (m,2H), 4.00 (s,1H), 4.65 (t,H), 6.88 (dd,1H), 7.39 (dd,4H), 7.85 (dd,1H), 8.60 (dd,1H), 8.67 (br.s,1H)

EXAMPLE 8

(S)-N-(4-Methoxy-3-pyridyl)-4-(4-chlorophenyl)-2,3,9-trimethyl-6H-thieno[3,2-f][1,2,4]triazolo[4,3-a][1,4]diazepine-6-acetamide, melting point 281°–283° C.

EXAMPLE 9

(S)-(−)-N-Methoxy-4-(4-chlorophenyl)-2,3,9-trimethyl-6H-thieno[3,2-f][1,2,4]triazolo[4,3-a][1,4]diazepine-6-acetamide 1/4 hydrate, melting point 230°–231° C.

$[\alpha]_D^{26}$=+13.7° (c=1.0 methanol)

EXAMPLE 10

(S)-N-bis(Hydroxymethyl)methyl-4-(4-chlorophenyl)-2,3,9-trimethyl-6H-thieno[3,2-f][1,2,4]triazolo[4,3-a][1,4]diazepine-6-acetamide $^1$H-NMR 270 MHz($CDCl_3$)δ: 1.68 (3H,s), 2.41 (3H,s), 2.65 (3H,s), 3.34 (1H,dd,J=14.52 and 4.62 Hz), 3.62–4.10 (8H,m), 4.72 (1H,dd,J=9.24 and 4.62 Hz), 7.32 (2H,d,J=8.58 Hz), 7.41 (2H,d, J=8.58 Hz), 7.58 (1H,d,J=7.92 Hz)

EXAMPLE 11

(R)-4-(4-Chlorophenyl)-2,3,9-trimethyl-6H-thieno[3,2-f][1,2,4]triazolo[4,3-a][1,4]diazepine-6-acetic acid is subjected to the reactions similar to those in the above Example 2 to give (R)-N-(2-hydroxyethyl)-4-(4-chlorophenyl)-2,3,9-trimethyl-6H-thieno[3,2-f][1,2,4]triazolo[4,3-a][1,4]diazepine-6-acetamide, melting point 255°–257° C.

EXAMPLE 12

(R)-4-(4-Chlorophenyl)-2,3,9-trimethyl-6H-thieno[3,2-f][1,2,4]triazolo[4,3-a][1,4]diazepine-6-acetic acid is subjected to the reactions similar to those in the above Example 1 to give (R)-N-methyl-4-(4-chlorophenyl)-2,3,9-trimethyl-6H-thieno[3,2-f][1,2,4]triazolo[4,3-a][1,4]diazepine-6-acetamide 1/4 hydrate, melting point 188°–190° C.

EXAMPLE 13

(±)-4-(4-Chlorophenyl)-2,3,9-trimethyl-6H-thieno[3,2-f][1,2,4]triazolo[4,3-a][1,4]diazepine-6-acetic acid (1.7 g) and triethylamine (0.65 ml) are added to a mixed solvent of dimethylformamide (20 ml) and tetrahydrofuran (10 ml). The mixture is cooled to −5° C. and pivaloyl chloride (0.57 ml) is dropwise added at said temperature. Ten minutes later, a solution of 4-aminopyridine (0.43 g) in dimethylformamide (2 ml) and tetrahydrofuran (2 ml) is dropwise added at said temperature, and the mixture is stirred at room temperature for 2 hours. Water is added to the reaction mixture, and the mixture is extracted with ethyl acetate, washed with water and dried over anhydrous magnesium sulfate. The solvent is distilled away and the residue is recrystallized from isopropyl alcohol/isopropyl ether to give 1.29 g of (±)-N-(4-pyridyl)-4-(4-chlorophenyl)-2,3,9-trimethyl-6H-thieno[3,2-f][1,2,4]triazolo-[4,3-a][1,4]diazepine-6-acetamide, melting point 237°–239° C.

EXAMPLE 14

(±)-4-(4-Chlorophenyl)-2,3,9-trimethyl-6H-thieno[3,2-f][1,2,4]triazolo[4,3-a][1,4]diazepine-6-acetic acid (1.0 g), 2-aminopyrimidine (0.28 g) and pyridine (0.49 ml) are added to dichloroethane (15 ml), and the mixture is stirred in an ice bath. A solution of 2-chloro-1,3-dimethylimidazolium chloride (0.63 g) in dichloroethane (12 ml) is dropwise added to this mixture at a temperature of not more than 5° C. The mixture is stirred at room temperature overnight, and the reaction mixture is washed with water and dried over anhydrous magnesium sulfate. The solvent is distilled away and the residue is purified by column chromatography (chloroform:methanol=20:1) and recrystallized from ethanol to give 0.78 g of (±)-N-(2-pyrimidinyl)-4-(4-chlorophenyl)-2,3,9-trimethyl-6H-thieno[3,2-f][1,2,4]triazolo[4,3-a][1,4]diazepine-6-acetamide, melting point 251°–253° C.

EXAMPLE 15

(±)-4-(4-Chlorophenyl)-2,3,9-trimethyl-6H-thieno[3,2-f][1,2,4]triazolo[4,3-a][1,4]diazepine-6-acetic acid (1.0 g) and benzotriazol-1-yl-oxy-tris(dimethylamino)phosphonium hexafluorophosphate (1.2 g) are added to dimethylformamide (20 ml), and the mixture is stirred. 3-(Aminomethyl) pyridine (0.30 g) and triethylamine (0.38 g) are added, and the mixture is stirred at room temperature for 6 hours. After the completion of the reaction, water (200 ml) is added and the mixture is extracted with ethyl acetate. The organic layer is washed with saturated brine, dried over anhydrous magnesium sulfate and concentrated under reduced pressure. The residue is crystallized from ethyl acetate and isopropyl ether, and recrystallized from ethanol to give 200 mg of (±)-N-(3-pyridylmethyl)-4-(4-chlorophenyl)-2,3,9-trimethyl-6H-thieno[3,2-f][1,2,4]triazolo[4,3-a][1,4]diazepine-6-acetamide 1/2 1759 hydrate as white powdery crystals, melting point 180°–183° C.

In the same manner as in Examples 13 or 14, the following compounds are obtained.

EXAMPLE 16

(±)-N-Phenyl-4-(4-chlorophenyl)-2,3,9-trimethyl-6H-thieno[3,2-f][1,2,4]triazolo[4,3-a][1,4]diazepine-6-acetamide, melting point 260°–262° C. (decomposition)

EXAMPLE 17

(±)-N-Benzyl-4-(4-chlorophenyl)-2,3,9-trimethyl-6H-thieno[3,2-f][1,2,4]triazolo[4,3-a][1,4]diazepine-6-acetamide, melting point 233°–235° C. (decomposition)

EXAMPLE 18

(±)-N-(2-Phenylethyl)-4-(4-chlorophenyl)-2,3,9-trimethyl-6H-thieno[3,2-f][1,2,4]triazolo[4,3-a][1,4]

diazepine-6-acetamide, melting point 272°–274° C. (decomposition)

EXAMPLE 19

(±)-N-(1-Benzylpiperidin-4-yl)-4-(4-chlorophenyl)-2,3,9-trimethyl-6H-thieno[3,2-f][1,2,4]triazolo[4,3-a][1,4]diazepine-6-acetamide, melting point 228°–230° C. (decomposition)

EXAMPLE 20

(±)-N-Cyclohexyl-4-(4-chlorophenyl)-2,3,9-trimethyl-6H-thieno[3,2-f][1,2,4]triazolo[4,3-a][1,4]diazepine-6-acetamide, melting point 270°–272° C. (decomposition)

EXAMPLE 21

(±)-N-Propyl-4-(4-chlorophenyl)-2,3,9-trimethyl-6H-thieno[3,2-f][1,2,4]triazolo[4,3-a][1,4]diazepine-6-acetamide, melting point 216°–218° C.

EXAMPLE 22

(±)-4-[2-(4-(4-chlorophenyl)-2,3,9-trimethyl-6H-thieno[3,2-f][1,2,4]triazolo[4,3-a][1,4]diazepin-6-yl)acetyl]thiomorpholine, melting point 180°–182° C. (decomposition)

EXAMPLE 23

(±)-N-(2-Dimethylaminoethyl)-4-(4-chlorophenyl)-2,3,9-trimethyl-6H-thieno[3,2-f][1,2,4]triazolo[4,3-a][1,4]diazepine-6-acetamide, melting point 210°–212° C.

EXAMPLE 24

(±)-N-Methyl-4-(4-chlorophenyl)-2,3,9-trimethyl-6H-thieno[3,2-f][1,2,4]triazolo[4,3-a][1,4]diazepine-6-acetamide 1/2 hydrate, melting point 146°–148° C.

EXAMPLE 25

(±)-N,N-Dimethyl-4-(4-chlorophenyl)-2,3,9-trimethyl-6H-thieno[3,2-f][1,2,4]triazolo[4,3-a][1,4]diazepine-6-acetamide, melting point 229°–230° C.

EXAMPLE 26

(±)-N-(2-Pyridyl)-4-(4-chlorophenyl)-2,3,9-trimethyl-6H-thieno[3,2-f][1,2,4]triazolo[4,3-a][1,4]diazepine-6-acetamide, melting point 267°–270° C. (decomposition)

EXAMPLE 27

(±)-1-[2-(4-(4-Chlorophenyl)-2,3,9-trimethyl-6H-thieno[3,2-f][1,2,4]triazolo[4,3-a][1,4]diazepin-6-yl)acetyl]-4-methylpiperazine, melting point 208°–210° C.

EXAMPLE 28

(±)-4–14-Chlorophenyl)-2,3,9-trimethyl-6H-thieno[3,2-f][1,2,4]triazolo[4,3-a][1,4]diazepine-6-acetamide, melting point 282°–284° C. (decomposition)

EXAMPLE 29

(±)-N-(2-Hydroxyethyl)-4-(4-chlorophenyl)-2,3,9-trimethyl-6H-thieno[3,2-f][1,2,4]triazolo[4,3-a][1,4]diazepine-6-acetamide 1/2 hydrate, melting point 140°–143° C.

EXAMPLE 30

(±)-Ethyl [2-(4-(4-chlorophenyl)-2,3,9-trimethyl-6H-thieno[3,2-f][1,2,4]triazolo[4,3-a][1,4]diazepin-6-yl)-acetamide]acetate, melting point 117°–120° C.

EXAMPLE 31

(±)-3-Amino-1-[2-(4-(4-chlorophenyl)-2,3,9-trimethyl-6H-thieno[3,2-f][1,2,4]triazolo[4,3-a][1,4]diazepin-6-yl)-acetyl]pyrazole, melting point 246°–248° C. (decomposition)

EXAMPLE 32

(±)-4-Benzyl-1-[2-(4-(4-chlorophenyl)-2,3,9-trimethyl-6H-thieno[3,2-f][1,2,4]triazolo[4,3-a][1,4]diazepin-6-yl)-acetyl]piperidine, melting point 149°–151° C.

EXAMPLE 33

(±)-N-(4-Methyl-2-pyridyl)-4-(4-chlorophenyl)-2,3,9-trimethyl-6H-thieno[3,2-f][1,2,4]triazolo[4,3-a][1,4]diazepine-6-acetamide, melting point 279°–280° C. (decomposition)

EXAMPLE 34

(±)-N-(3-Hydroxyphenyl)-4-(4-chlorophenyl)-2,3,9-trimethyl-6H-thieno[3,2-f][1,2,4]triazolo[4,3-a][1,4]diazepine-6-acetamide methanol, melting point 193°–195° C.

EXAMPLE 35

(±)-N-(4-Hydroxyphenyl)-4-(4-chlorophenyl)-2,3,9-trimethyl-6H-thieno[3,2-f][1,2,4]triazolo[4,3-a][1,4]diazepine-6-acetamide 1/4 methanol, melting point 296°–298° C. (decomposition)

EXAMPLE 36

(±)-N-(3-Aminophenyl)-4-(4-chlorophenyl)-2,3,9-trimethyl-6H-thieno[3,2-f][1,2,4]triazolo[4,3-a][1,4]diazepine-6-acetamide, melting point 266°–268° C. (decomposition)

EXAMPLE 37

(±)-N-(4-Aminophenyl)-4-(4-chlorophenyl)-2,3,9-trimethyl-6H-thieno[3,2-f][1,2,4]triazolo[4,3-a][1,4]diazepine-6-acetamide monohydrate, melting point 164°–166° C.

EXAMPLE 38

(±)-N-Carbamoylmethyl-4-(4-chlorophenyl)-2,3,9-trimethyl-6H-thieno[3,2-f][1,2,4]triazolo[4,3-a][1,4]diazepine-6-acetamide monohydrate, melting point 167°–170° C.

EXAMPLE 39

(±)-N-(3-Hydroxy-2-pyridyl)-4-(4-chlorophenyl)-2,3,9-trimethyl-6H-thieno[3,2-f][1,2,4]triazolo[4,3-a][1,4]diazepine-6-acetamide 1/4 hydrate, melting point 253°–255° C. (decomposition)

EXAMPLE 40

(±)-N-Ethyl-4-(4-chlorophenyl)-2,3,9-trimethyl-6H-thieno[3,2-f][1,2,4]triazolo[4,3-a][1,4]diazepine-6-acetamide, melting point 158° C.

EXAMPLE 41

(±)-N-(4-Hydroxybutyl)-4-(4-chlorophenyl)-2,3,9-trimethyl-6H-thieno[3,2-f][1,2,4]triazolo[4,3-a][1,4]diazepine-6-acetamide 1/4 hydrate, melting point 226° C.

EXAMPLE 42

(±)-N-(3-Carbamoylphenyl)-4-(4-chlorophenyl)-2,3,9-trimethyl-6H-thieno[3,2-f][1,2,4]triazolo[4,3-a][1,4]diazepine-6-acetamide, melting point 220°–222° C.

EXAMPLE 43

(±)-N-(6-Hydroxyhexyl)-4-(4-chlorophenyl)-2,3,9-trimethyl-6H-thieno[3,2-f][1,2,4]triazolo[4,3-a][1,4]diazepine-6-acetamide, melting point 203° C.

EXAMPLE 44

(±)-4-(4-Chlorophenyl)-2,3,9-trimethyl-6H-thieno[3,2-f][1,2,4]triazolo[4,3-a][1,4]diazepine-6-acetohydroxamic acid, melting point 225°–226° C. (decomposition)

EXAMPLE 45

(±)-N-(3-Quinolyl)-4-(4-chlorophenyl)-2,3,9-trimethyl-6H-thieno[3,2-f][1,2,4]triazolo[4,3-a][1,4]diazepine-6-acetamide, melting point 268°–270° C.

EXAMPLE 46

(±)-N-(2-Thiazolyl)-4-(4-chlorophenyl)-2,3,9-trimethyl-6H-thieno[3,2-f][1,2,4]triazolo[4,3-a][1,4]diazepine-6-acetamide, melting point 276°–278° C.

EXAMPLE 47

(±)-N-(1-Isoquinolyl)-4-(4-chlorophenyl)-2,3,9-trimethyl-6H-thieno[3,2-f][1,2,4]triazolo[4,3-a][1,4]diazepine-6-acetamide, melting point 250°–252° C.

EXAMPLE 48

(±)-Ethyl 4-(4-chlorophenyl)-6-(2-methoxyanilino)-carbonylmethyl-2,3,9-trimethyl-6H-thieno[3,2-f][1,2,4]triazolo-[4,3-a][1,4]diazepine-6-carboxylate 1/2 hydrate (1.55 g) obtained in Starting Material Preparation Example 5 is suspended in ethanol (16 ml). 1N Sodium hydroxide (5.4 ml) is added and the mixture is stirred at room temperature overnight. The solvent is distilled away and the residue is dissolved in water (15 ml). Acetic acid (1.5 ml) is added and the mixture is stirred at room temperature for 1 hour. The resulting crystals are collected by filtration and recrystallized from aqueous ethanol to give 0.89 g of (±)-N-(2-methoxyphenyl)-4-(4-chlorophenyl)-2,3,9-trimethyl-6H-thieno[3,2-f][1,2,4]-triazolo[4,3-a][1,4]diazepine-6-acetamide 1/2 hydrate, melting point 119°–121° C.

EXAMPLE 49

(±)-Ethyl 4-(4-chlorophenyl)-6-(3-pyridylamino)carbonyl-methyl-2,3,9-trimethyl-6H-thieno[3,2-f][1,2,4]triazolo[4,3-a]-[1,4]diazepine-6-carboxylate 2 hydrate as obtained in Starting Material Preparation Example 6 is treated in the same manner as in Example 48 to give (±)-N-(3-pyridyl)-4-(4-chlorophenyl)-2,3,9-trimethyl-6H-thieno[3,2-f][1,2,4]triazolo[4,3-a][1,4]-diazepine-6-acetamide 1/2 hydrate, melting point 164°–167° C.

EXAMPLE 50

(±)-Ethyl 4-(4-chlorophenyl)-6-morpholinocarbonylmethyl-2,3,9-trimethyl-6H-thieno[3,2-f][1,2,4]triazolo[4,3-a][1,4]diazepine-6-carboxylate 1/4 hydrate as obtained in Starting Material Preparation Example 7 is treated in the same manner as in Example 48 to give (±)-4-[2-(4-(4-chlorophenyl)-2,3,9-trimethyl-6H-thieno[3,2-f][1,2,4]triazolo[4,3-a][1,4]-diazepin-6-yl)acetyl]morpholine, melting point 252°–254° C.

EXAMPLE 51

(±)-Ethyl 4-(4-chlorophenyl)-6-piperidinocarbonylmethyl-2,3,9-trimethyl-6H-thieno[3,2-f][1,2,4]triazolo[4,3-a][1,4]diazepine-6-carboxylate as obtained in Starting Material Preparation Example 8 is treated in the same manner as in Example 48 to give (±)-1-(2-(4-(4-chlorophenyl)-2,3,9-trimethyl-6H-thieno[3,2-f][1,2,4]triazolo[4,3-a][1,4]diazepin-6-yl)acetyl)piperidine, melting point 260°–262° C.

EXAMPLE 52

(±)-Ethyl 4-(4-chlorophenyl)-6-[4-(2-hydroxyethyl)-piperazin-1-yl]carbonylmethyl-2,3,9-trimethyl-6H-thieno[3,2-f][1,2,4]triazolo[4,3-a][1,4]diazepine-6-carboxylate as obtained in Starting Material Preparation Example 9 is treated in the same manner as in Example 48 to give (±)-4-(2-hydroxyethyl)-1-(4-(4-chlorophenyl)-2,3,9-trimethyl-6H-thieno[3,2-f][1,2,4]triazolo[4,3-a][1,4]diazepin-6-yl)acetylpiperazine, melting point 227°–219° C.

In the same manner as above, the following compounds are obtained.

EXAMPLE 53

(±)-N-Allyl-4-(4-chlorophenyl)-2,3,9-trimethyl-6H-thieno[3,2-f][1,2,4]triazolo[4,3-a][1,4]diazepine-6-acetamide, melting point 204°–206° C.

EXAMPLE 54

(±)-N-(2-Imidazolyl)-4-(4-chlorophenyl)-2,3,9-trimethyl-6H-thieno[3,2-f][1,2,4]triazolo[4,3-a][1,4]diazepine-6-acetamide 1/4 hydrate, melting point not less than 300° C.

EXAMPLE 55

(±)-3-Amino-1-[2-(4-(4-chlorophenyl)-2,3,9-trimethyl-6H-thieno[3,2-f][1,2,4]triazolo[4,3-a][1,4]diazepin-6-yl)acetyl]-1H-1,2,4-triazole, melting point 292°–294° C. (decomposition)

EXAMPLE 56

(±)-N-(4-Methylpiperazin-1-yl)-4-(4-chlorophenyl)-2,3,9-trimethyl-6H-thieno[3,2-f][1,2,4]triazolo[4,3-a][1,4]diazepine-6-acetamide 1/4 hydrate, melting point 270°–273° C. (decomposition)

EXAMPLE 57

(±)-N-(3-Dimethylaminopropyl)-4-(4-chlorophenyl)-2,3,9-trimethyl-6H-thieno[3,2-f][1,2,4]triazolo[4,3-a][1,4]diazepine-6-acetamide, melting point 207°–209° C.

EXAMPLE 58

(±)-N,N-Diethyl-4-(4-chlorophenyl)-2,3,9-trimethyl-6H-thieno[3,2-f][1,2,4]triazolo[4,3-a][1,4]diazepine-6-acetamide, melting point 210°–211° C.

EXAMPLE 59

(±)-N-Phenyl-4-(2-chlorophenyl)-2-ethyl-9-methyl-6H-thieno[3,2-f][1,2,4]triazolo[4,3-a][1,4]diazepine-6-acetamide, melting point 272° C.

EXAMPLE 60

(±)-N-(3-Methylphenyl)-4-(2-chlorophenyl)-2-ethyl-9-methyl-6H-thieno[3,2-f][1,2,4]triazolo[4,3-a][1,4]diazepine-6-acetamide, melting point 200° C.

EXAMPLE 61

(±)-N-(2-Methylphenyl)-4-(4-chlorophenyl)-2-ethyl-9-methyl-6H-thieno[3,2-f][1,2,4]triazolo[4,3-a][1,4]diazepine-6-acetamide 1/4 hydrate, melting point 278°–280° C.

EXAMPLE 62

(±)-N-(4-Methylphenyl)-4-(4-chlorophenyl)-2-ethyl-9-methyl-6H-thieno[3,2-f][1,2,4]triazolo[4,3-a][1,4]diazepine-6-acetamide 1/4 hydrate, melting point 306°–308° C.

EXAMPLE 63

(±)-N-(2-Chlorophenyl)-4-(4-chlorophenyl)-2-ethyl-9-methyl-6H-thieno[3,2-f][1,2,4]triazolo[4,3-a][1,4]diazepine-6-acetamide, melting point 226°–228° C.

EXAMPLE 64

(±)-N-(4-Chlorophenyl)-4-(4-chlorophenyl)-2-ethyl-9-methyl-6H-thieno[3,2-f][1,2,4]triazolo[4,3-a][1,4]diazepine-6-acetamide, melting point 315°–317° C.

EXAMPLE 65

(±)-N-(4-Methoxyphenyl)-4-(4-chlorophenyl)-2-ethyl-9-methyl-6H-thieno[3,2-f][1,2,4]triazolo[4,3-a][1,4]diazepine-6-acetamide, melting point 260°–262° C.

EXAMPLE 66

(±)-N-(3-Trifluoromethylphenyl)-4-(4-chlorophenyl)-2-ethyl-9-methyl-6H-thieno[3,2-f][1,2,4]triazolo[4,3-a][1,4]diazepine-6-acetamide, melting point 243°–245° C.

EXAMPLE 67

(±)-N-Cyclohexyl-4-(4-chlorophenyl)-2-ethyl-9-methyl-6H-thieno[3,2-f][1,2,4]triazolo[4,3-a][1,4]diazepine-6-acetamide 1/4 hydrate, melting point 261°–263° C.

EXAMPLE 68

(±)-N-(3-Pyridyl)-4-(4-chlorophenyl)-2-ethyl-9-methyl-6H-thieno[3,2-f][1,2,4]triazolo[4,3-a][1,4]diazepine-6-acetamide 1/4 hydrate, melting point 250°–252° C.

EXAMPLE 69

(±)-N-(4-Pyridyl)-4-(4-chlorophenyl)-2-ethyl-9-methyl-6H-thieno[3,2-f][1,2,4]triazolo[4,3-a][1,4]diazepine-6-acetamide 1/4 hydrate, melting point 287°–289° C.

EXAMPLE 70

(±)-N-(2-Thiazolyl)-4-(4-chlorophenyl)-2-ethyl-9-methyl-6H-thieno[3,2-f][1,2,4]triazolo[4,3-a][1,4]diazepine-6-acetamide, melting point 303°–305° C.

EXAMPLE 71

(±)-N-(2-Benzothiazolyl)-4-(4-chlorophenyl)-2-ethyl-9-methyl-6H-thieno[3,2-f][1,2,4]triazolo[4,3-a][1,4]diazepine-6-acetamide, melting point 301°–303° C.

EXAMPLE 72

(±)-N-(3,5-Dimethoxyphenyl)-4-(4-chlorophenyl)-2-ethyl-9-methyl-6H-thieno[3,2-f][1,2,4]triazolo[4,3-a][1,4]diazepine-6-acetamide, melting point 238°–240° C.

EXAMPLE 73

(±)-1-[2-(4-(4-Chlorophenyl)-2-ethyl-9-methyl-6H-thieno[3,2-f][1,2,4]triazolo[4,3-a][1,4]diazepin-6-yl)acetyl]piperidine, melting point 239°–241° C.

EXAMPLE 74

(±)-N-(2-Pyridyl)-4-(4-chlorophenyl)-2-ethyl-9-methyl-6H-thieno[3,2-f][1,2,4]triazolo[4,3-a][1,4]diazepine-6-acetamide 1/4 hydrate, melting point 255°–257° C.

EXAMPLE 75

(±)-N-(1-Naphthyl)-4-(4-chlorophenyl)-2-ethyl-9-methyl-6H-thieno[3,2-f][1,2,4]triazolo[4,3-a][1,4]diazepine-6-acetamide 1/4 hydrate, melting point 230°–232° C.

EXAMPLE 76

(±)-4-Methyl-1-[2-(4-(4-chlorophenyl)-2-ethyl-9-methyl-6H-thieno[3,2-f][1,2,4]triazolo[4,3-a][1,4]diazepin-6-yl)-acetyl]piperazine $^1$H-NMR 100 MHz($CDCl_3$, ppm) δ: 1.38 (3H,t), 2.38 (3H,s), 2.42–2.58 (4H,m), 2.70 (3H,s), 2.85 (2H,q), 3.61–3.80 (4H,m), 6.61 (1H,s), 7.35 (2H,d), 7.53 (2H,d)

EXAMPLE 77

(±)-1-[2-(4-(4-Chlorophenyl)-2,3,9-trimethyl-6H-thieno[3,2-f][1,2,4]triazolo[4,3-a][1,4]diazepin-6-yl)acetyl]-4-hydroxypiperidine, melting point 249°–250° C.

EXAMPLE 78

(±)-N-Pentyl-4-(4-chlorophenyl)-2,3,9-trimethyl-6H-thieno[3,2-f][1,2,4]triazolo[4,3-a][1,4]diazepine-6-acetamide, melting point 201°–202° C.

EXAMPLE 79

(±)-N-(4-Dimethylaminobutyl)-4-(4-chlorophenyl)-2,3,9-trimethyl-6H-thieno[3,2-f][1,2,4]triazolo[4,3-a][1,4]diazepin-6-acetamide 1/4 hydrate, melting point 132°–135° C.

EXAMPLE 80

(±)-N,N-Dipropyl-4-(4-chlorophenyl)-2,3,9-trimethyl-6H-thieno[3,2-f][1,2,4]triazolo[4,3-a][1,4]diazepine-6-acetamide 1/4 hydrate $^1$H-NMR 270 MHz($CDCl_3$, ppm) δ: 0.90 (3H,t), 0.99 (3H, t), 1.60 (2H,six), 1.67 (3H,s), 1.78 (2H, t), 2.39 (3H,s), 2.66 (3H,s), 3.35 (2H,t), 3.48 (2H,six), 3.62 (2H,dd), 4.83 (1H,t), 7.32 (2H,d), 7.40 (2H,d)

EXAMPLE 81

(±)-N-Pyrazinyl-4-(4-chlorophenyl)-2,3,9-trimethyl-6H-thieno[3,2-f][1,2,4]triazolo[4,3-a][1,4]diazepine-6-acetamide, melting point 250°–252° C.

EXAMPLE 82

(±)-N-(5-Pyrimidinyl)-4-(4-chlorophenyl)-2,3,9-trimethyl-6H-thieno[3,2-f][1,2,4]triazolo[4,3-a][1,4]diazepine-6-acetamide, melting point 268°–270° C.

EXAMPLE 83

(±)-Ethyl 3-[(4-(4-chlorophenyl)-2,3,9-trimethyl-6H-thieno[3,2-f][1,2,4]triazolo[4,3-a][1,4]diazepin-6-yl)-acetamido]benzoate, melting point 232°–234° C.

EXAMPLE 84

(±)-N-Methyl-N-(2-pyridyl)-4-(4-chlorophenyl)-2,3,9-trimethyl-6H-thieno[3,2-f][1,2,4]triazolo[4,3-a][1,4]diazepine-6-acetamide 1/4 hydrate, melting point 220°–223° C.

EXAMPLE 85

(±)-N-(3-Dimethylaminophenyl)-4-(4-chlorophenyl)-2,3,9-trimethyl-6H-thieno[3,2-f][1,2,4]triazolo[4,3-a][1,4]diazepine-6-acetamide 1/4 hydrate, melting point 182°–185° C.

EXAMPLE 86

(±)-N-(3-Pyridazinyl)-4-(4-chlorophenyl)-2,3,9-trimethyl-6H-thieno[3,2-f][1,2,4]triazolo[4,3-a][1,4]diazepine-6-acetamide 1/4 hydrate, melting point 291°–293° C.

EXAMPLE 87

(±)-N-(4-Pyridazinyl)-4-(4-chlorophenyl)-2,3,9-trimethyl-6H-thieno[3,2-f][1,2,4]triazolo[4,3-a][1,4]diazepine-6-acetamide 1/4 hydrate, melting point 253°–256° C.

EXAMPLE 88

(±)-N-Methyl-N-(3-pyridyl)-4-(4-chlorophenyl)-2,3,9-trimethyl-6H-thieno[3,2-f][1,2,4]triazolo[4,3-a][1,4]diazepine-6-acetamide, melting point 202°–204° C.

EXAMPLE 89

(±)-N-(3-Thienyl)-4-(4-chlorophenyl)-2,3,9-trimethyl-6H-thieno[3,2-f][1,2,4]triazolo[4,3-a][1,4]diazepine-6-acetamide, melting point 277°–280° C.

EXAMPLE 90

(±)-N-(2-Dipropylaminoethyl)-4-(4-chlorophenyl)-2,3,9-trimethyl- 6H-thieno[3,2-f][1,2,4]triazolo[4,3-a][1,4]diazepine-6-acetamide, melting point 134°–139° C.

EXAMPLE 91

(±)-Ethyl 3-[2-(4-(4-chlorophenyl)-2,3,9-trimethyl-6H-thieno[3,2-f][1,2,4]triazolo[4,3-a][1,4]diazepin-6-yl)-acetamide]propionate, melting point 177°–179° C.

EXAMPLE 92

(±)-Ethyl 3-[2-(4-(4-chlorophenyl)-2,3,9-trimethyl-6H-thieno[3,2-f][1,2,4]triazolo[4,3-a][1,4]diazepin-6-yl)-acetamide]propionate (1.2 g) obtained in Example 91 is dissolved in ethanol (30 ml). A 1N aqueous solution (4.8 ml) of sodium hydroxide is added and the mixture is stirred at room temperature for 2 hours. The reaction mixture is poured into water (100 ml) and washed with isopropyl ether (20 ml). The aqueous layer is adjusted to pH 3.5 with 1N hydrochloric acid and the resulting crystals are collected by filtration. Recrystallization from isopropyl alcohol affords 0.25 g of (±)-3-[2-(4-(4-chlorophenyl)-2,3,9-trimethyl-6H-thieno[3,2-f][1,2,4]triazolo[4,3-a][1,4]diazepin-6-yl)acetamide]-propionic acid, melting point 231° C.

EXAMPLE 93

(±)-N-(2-(tert-Butoxycarbonylamino)ethyl)-4-(4-chlorophenyl)-2,3,9-trimethyl-6H-thieno[3,2-f][1,2,4]triazolo[4,3-a][1,4]diazepine-6-acetamide, melting point 166°–170° C.

EXAMPLE 94

Hydrogen chloride is blown in a mixture of the compound of Example 93 (1.0 g) and ethyl acetate (ca. 30 ml) under ice-cooling, and the mixture is stirred at room temperature overnight. After the completion of the reaction, a saturated aqueous solution of sodium hydrogencarbonate is added and the mixture is extracted with ethyl acetate and chloroform. The organic layer is dried over anhydrous magnesium sulfate and concentrated under reduced pressure. The residue is recrystallized from ethyl acetate to give 0.36 g of (±)-N-(2-aminoethyl)-4-(4-chlorophenyl)-2,3,9-trimethyl-6H-thieno[3,2-f][1,2,4]triazolo[4,3-a][1,4]diazepine-6-acetamide 4/5 hydrate as white crystals, melting point 142°–146° C.

EXAMPLE 95

The compound of Example 83 (0.30 g) and 2N sodium hydroxide (0.54 ml) are added to ethanol (3 ml) and the mixture is stirred at room temperature for 4 days. After the completion of the reaction, the solvent is distilled away and water (100 ml) is added. The mixture is made acidic with 6N hydrochloric acid to give crude crystals. The crystals are recrystallized from ethanol to give 40 mg of (±)-3-((4-(4-chlorophenyl)-2,3,9-trimethyl-6H-thieno[3,2-f][1,2,4]triazolo[4,3-a][1,4]diazepin-6-yl)acetamide)benzoic acid 3/4 hydrate as white powdery crystals, melting point 256°–258° C.

EXAMPLE 96

(±)-Ethyl [2-(4-(4-chlorophenyl)-2,3,9-trimethyl-6H-thieno[3,2-f][1,2,4]triazolo[4,3-a][1,4]diazepin-6-yl)-acetamido]acetate (1.0 g) of Example 30 is added to ethanol (15 ml), and the mixture is stirred. 1N Sodium hydroxide (4 ml) is added at room temperature. After stirring at room temperature for 1 hour, the solvent is distilled away and the residue is dissolved in water and made acidic. The obtained crystals are recrystallized from aqueous ethanol to give 0.44 g of (±)-[2-(4-(4-chlorophenyl)-2,3,9-trimethyl-6H-thieno[3,2-f][1,2,4]triazolo[4,3-a][1,4]diazepin-6-yl)acetamide]acetic acid 1/4 hydrate, melting point 245°–247° C. (decomposition).

Starting Material Preparation Example 10

4-(4-Chlorophenyl)-2-ethyl-9-methyl-6H-thieno[3,2-f][1,2,4]triazolo[4,3-a][1,4]diazepine (6 g) is dissolved in diethyl carbonate (100 ml) under a nitrogen stream, and 60% sodium hydride (1.2 g) is added with stirring at room temperature. The mixture is refluxed under heating for 1 hour and cooled to 50° C. with ice water. Ethyl bromobutyrate (4.3 ml) is added. After stirring at 100° C. for 2 hours, the reaction mixture is poured into ice water (1 l) and extracted with ethyl acetate. The organic layer is washed with saturated brine, dried over anhydrous magnesium sulfate and concentrated under reduced pressure. The residue is purified by silica gel column chromatography (ethyl acetate:methanol=100:1) and crystallized from isopropyl ether to give 3.9 g of (±)-ethyl 4-(4-(4-chlorophenyl)-6-ethoxycarbonyl-2-ethyl-9-methyl-6H-thieno[3,2-f][1,2,4]triazolo[4,3-a][1,4]diazepin-6-yl)butyrate as white powdery crystals. (±)-Ethyl 4-(4-(4-chlorophenyl)-6-ethoxycarbonyl-2-ethyl-9-methyl-6H-thieno[3,2-f][1,2,4]-triazolo[4,3-a][1,4]diazepin-6-yl)butyrate (3.5 g) is dissolved in a mixture of ethanol (180 ml) and water (60 ml), and barium hydroxide 8 hydrate (8.4 g) is added. The mixture is refluxed under heating for 4 hours. After the completion of the reaction, ethanol is distilled away under reduced pressure and adjusted to pH 1 with 1N hydrochloric acid. The mixture is stirred for 30 minutes and adjusted to pH 4 with a saturated aqueous solution of sodium hydrogencarbonate to give 1.1 g of (±)-4-(4-(4-chlorophenyl)-2-ethyl-9-methyl-6H-thieno [3,2-f][1,2,4]triazolo[4,3-a][1,4]diazepin-6-yl)butyric acid as white powdery crystals, melting point 185°–187° C.

EXAMPLE 97

(±)-4-(4-(4-Chlorophenyl)-2-ethyl-9-methyl-6H-thieno [3,2-f][1,2,4]triazolo[4,3-a][1,4]diazepin-6-yl)butyric acid (0.50 g) and 1-hydroxybenzotriazole (0.17 g) are added to dry dimethylformamide (20 ml) and the mixture is stirred under ice-cooling. Thereto is added 1-ethyl-3-(3-dimethylaminopropyl) carbodiimide hydrochloride (0.25 g), and then triethylamine (0.24 g) and aniline (0.11 g) are added. The mixture is stirred at room temperature for 4 days. After the completion of the reaction, water (100 ml) is added and the mixture is extracted with ethyl acetate. The organic layer is washed with 6N hydrochloric acid, a saturated aqueous solution of sodium hydrogencarbonate and saturated brine, dried over anhydrous magnesium sulfate and concentrated under reduced pressure. The residue is purified by silica gel column chromatography (ethyl acetate:methanol=10:1) and crystallized from ethyl acetate and isopropyl ether to give 0.29 g of (±)-N-phenyl-4-(4-(4-chlorophenyl)-2-ethyl-9-methyl-6H-thieno[3,2-f][1,2,4] triazolo-[4,3-a][1,4]diazepin-6-yl)butaneamide as white powdery crystals, melting point 238°–240° C.

EXAMPLE 98

(±)-N-(3-Pyridyl)-4-(4-(4-chlorophenyl)-2-ethyl-9-methyl-6H-thieno[3,2-f][1,2,4]triazolo[4,3-a][1,4]diazepin-6-yl)-butaneamide 1/2 hydrate, melting point 208°–210° C.

Starting Material Preparation Example 11

4-(4-Chlorophenyl)-2-ethyl-9-methyl-6H-thieno[3,2-f][1,2,4]triazolo[4,3-a][1,4]diazepine (10 g) is dissolved in diethyl carbonate (150 ml) in a nitrogen stream, and 60% sodium hydride (2.0 g) is added with stirring at room temperature. The mixture is refluxed under heating for 2 hours and cooled to 50° C. with ice water. Ethyl bromovalerate (7.9 ml) is added. After stirring at 100° C. for 2 hours, the reaction mixture is poured on ice water (1 l) and extracted with ethyl acetate. The organic layer is washed with saturated brine, dried over anhydrous magnesium sulfate and concentrated under reduced pressure. The residue is purified by silica gel column chromatography (ethyl acetate:methanol=100:1) and crystallized from isopropyl ether and ethyl acetate to give 8.3 g of (±)-ethyl 5-(4-(4-chlorophenyl)-6-ethoxycarbonyl-2-ethyl-9-methyl-6H-thieno[3,2-f][1,2,4]triazolo[4,3-a][1,4]diazepin-6-yl) valerate as white powdery crystals. (±)-Ethyl 5-(4-(4-chlorophenyl)- 6-ethoxycarbonyl-2-ethyl-9-methyl-6H-thieno[3,2-f][1,2,4]triazolo[4,3-a][1,4]diazepin-6-yl) valerate (8.2 g) is dissolved in a mixture of ethanol (90 ml) and water (30 ml), and barium hydroxide 8 hydrate (19 g) is added. The mixture is refluxed under heating for 4 hours. After the completion of the reaction, ethanol is distilled away under reduced pressure and adjusted to pH 1 with 6N hydrochloric acid. The mixture is stirred for 30 minutes and adjusted to pH 4 with a saturated aqueous solution of sodium hydrogencarbonate and extracted with chloroform. The organic layer is washed with a saturated brine, dried over anhydrous magnesium sulfate and concentrated under reduced pressure. The residue is crystallized from ethyl acetate and isopropyl ether and recrystallized from chloroform and methanol to give 3.2 g of (±)-5-(4-(4-chlorophenyl)-2-ethyl-9-methyl-6H-thieno[3,2-f][1,2,4] triazolo[4,3-a][1,4]diazepin-6-yl)valeric acid as white powdery crystals, melting point 257°–260° C.

EXAMPLE 99

(±)-5-(4-(4-Chlorophenyl)-2-ethyl-9-methyl-6H-thieno [3,2-f][1,2,4]triazolo[4,3-a][1,4]diazepin-6-yl)valeric acid (0.50 g) and 1-hydroxybenzotriazole (0.17 g) are added to dry dimethylformamide (20 ml) and the mixture is stirred under ice-cooling. Thereto is added 1-ethyl-3-(3-dimethylaminopropyl)-carbodiimide hydrochloride (0.24 g), and then triethylamine (0.23 g) and aniline (0.10 g) are added. The mixture is stirred at room temperature for 4 days. After the completion of the reaction, water (100 ml) is added and the mixture is extracted with ethyl acetate. The organic layer is washed with 6N hydrochloric acid, a saturated aqueous solution of sodium hydrogencarbonate and saturated brine, dried over anhydrous magnesium sulfate and concentrated under reduced pressure. The residue is purified by silica gel column chromatography (ethyl acetate:methanol=10:1) and crystallized from ethyl acetate and isopropyl ether to give 0.47 g of (±)-N-phenyl-5-(4-(4-chlorophenyl)-2-ethyl-9-methyl-6H-thieno[3,2-f][1,2,4]-triazolo[4,3-a][1,4]diazepin-6-yl)pentaneamide as white powdery crystals, melting point 238°–240° C.

EXAMPLE 100

(±)-N-(3-Pyridyl)-5-(4-(4-chlorophenyl)-2-ethyl-9-methyl-6H-thieno[3,2-f][1,2,4]triazolo[4,3-a][1,4]diazepin-6-yl)-pentaneamide 1/4 hydrate, melting point 179°–182° C.

EXAMPLE 101

(±)-N-(4-Pyridyl)-5-(4-(4-chlorophenyl)-2-ethyl-9-methyl-6H-thieno[3,2-f][1,2,4]triazolo[4,3-a][1,4]diazepin-6-yl)-pentaneamide, melting point 241°–243° C.

Starting Material Preparation Example 12

4-(4-Chlorophenyl)-2-ethyl-9-methyl-6H-thieno[3,2-f][1,2,4]triazolo[4,3-a][1,4]diazepine (10 g) is dissolved in diethyl carbonate (150 ml) in a nitrogen stream, and 60% sodium hydride (2.0 g) is added with stirring at room temperature. The mixture is refluxed under heating for 2 hours and cooled to 50° C. with ice water. Ethyl acrylate (5.4 ml) is added. After stirring at 50° C. for 3 hours, the reaction mixture is poured into ice water (1 l) and extracted with ethyl acetate. The organic layer is washed with saturated brine, dried over anhydrous magnesium sulfate and concentrated under reduced pressure. The residue is purified by silica gel column chromatography (ethyl acetate:methanol=100:1) to give 3.2 g of (±)-ethyl 3-(4-(4-chlorophenyl)-6-ethoxycarbonyl-2-ethyl-9-methyl-6H-thieno[3,2-f][1,2,4] triazolo[4,3-a][1,4]diazepin-6-yl)propionate as an oil. (±)-Ethyl 3-(4-(4-chlorophenyl)-6-ethoxycarbonyl-2-ethyl-9-methyl-6H-thieno[3,2-f][1,2,4]-triazolo[4,3-a][1,4] diazepin-6-yl)propionate (3.2 g) is dissolved in a mixture of ethanol (90 ml) and water (30 ml), and barium hydroxide 8 hydrate (7.8 g) is added. The mixture is refluxed under heating for 4 hours. After the completion of the reaction, ethanol is distilled away under reduced pressure and adjusted to pH 1 with 6N hydrochloric acid. The mixture is stirred for 30 minutes and adjusted to pH 4 with a saturated aqueous solution of sodium hydrogencarbonate and extracted with chloroform. The organic layer is washed with a saturated brine, dried over anhydrous magnesium sulfate and concentrated under reduced pressure. The residue is crystallized from ethyl acetate and isopropyl ether to give 0.1 g of (±)-3-(4-(4-chlorophenyl)-2-ethyl-9-methyl-6H-thieno[3,2-f][1,2,4]-triazolo[4,3-a][1,4]diazepin-6-yl) propionic acid as brown crystals, melting point 210°–212° C.

EXAMPLE 102

(±)-3-(4-(4-Chlorophenyl)-2-ethyl-9-methyl-6H-thieno [3,2-f][1,2,4]triazolo[4,3-a][1,4]diazepin-6-yl)propionic acid (0.33 g) and 1-hydroxybenzotriazole (0.12 g) are added to dry dimethylformamide (20 ml) and the mixture is stirred under ice-cooling. Thereto is added 1-ethyl-3-(3-dimethylaminopropyl)-carbodiimide hydrochloride (0.17 g), and then triethylamine (0.16 g) and aniline (72 mg) are added. The mixture is stirred at room temperature for 24 hours. After the completion of the reaction, water (100 ml) is added and the mixture is extracted with ethyl acetate. The organic layer is washed with 6N hydrochloric acid, a saturated aqueous solution of sodium hydrogencarbonate and saturated brine, dried over anhydrous magnesium sulfate and concentrated under reduced pressure. The residue is purified by silica gel column chromatography (ethyl acetate:methanol=10:1) and crystallized from ethyl acetate and isopropyl ether to give 0.03 g of (±)-N-phenyl-3-(4-(4-chlorophenyl)-2-ethyl-9-methyl-6H-thieno[3,2-f][1,2,4]triazolo-[4,3-a][1,4]diazepin-6-yl)propaneamide as white powdery crystals, melting point 183°–185° C.

EXAMPLE 103

(±)-N-(3-Pyridyl)-3-(4-(4-chlorophenyl)-2-ethyl-9-methyl-6H-thieno[3,2-f][1,2,4]triazolo[4,3-a][1,4]diazepin-6-yl)-propaneamide 1/4 hydrate, melting point 213°–216° C.

Starting Material Preparation Example 13

60% Sodium hydride (oil suspension) is added to benzene (90 ml) and the mixture is refluxed under heating. Acetonitrile (23 ml) dissolved in benzene (23 ml) is added and the mixture is refluxed for 1 hour. A solution of methyl cyclohexanecarboxylate (63 g) dissolved in benzene (70 ml) is dropwise added and the mixture is refluxed under heating for 5 hours. After the completion of the reaction, the mixture is cooled to room temperature and poured into ice water (200 ml). The organic layer is removed and the aqueous layer is washed with isopropyl ether. The aqueous layer is adjusted to pH 2 with conc. hydrochloric acid and extracted 3 times with isopropyl ether. The extract is dried over anhydrous magnesium sulfate and the solvent is distilled away under reduced pressure to give 34 g of cyanomethyl cyclohexyl ketone. The obtained cyanomethyl cyclohexyl ketone (34 g), morpholine (17.6 ml) and ethyl methyl ketone (18 ml) are dissolved in ethanol (150 ml) and sulfur (6.47 g) is suspended. The suspension is refluxed under heating for 10 hours. After the completion of the reaction, the solvent is distilled away under reduced pressure.

The residue is dissolved in chloroform (200 ml) and washed with water. The mixture is dried over anhydrous magnesium sulfate and filtered.

Chloroacetyl chloride (17.9 ml) is dropwise added and the mixture is refluxed under heating for 1 hour. After the completion of the reaction, the mixture is washed with a saturated aqueous solution of sodium hydrogencarbonate and dried over anhydrous magnesium sulfate. The solvent is distilled away under reduced pressure and the residue is subjected to column chromatography to give 13.5 g of N-(2-(3-cyclohexylcarbonyl-4,5-dimethyl)-thienyl) chloroacetamide.

$^1$H-NMR ($CDCl_3$, ppm) δ: 1.19–1.87 (m,9H), 2.29 (s,3H), 2.34 (s,3H), 3.05–3.14 (m,1H), 4.22 (s,2H)

Starting Material Preparation Example 14

N-(2-(3-Cyclohexylcarbonyl-4,5-dimethyl)thienyl) chloro-acetamide (13.5 g) is dissolved in tetrahydrofuran (150 ml) and sodium iodide (7.1 g) is suspended. The suspension is refluxed under heating for 2 hours. The reaction mixture is cooled to −50° C. with dry ice-acetone and liquid ammonium (25 ml) is added. The mixture is stirred to gradually recover room temperature. After the completion of the reaction, the solvent is distilled away under reduced pressure. The residue is dissolved in ethyl acetate (200 ml). The mixture is washed with water and dried over anhydrous magnesium sulfate. The solvent is distilled away under reduced pressure. The residue is dissolved in isopropyl alcohol (250 ml) and acetic acid (2 ml) is added. The mixture is refluxed under heating for 5 hours. The solvent is distilled away under reduced pressure and the residue is dissolved in chloroform (150 ml). The mixture is washed with a saturated aqueous solution of sodium hydrogencarbonate and dried over anhydrous magnesium sulfate. The solvent is distilled away under reduced pressure and the residue is subjected to column chromatography to give 7.7 g of 5-cyclohexyl-6,7-dimethyl-1,2-dihydro-3H-thieno[2,3-e][1,4]diazepin-2-one, melting point 205° C.

Starting Material Preparation Example 15

5-Cyclohexyl-6,7-dimethyl-1,2-dihydro-3H-thieno[2,3-e][1,4]diazepin-2-one (7.7 g) is dissolved in chloroform (100 ml). Diphosphorus pentasulfide (6.2 g) is added with stirring and the mixture is refluxed under heating for 3 hours. After the completion of the reaction, the reaction mixture is neutralized with a saturated aqueous solution of sodium hydrogencarbonate, washed with water and dried over anhydrous magnesium sulfate. The solvent is distilled away under reduced pressure and the residue is suspended in methanol (60 ml). After cooling, 100% hydrazine hydrate (3.4 ml) is added and the mixture is stirred at room temperature for 2 hours. After the completion of the reaction, the precipitated crystals are collected by filtration to give 7 g of 5-cyclohexyl-6,7-dimethyl-1,2-dihydro-3H-thieno[2,3-e][1,4]diazepine-2-hydrazone, melting point 213–215° C.

Starting Material Preparation Example 16

5-Cyclohexyl-6,7-dimethyl-1,2-dihydro-3H-thieno[2,3-e][1,4]diazepine-2-hydrazone (7 g) is suspended in toluene (100 ml). Triethyl orthoacetate (6.6 ml) is added and the mixture is stirred at 80° C. for 4 hours. After the completion of the reaction, the solvent is distilled away under reduced pressure and the residue is subjected to column chromatography. The reaction mixture obtained (4.8 g) is dissolved in diethyl carbonate (70 ml) and 60% sodium hydride (1.04 g) is added at room temperature with stirring. The mixture is refluxed under heating for 2 hours, cooled with ice water and added with ethyl bromoacetate (2 ml). The mixture is stirred at room temperature for 3 hours and the reaction mixture is poured into a cool 5% aqueous acetic acid solution and extracted with ethyl acetate. The mixture is washed with water, dried over anhydrous magnesium sulfate, filtered and concentrated under reduced pressure. The residue is subjected to silica gel column chromatography. The objective fraction is concentrated under reduced pressure. The obtained oily substance (5.4 g) is dissolved in ethanol (100 ml). A 1N aqueous solution (34 ml) of sodium hydroxide is added with stirring and the mixture is stirred at 50° C. for 8 hours. The mixture is adjusted to pH 2 with 1N hydrochloric acid and extracted with chloroform. The solvent is distilled away under reduced pressure and the residue is subjected to column chromatography to give 2.2 g of amorphous (±)-4-cyclohexyl-2,3,9-trimethyl-6H-thieno[3,2-f][1,2,4]triazolo[4,3-a][1,4]diazepine-6-acetic acid.

$^1$H-NMR ($CDCl_3$, ppm) δ: 0.82–2.04 (m,10H), 2.23 (s,3H), 2.41 (s,3H), 2.62 (s,3H), 3.43 (d,2H,J=6.6 Hz), 4.38 (t,1H,J=6.6 Hz)

EXAMPLE 104

(±)-4-Cyclohexyl-2,3,9-trimethyl-6H-thieno[3,2-f][1,2,4]triazolo[4,3-a][1,4]diazepine-6-acetic acid (0.54 g) and triethylamine (0.22 ml) are added to a mixed solvent of dimethylformamide (20 ml) and tetrahydrofuran (10 ml).

The mixture is cooled to −5° C. and pivaloyl chloride (0.18 ml) is dropwise added at said temperature. Ten minutes later, a 40% aqueous solution (2 ml) of methylamine is dropwise added at said temperature and the mixture is stirred at room temperature for 2 hours. Water is added to the reaction mixture, and the mixture is extracted with ethyl acetate, washed with water and dried over anhydrous magnesium sulfate. The solvent is distilled away under reduced pressure and the residue is recrystallized from ethyl acetate to give (±)-N-methyl-4-cyclohexyl-2,3,9-trimethyl-6H-thieno[3,2-f][1,2,4]triazolo[4,3-a][1,4]diazepine-6-acetamide, melting point 228°–231° C.

Starting Material Preparation Example 101

4-(4-Chlorophenyl)-2-ethyl-9-methyl-6H-thieno[3,2-f][1,2,4]triazolo[4,3-a][1,4]diazepine (1 g) is dissolved in diethyl carbonate (35 ml) in a nitrogen stream, and 60% sodium hydride is added with stirring at room temperature. The mixture is refluxed under heating for 2 hours and cooled to room temperature. Ethyl bromoacetate (0.32 ml) is added. After stirring at room temperature for 3 hours, the reaction mixture is poured into cold water and extracted with ethyl acetate. The organic layer is washed with water, dried over anhydrous magnesium sulfate, filtered and concentrated under reduced pressure. The residue is subjected to silica gel column chromatography. The objective fraction is concentrated under reduced pressure, and the residue is suspended in a mixture of ethanol (90 ml) and water (30 ml). Barium hydroxide octahydrate (0.65 g) is added with stirring at room temperature.

The mixture is stirred at room temperature for 10 hours and concentrated under reduced pressure. Water is added to the residue and the mixture is washed with ethyl acetate. The aqueous layer is adjusted to pH 2 with 6N hydrochloric acid and allowed to stand at room temperature overnight. The reaction mixture is neutralized with sodium hydrogencarbonate and extracted with ethyl acetate. The extract is dried over anhydrous magnesium sulfate and filtered. The filtrate is concentrated under reduced pressure and isopropyl ether is added to the residue to allow crystallization, whereby 0.15 g of (4-(4-chlorophenyl)-2-ethyl-9-methyl-6H-thieno[3,2-f][1,2,4]triazolo[4,3-a][1,4]diazepin-6-yl)acetic acid as pale brown crystals, melting point 198°–202° C.

EXAMPLE 201

(4-(4-Chlorophenyl)-2-ethyl-9-methyl-6H-thieno[3,2-f][1,2,4]triazolo[4,3-a][1,4]diazepin-6-yl)acetic acid (2 g) obtained in Starting Material Preparation Example 101 is dissolved in dimethylformamide (50 ml), and aniline (0.59 ml), triethylamine (1.4 ml) and 1-hydroxybenzotriazole (0.75 g) are added with stirring at room temperature. The reaction mixture is cooled to not more than 0° C. with stirring and N-ethyl-N'-(3-dimethylaminopropyl) carbodiimide hydrochloride (1.05 g) is added. The mixture is stirred overnight at room temperature. The reaction mixture is poured into water and extracted with ethyl acetate. The organic layer is washed with 1N hydrochloric acid, 1N sodium hydroxide and water, and dried over anhydrous magnesium sulfate. After filtering, the filtrate is concentrated under reduced pressure and the obtained crystals are recrystallized from ethanol to give 1.4 g of N-phenyl-(4-(4-chlorophenyl)-2-ethyl-9-methyl-6H-thieno[3,2-f][1,2,4]triazolo-[4,3-a][1,4]diazepin-6-yl)acetamide, melting point 238°–239° C.

In the same manner, the following compounds are obtained.

EXAMPLE 202

N-(3-Methylphenyl)-(4-(4-chlorophenyl)-2-ethyl-9-methyl-6H-thieno[3,2-f][1,2,4]triazolo[4,3-a][1,4]diazepin-6-yl)-acetamide, melting point 247°–248° C.

EXAMPLE 203

N-(3-Chlorophenyl)-(4-(4-chlorophenyl)-2-ethyl-9-methyl-6H-thieno[3,2-f][1,2,4]triazolo[4,3-a][1,4]diazepin-6-yl)-acetamide, melting point 217°–218° C.

EXAMPLE 204

N-(2-Methoxyphenyl)-(4-(4-chlorophenyl)-2-ethyl-9-methyl-6H-thieno[3,2-f][1,2,4]triazolo[4,3-a][1,4]diazepin-6-yl)acetamide, melting point 198°–200° C.

EXAMPLE 205

N-(3-Methoxyphenyl)-(4-(4-chlorophenyl)-2-ethyl-9-methyl-6H-thieno[3,2-f][1,2,4]triazolo[4,3-a][1,4]diazepin-6-yl)acetamide, melting point 244° C.

The compounds obtained above and the compounds obtained in the same manner as in the above-mentioned Examples are shown in the following Tables.

TABLE 10

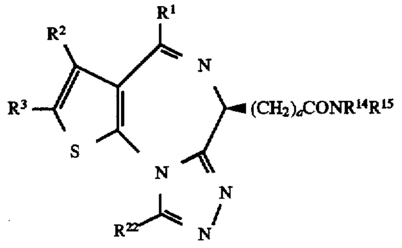

| Example No. | $R^1$ | $R^2$ | $R^3$ | $R^{22}$ | a | $R^{14}$ | $R^{15}$ |
|---|---|---|---|---|---|---|---|
| 1 | 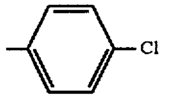 | Me | Me | Me | 1 | H | Me |

TABLE 10-continued
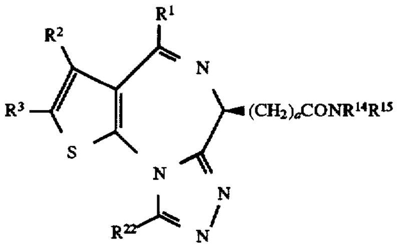
| Example No. | $R^1$ | $R^2$ | $R^3$ | $R^{22}$ | a | $R^{14}$ | $R^{15}$ |
|---|---|---|---|---|---|---|---|
| 2 | 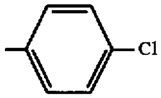 | Me | Me | Me | 1 | H | $CH_2CH_2OH$ |
| 3 | 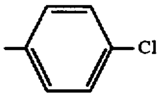 | Me | Me | Me | 1 | H | 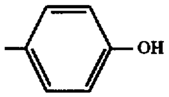 |
| 4 | 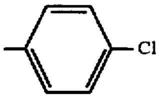 | Me | Me | Me | 1 | H | 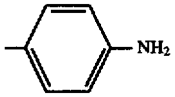 |
| 5 | 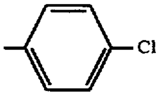 | Me | Me | Me | 1 | H | 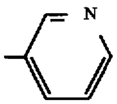 |
| 6 | 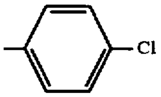 | Me | Me | Me | 1 | H | $CH_2CONH_2$ |
| 7 | 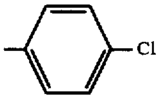 | Me | Me | Me | 1 | H | 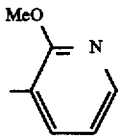 |
| 8 | 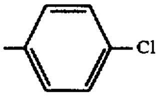 | Me | Me | Me | 1 | H | 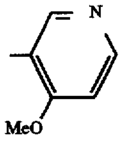 |
| 9 | 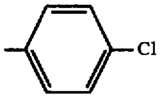 | Me | Me | Me | 1 | H | OMe |
| 10 | 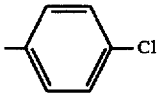 | Me | Me | Me | 1 | H | $CH(CH_2OH)_2$ |

TABLE 11
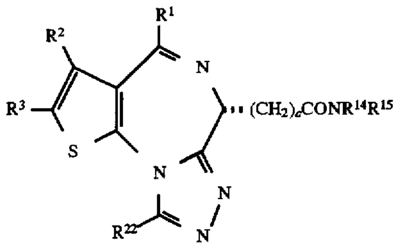
| Example No. | $R^1$ | $R^2$ | $R^3$ | $R^{22}$ | a | $R^{14}$ | $R^{15}$ |
|---|---|---|---|---|---|---|---|
| 11 | 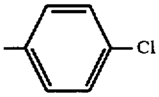 | Me | Me | Me | 1 | H | $CH_2CH_2OH$ |
TABLE 11-continued
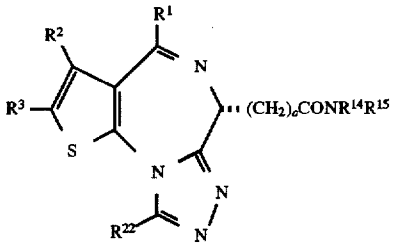
| Example No. | $R^1$ | $R^2$ | $R^3$ | $R^{22}$ | a | $R^{14}$ | $R^{15}$ |
|---|---|---|---|---|---|---|---|
| 12 | 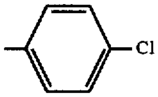 | Me | Me | Me | 1 | H | $CH_3$ |
TABLE 12
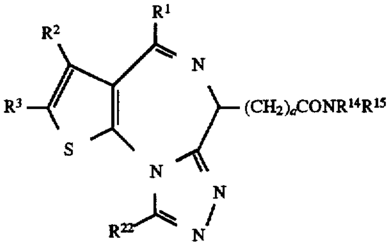
| Example No. | $R^1$ | $R^2$ | $R^3$ | $R^{22}$ | a | $R^{14}$ | $R^{15}$ |
|---|---|---|---|---|---|---|---|
| 13 | 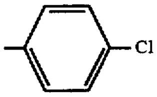 | Me | Me | Me | 1 | H | 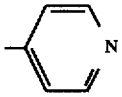 |
| 14 | 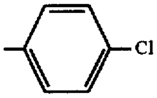 | Me | Me | Me | 1 | H | 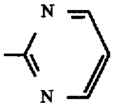 |
| 15 | 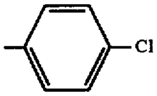 | Me | Me | Me | 1 | H | 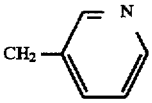 |
| 16 | 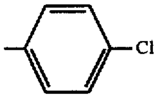 | Me | Me | Me | 1 | H | 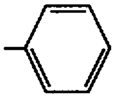 |
| 17 | 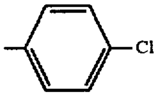 | Me | Me | Me | 1 | H | 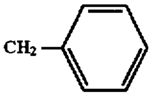 |
| 18 | 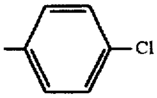 | Me | Me | Me | 1 | H | 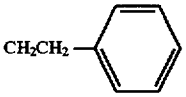 |

TABLE 12-continued
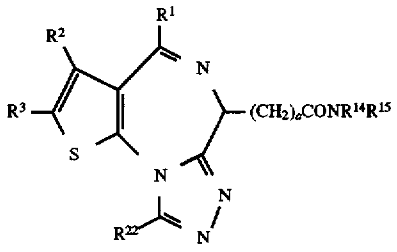
| Example No. | $R^1$ | $R^2$ | $R^3$ | $R^{22}$ | a | $R^{14}$ | $R^{15}$ |
|---|---|---|---|---|---|---|---|
| 19 | 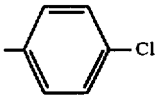 | Me | Me | Me | 1 | H | 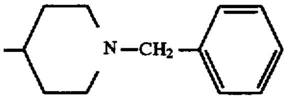 |
| 20 | 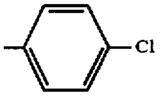 | Me | Me | Me | 1 | H | 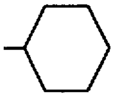 |
| 21 | 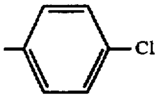 | Me | Me | Me | 1 | H | $CH_2CH_2CH_3$ |
| 22 | 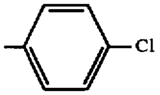 | Me | Me | Me | 1 | | $-CH_2CH_2SCH_2CH_2-$ |
| 23 | 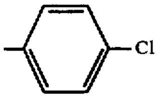 | Me | Me | Me | 1 | H | 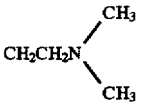 |
| 24 | 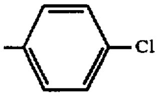 | Me | Me | Me | 1 | H | $CH_3$ |
| 25 | 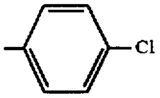 | Me | Me | Me | 1 | $CH_3$ | $CH_3$ |
| 26 | 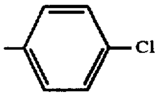 | Me | Me | Me | 1 | H | 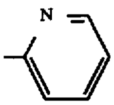 |

TABLE 13
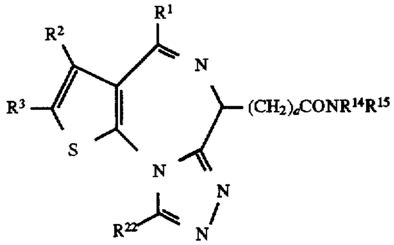
| Example No. | $R^1$ | $R^2$ | $R^3$ | $R^{22}$ | a | $R^{14}$ | $R^{15}$ |
|---|---|---|---|---|---|---|---|
| 27 | 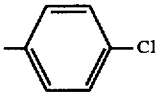 | Me | Me | Me | 1 | | $-CH_2CH_2N(Me)CH_2CH_2-$ |
| 28 | 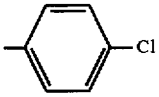 | Me | Me | Me | 1 | H | H |
| 29 | 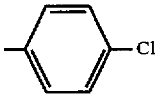 | Me | Me | Me | 1 | H | $CH_2CH_2OH$ |
| 30 | 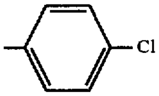 | Me | Me | Me | 1 | H | $CH_2COOEt$ |
| 31 | 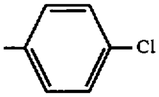 | Me | Me | Me | 1 | | $-N=C(NH_2)CH=CH-$ |
| 32 | 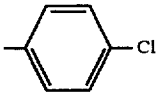 | Me | Me | Me | 1 | | 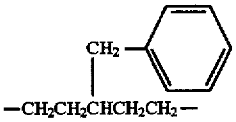 |
| 33 | 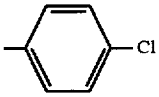 | Me | Me | Me | 1 | H | 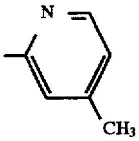 |
| 34 | 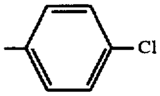 | Me | Me | Me | 1 | H | 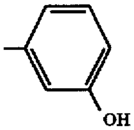 |
| 35 | 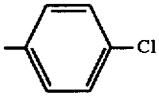 | Me | Me | Me | 1 | H | 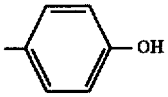 |
| 36 | 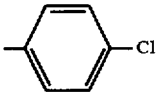 | Me | Me | Me | 1 | H | 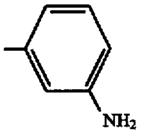 |

TABLE 14
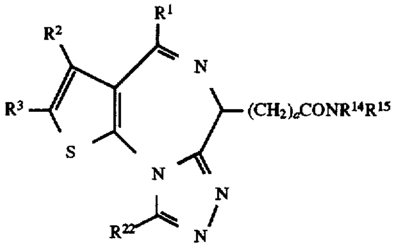
| Example No. | $R^1$ | $R^2$ | $R^3$ | $R^{22}$ | a | $R^{14}$ | $R^{15}$ |
|---|---|---|---|---|---|---|---|
| 37 | 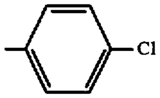 | Me | Me | Me | 1 | H | 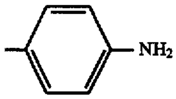 |
| 38 | 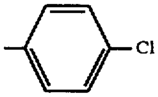 | Me | Me | Me | 1 | H | $CH_2CONH_2$ |
| 39 | 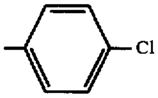 | Me | Me | Me | 1 | H | 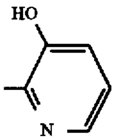 |
| 40 | 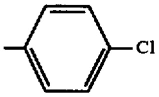 | Me | Me | Me | 1 | H | $CH_2CH_3$ |
| 41 | 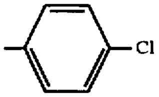 | Me | Me | Me | 1 | H | 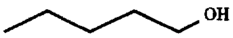 |
| 42 | 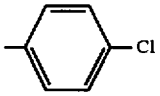 | Me | Me | Me | 1 | H | 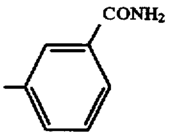 |
| 43 | 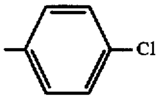 | Me | Me | Me | 1 | H | 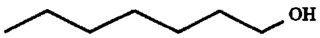 |
| 44 | 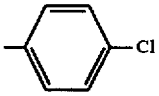 | Me | Me | Me | 1 | H | OH |
| 45 | 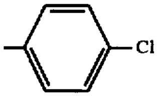 | Me | Me | Me | 1 | H | 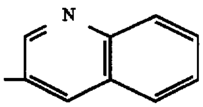 |
| 46 | 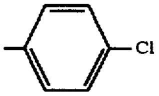 | Me | Me | Me | 1 | H | 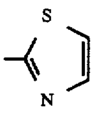 |

TABLE 15
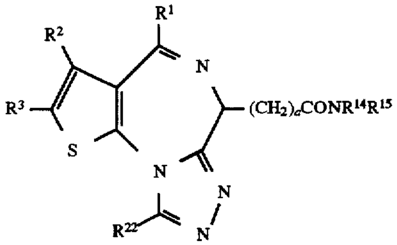
| Example No. | $R^1$ | $R^2$ | $R^3$ | $R^{22}$ | a | $R^{14}$ | $R^{15}$ |
|---|---|---|---|---|---|---|---|
| 47 | 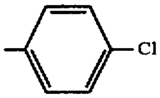 | Me | Me | Me | 1 | H | 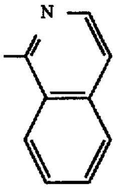 |
| 48 | 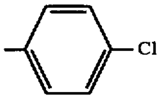 | Me | Me | Me | 1 | H | 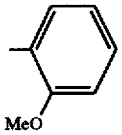 |
| 49 | 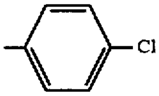 | Me | Me | Me | 1 | H | 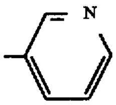 |
| 50 | 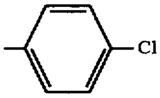 | Me | Me | Me | 1 | | $-CH_2CH_2OCH_2CH_2-$ |
| 51 | 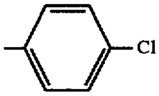 | Me | Me | Me | 1 | | $-CH_2CH_2CH_2CH_2CH_2-$ |
| 52 | 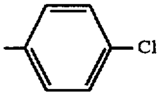 | Me | Me | Me | 1 | | $CH_2CH_2OH$<br>\|<br>$-CH_2CH_2NCH_2CH_2-$ |
| 53 | 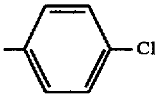 | Me | Me | Me | 1 | H | $CH_2CH{=}CH_2$ |
| 54 | 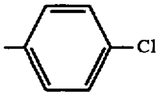 | Me | Me | Me | 1 | H | 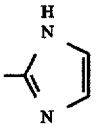 |
| 55 | 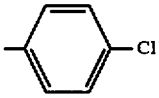 | Me | Me | Me | 1 | | $-N-CH(NH_2)N{=}CH-$ |
| 56 | 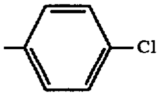 | Me | Me | Me | 1 | H | 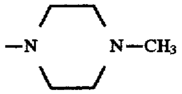 |

TABLE 16
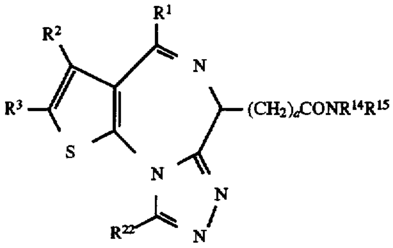
| Example No. | $R^1$ | $R^2$ | $R^3$ | $R^{22}$ | a | $R^{14}$ | $R^{25}$ |
|---|---|---|---|---|---|---|---|
| 57 | 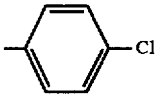 | Me | Me | Me | 1 | H | 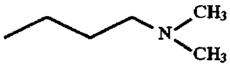 |
| 58 | 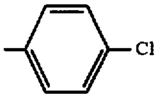 | Me | Me | Me | 1 | Et | Et |
| 59 | 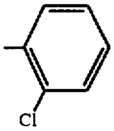 | H | Et | Me | 1 | H | 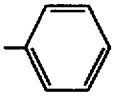 |
| 60 | 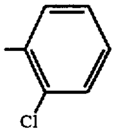 | H | Et | Me | 1 | H | 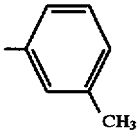 |
| 61 | 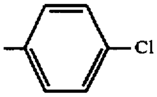 | H | Et | Me | 1 | H | 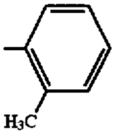 |
| 62 | 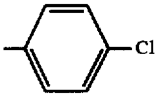 | H | Et | Me | 1 | H | 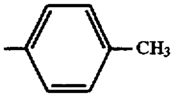 |
| 63 | 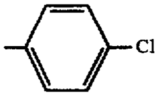 | H | Et | Me | 1 | H | 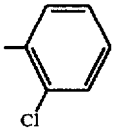 |
| 64 | 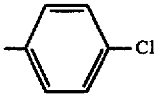 | H | Et | Me | 1 | H | 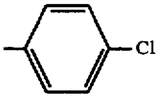 |
| 65 | 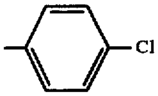 | H | Et | Me | 1 | H | 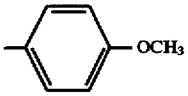 |
| 66 | 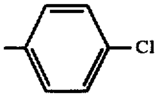 | H | Et | Me | 1 | H | 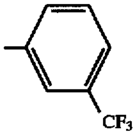 |

TABLE 17
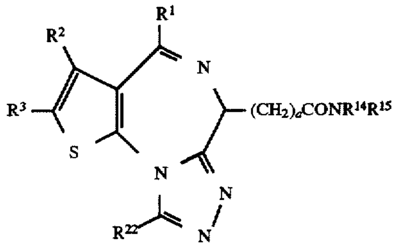
| Example No. | R¹ | R² | R³ | R²² | a | R¹⁴ | R¹⁵ |
|---|---|---|---|---|---|---|---|
| 67 | 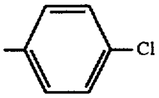 | H | Et | Me | 1 | H | 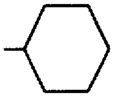 |
| 68 | 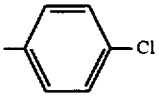 | H | Et | Me | 1 | H | 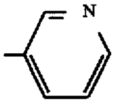 |
| 69 | 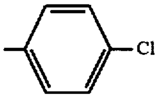 | H | Et | Me | 1 | H | 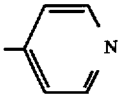 |
| 70 | 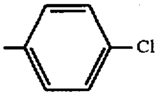 | H | Et | Me | 1 | H | 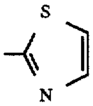 |
| 71 | 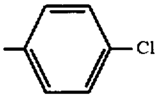 | H | Et | Me | 1 | H | 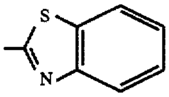 |
| 72 | 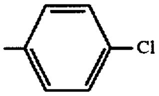 | H | Et | Me | 1 | H | 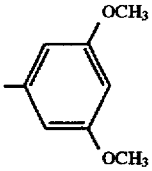 |
| 73 | 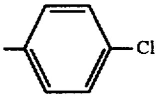 | H | Et | Me | 1 | $-CH_2CH_2CH_2CH_2CH_2-$ | |
| 74 | 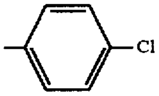 | H | Et | Me | 1 | H | 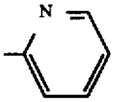 |
| 75 | 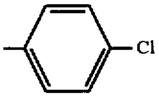 | H | Et | Me | 1 | H | 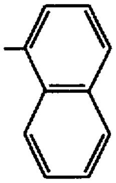 |
| 76 | 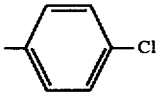 | H | Et | Me | 1 | $-CH_2CH_2N(CH_3)CH_2CH_2-$ | |

TABLE 18
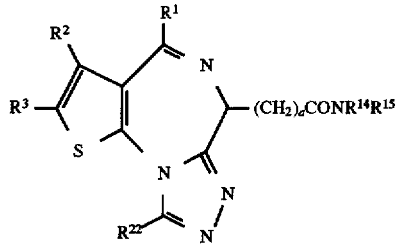
| Example No. | $R^1$ | $R^2$ | $R^3$ | $R^{22}$ | a | $R^{14}$ | $R^{15}$ |
|---|---|---|---|---|---|---|---|
| 77 | 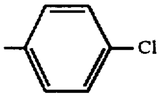 | Me | Me | Me | 1 | | $-CH_2CH_2CH(OH)CH_2CH_2-$ |
| 78 | 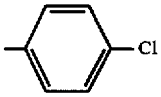 | Me | Me | Me | 1 | H | $CH_2CH_2CH_2CH_2CH_3$ |
| 79 | 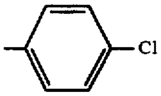 | Me | Me | Me | 1 | H | 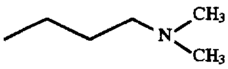 |
| 80 | 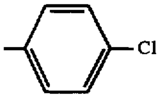 | Me | Me | Me | 1 | $C_3H_7$ | $C_3H_7$ |
| 81 | 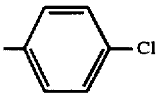 | Me | Me | Me | 1 | H | 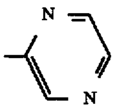 |
| 82 | 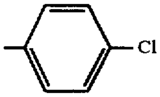 | Me | Me | Me | 1 | H | 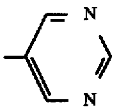 |
| 83 | 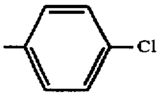 | Me | Me | Me | 1 | H | 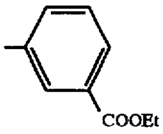 |
| 84 | 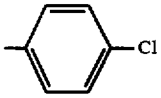 | Me | Me | Me | 1 | Me | 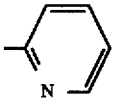 |
| 85 | 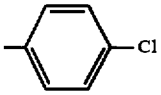 | Me | Me | Me | 1 | H | 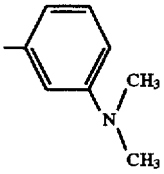 |
| 86 | 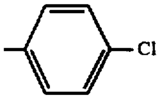 | Me | Me | Me | 1 | H | 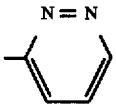 |

TABLE 19
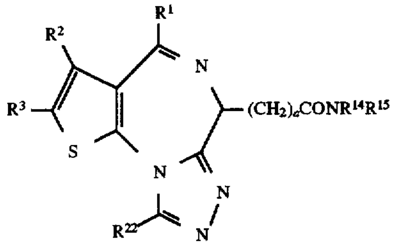
| Example No. | $R^1$ | $R^2$ | $R^3$ | $R^{22}$ | a | $R^{14}$ | $R^{15}$ |
|---|---|---|---|---|---|---|---|
| 87 | 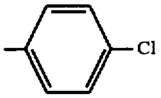 | Me | Me | Me | 1 | H | 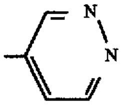 |
| 88 | 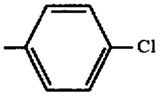 | Me | Me | Me | 1 | Me | 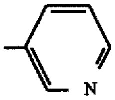 |
| 89 | 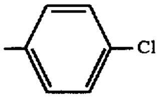 | Me | Me | Me | 1 | H | 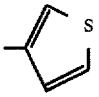 |
| 90 | 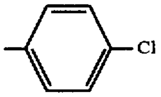 | Me | Me | Me | 1 | H | 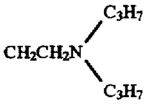 |
| 91 | 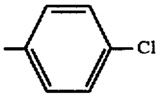 | Me | Me | Me | 1 | H | $CH_2CH_2COOEt$ |
| 92 | 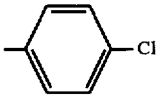 | Me | Me | Me | 1 | H | $CH_2CH_2COOH$ |
| 93 | 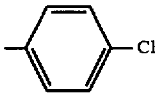 | Me | Me | Me | 1 | H | $CH_2CH_2NHCOO$-tBu |
| 94 | 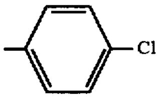 | Me | Me | Me | 1 | H | $CH_2CH_2NH_2$ |
| 95 | 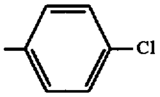 | Me | Me | Me | 1 | H | 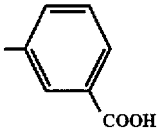 |
| 96 | 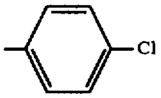 | Me | Me | Me | 1 | H | $CH_2COOH$ |

TABLE 20
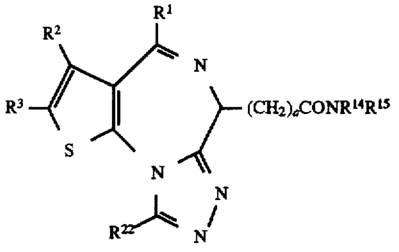
| Example No. | $R^1$ | $R^2$ | $R^3$ | $R^{22}$ | a | $R^{14}$ | $R^{15}$ |
|---|---|---|---|---|---|---|---|
| 97 | 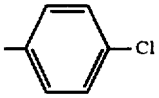 | H | Et | Me | 3 | H | 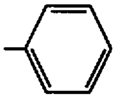 |
| 98 | 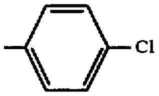 | H | Et | Me | 3 | H | 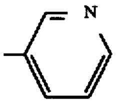 |
| 99 | 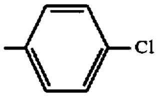 | H | Et | Me | 4 | H | 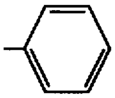 |
| 100 | 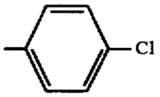 | H | Et | Me | 4 | H | 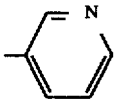 |
| 101 | 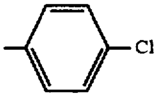 | H | Et | Me | 4 | H | 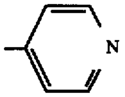 |
TABLE 20-continued
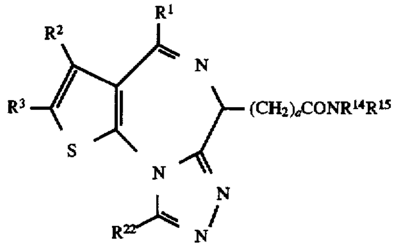
| Example No. | $R^1$ | $R^2$ | $R^3$ | $R^{22}$ | a | $R^{14}$ | $R^{15}$ |
|---|---|---|---|---|---|---|---|
| 102 | 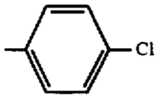 | H | Et | Me | 2 | H | 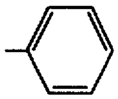 |
| 103 | 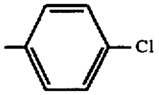 | H | Et | Me | 2 | H | 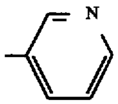 |
| 104 | 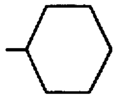 | Me | Me | Me | 1 | H | $CH_3$ |
TABLE 21
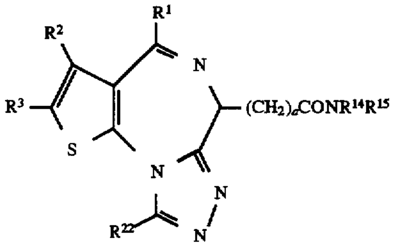
| Example No. | $R^1$ | $R^2$ | $R^3$ | $R^{22}$ | a | $R^{14}$ | $R^{15}$ |
|---|---|---|---|---|---|---|---|
| 201 | 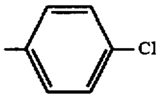 | H | Et | Me | 1 | H | 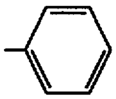 |

TABLE 21-continued
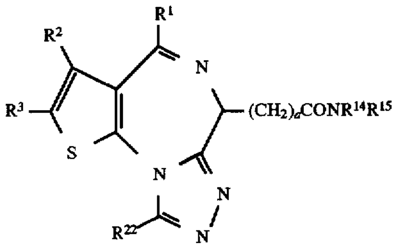
| Example No. | R¹ | R² | R³ | R²² | a | R¹⁴ | R¹⁵ |
|---|---|---|---|---|---|---|---|
| 202 | 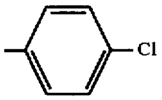 | H | Et | Me | 1 | H | 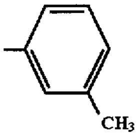 |
| 203 | 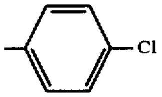 | H | Et | Me | 1 | H | 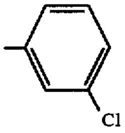 |
| 204 | 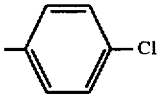 | H | Et | Me | 1 | H | 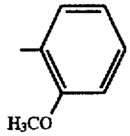 |
| 205 | 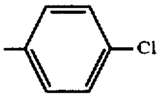 | H | Et | Me | 1 | H | 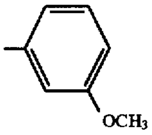 |
TABLE 22
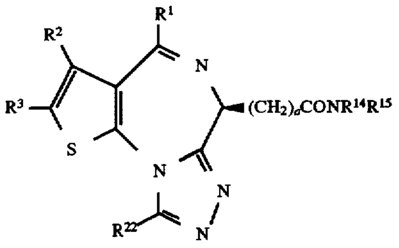
| No. | R¹ | R² | R³ | R²² | a | R¹⁴ | R¹⁵ |
|---|---|---|---|---|---|---|---|
| 301 | 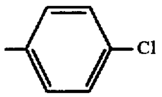 | Me | Me | Me | 1 | H | 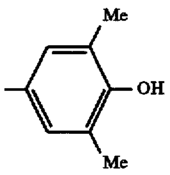 |
| 302 | 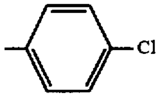 | Me | Me | Me | 1 | H | 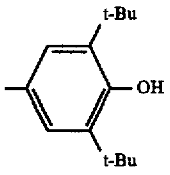 |

TABLE 22-continued
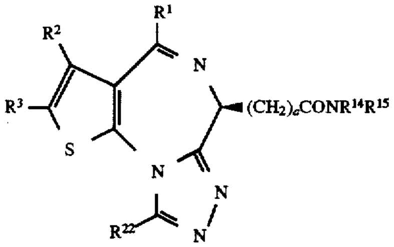
| No. | $R^1$ | $R^2$ | $R^3$ | $R^{22}$ | a | $R^{14}$ | $R^{15}$ |
|---|---|---|---|---|---|---|---|
| 303 | 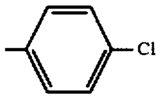 | Me | Me | Me | 1 | H | 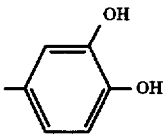 |
| 304 | 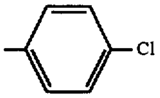 | Me | Me | Me | 1 | H | 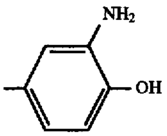 |
| 305 | 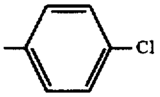 | Me | Me | Me | 1 | H | 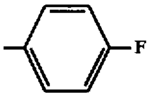 |
| 306 | 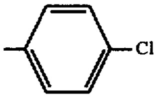 | Me | Me | Me | 1 | H | 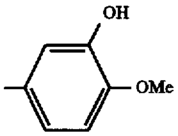 |
| 307 | 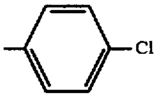 | Me | Me | Me | 1 | H | 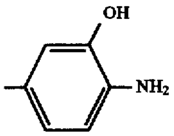 |
| 308 | 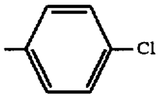 | Me | Me | Me | 1 | H | 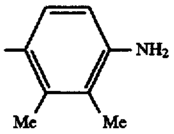 |
| 309 | 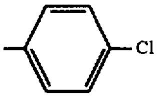 | Me | Me | Me | 1 | H | 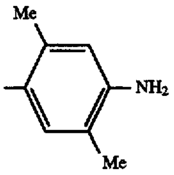 |
| 310 | 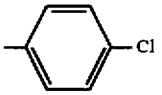 | Me | Me | Me | 1 | H | 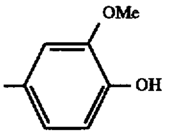 |
| 311 | 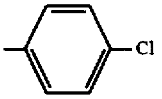 | Me | Me | Me | 1 | H | 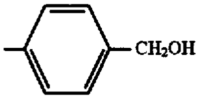 |

TABLE 22-continued
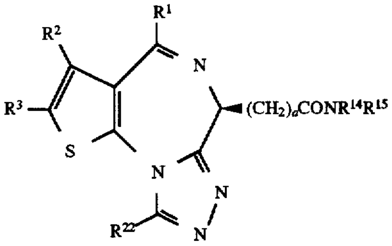
| No. | $R^1$ | $R^2$ | $R^3$ | $R^{22}$ | a | $R^{14}$ | $R^{15}$ |
|---|---|---|---|---|---|---|---|
| 312 | 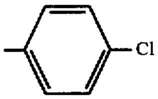 | Me | Me | Me | 1 | H | 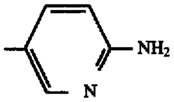 |
| 313 | 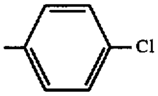 | Me | Me | Me | 1 | H | 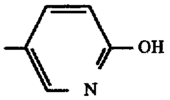 |
| 314 | 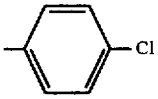 | Me | Me | Me | 1 | H | 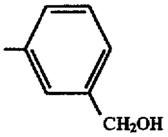 |
TABLE 23
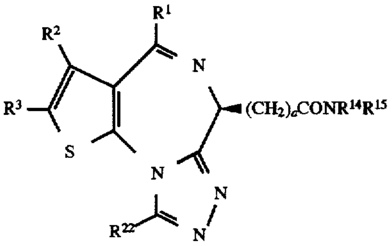
| No. | $R^1$ | $R^2$ | $R^3$ | $R^{22}$ | a | $R^{14}$ | $R^{15}$ |
|---|---|---|---|---|---|---|---|
| 321 | 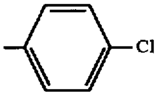 | Me | Me | Me | 2 | H | 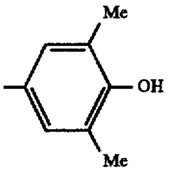 |
| 322 | 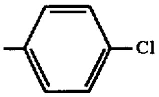 | Me | Me | Me | 2 | H | 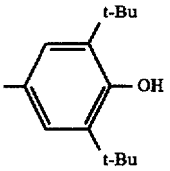 |
| 323 | 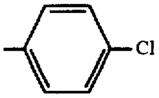 | Me | Me | Me | 2 | H | 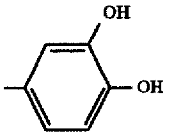 |

TABLE 23-continued
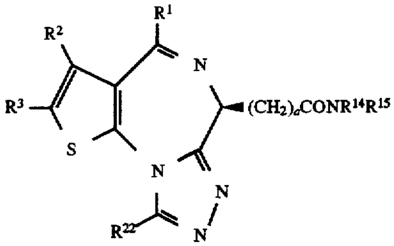
| No. | $R^1$ | $R^2$ | $R^3$ | $R^{22}$ | a | $R^{14}$ | $R^{15}$ |
|---|---|---|---|---|---|---|---|
| 324 | 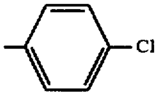 | Me | Me | Me | 2 | H | 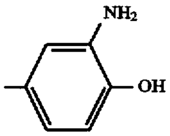 |
| 325 | 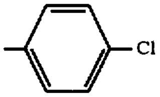 | Me | Me | Me | 2 | H | 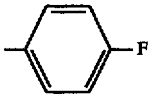 |
| 326 | 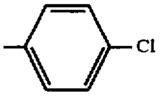 | Me | Me | Me | 2 | H | 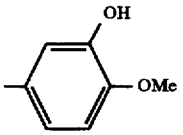 |
| 327 | 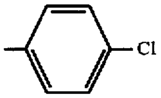 | Me | Me | Me | 2 | H | 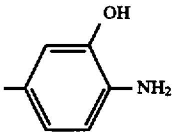 |
| 328 | 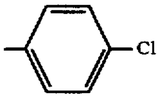 | Me | Me | Me | 2 | H | 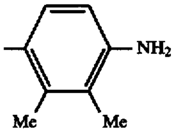 |
| 329 | 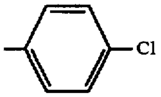 | Me | Me | Me | 2 | H | 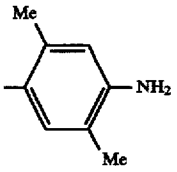 |
| 330 | 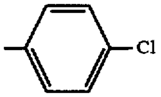 | Me | Me | Me | 2 | H | 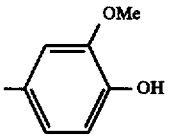 |
| 331 | 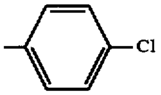 | Me | Me | Me | 2 | H | 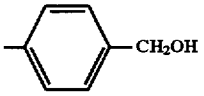 |
| 332 | 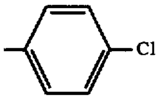 | Me | Me | Me | 2 | H | 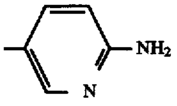 |

TABLE 23-continued
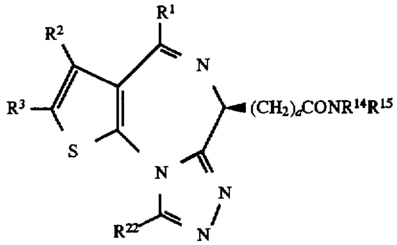
| No. | $R^1$ | $R^2$ | $R^3$ | $R^{22}$ | a | $R^{14}$ | $R^{15}$ |
|---|---|---|---|---|---|---|---|
| 333 | 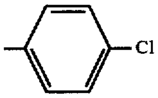 | Me | Me | Me | 2 | H | 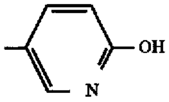 |
| 334 | 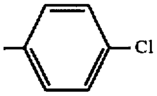 | Me | Me | Me | 2 | H | 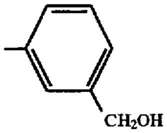 |
TABLE 24
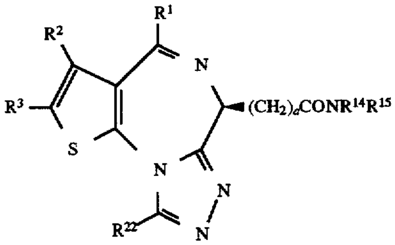
| No. | $R^1$ | $R^2$ | $R^3$ | $R^{22}$ | a | $R^{14}$ | $R^{15}$ |
|---|---|---|---|---|---|---|---|
| 341 | 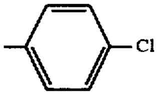 | Me | Me | Me | 3 | H | 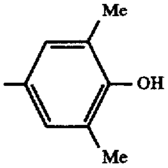 |
| 342 | 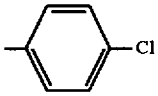 | Me | Me | Me | 3 | H | 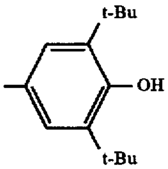 |
| 343 | 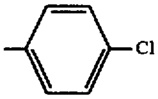 | Me | Me | Me | 3 | H | 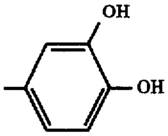 |

TABLE 24-continued
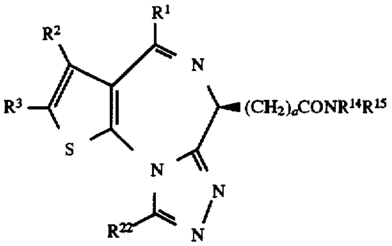
| No. | $R^1$ | $R^2$ | $R^3$ | $R^{22}$ | a | $R^{14}$ | $R^{15}$ |
|---|---|---|---|---|---|---|---|
| 344 | 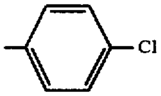 | Me | Me | Me | 3 | H | 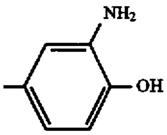 |
| 345 | 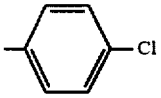 | Me | Me | Me | 3 | H | 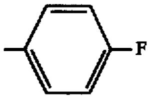 |
| 346 | 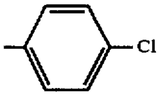 | Me | Me | Me | 3 | H | 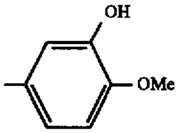 |
| 347 | 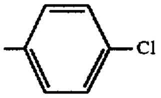 | Me | Me | Me | 3 | H | 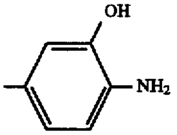 |
| 348 | 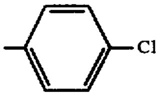 | Me | Me | Me | 3 | H | 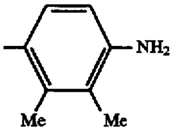 |
| 349 | 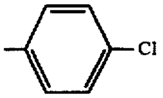 | Me | Me | Me | 3 | H | 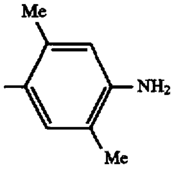 |
| 350 | 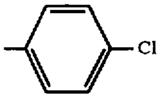 | Me | Me | Me | 3 | H | 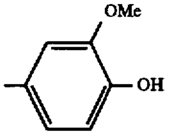 |
| 351 | 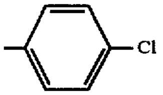 | Me | Me | Me | 3 | H | 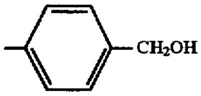 |
| 352 | 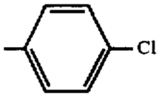 | Me | Me | Me | 3 | H | 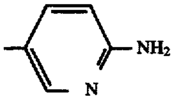 |

TABLE 24-continued
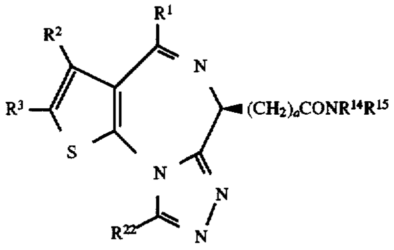
| No. | R¹ | R² | R³ | R²² | a | R¹⁴ | R¹⁵ |
|---|---|---|---|---|---|---|---|
| 353 | 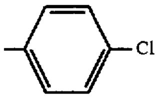 | Me | Me | Me | 3 | H | 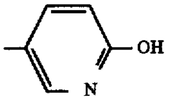 |
| 354 | 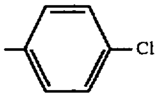 | Me | Me | Me | 3 | H | 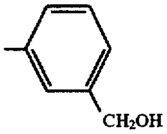 |
TABLE 25
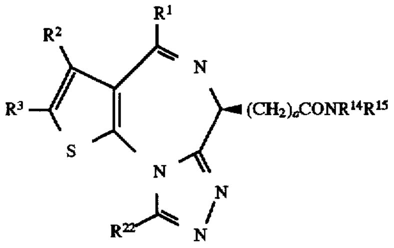
| No. | R¹ | R² | R³ | R²² | a | R¹⁴ | R¹⁵ |
|---|---|---|---|---|---|---|---|
| 361 | 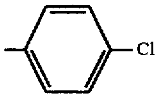 | Me | Me | MeO | 1 | H | 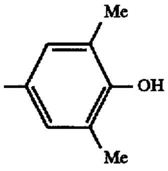 |
| 362 | 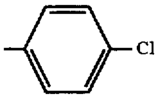 | Me | Me | MeO | 1 | H | 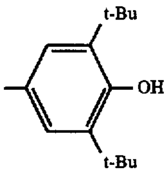 |
| 363 | 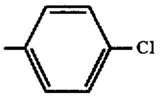 | Me | Me | MeO | 1 | H | 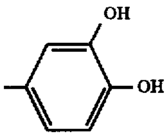 |
| 364 | 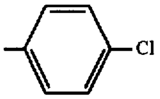 | Me | Me | MeO | 1 | H | 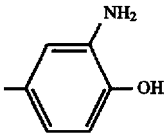 |

TABLE 25-continued
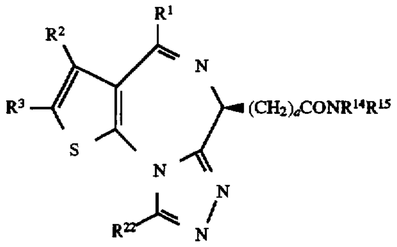
| No. | $R^1$ | $R^2$ | $R^3$ | $R^{22}$ | a | $R^{14}$ | $R^{15}$ |
|---|---|---|---|---|---|---|---|
| 365 | 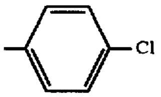 | Me | Me | MeO | 1 | H | 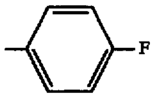 |
| 366 | 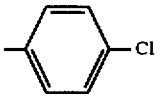 | Me | Me | MeO | 1 | H | 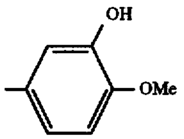 |
| 367 | 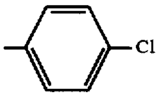 | Me | Me | MeO | 1 | H | 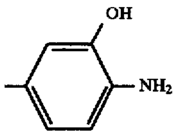 |
| 368 | 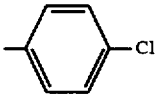 | Me | Me | MeO | 1 | H | 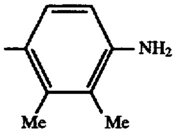 |
| 369 | 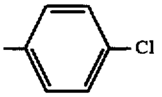 | Me | Me | MeO | 1 | H | 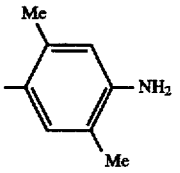 |
| 370 | 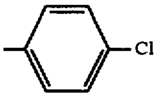 | Me | Me | MeO | 1 | H | 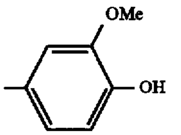 |
| 371 | 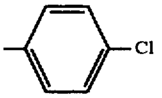 | Me | Me | MeO | 1 | H | 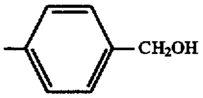 |
| 372 | 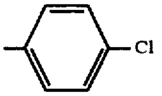 | Me | Me | MeO | 1 | H | 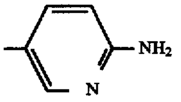 |
| 373 | 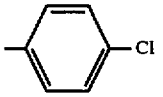 | Me | Me | MeO | 1 | H | 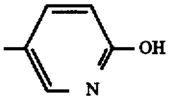 |

TABLE 25-continued
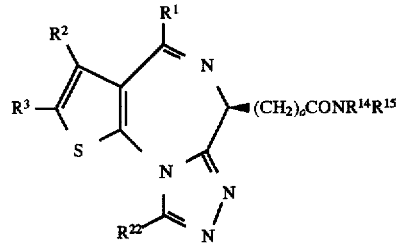
| No. | $R^1$ | $R^2$ | $R^3$ | $R^{22}$ | a | $R^{14}$ | $R^{15}$ |
|---|---|---|---|---|---|---|---|
| 374 | 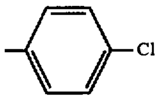 | Me | Me | MeO | 1 | H | 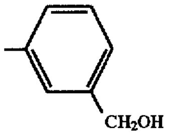 |
TABLE 26
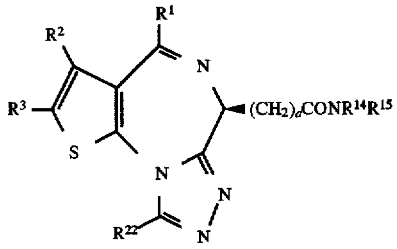
| No. | $R^1$ | $R^2$ | $R^3$ | $R^{22}$ | a | $R^{14}$ | $R^{15}$ |
|---|---|---|---|---|---|---|---|
| 401 | 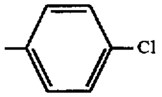 | Me | Me | Me | 1 | H | 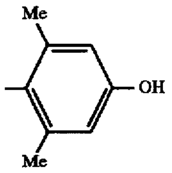 |
| 402 | 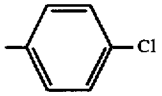 | Me | Me | Me | 1 | H | 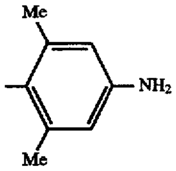 |
| 403 | 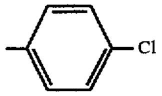 | Me | Me | Me | 1 | H | 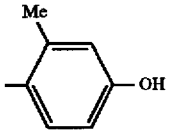 |
| 404 | 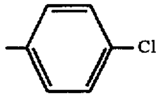 | Me | Me | Me | 1 | H | 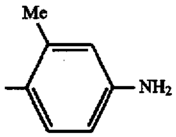 |

TABLE 26-continued
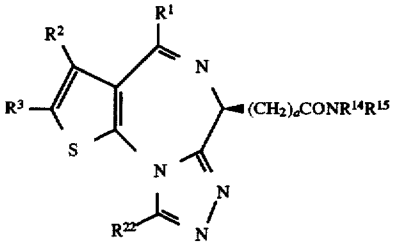
| No. | R¹ | $R^2$ | $R^3$ | $R^{22}$ | a | $R^{14}$ | $R^{15}$ |
|---|---|---|---|---|---|---|---|
| 405 | 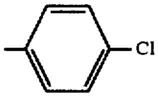 | Me | Me | Me | 1 | H | 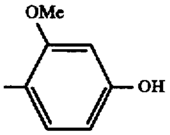 |
| 406 | 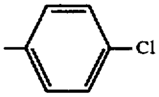 | Me | Me | Me | 1 | H | 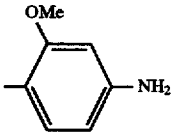 |
TABLE 27
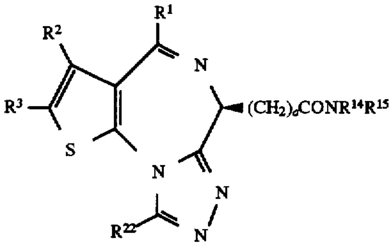
| No. | $R^1$ | $R^2$ | $R^3$ | $R^{22}$ | a | $R^{14}$ | $R^{15}$ |
|---|---|---|---|---|---|---|---|
| 411 | 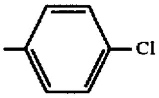 | Me | Me | Me | 2 | H | 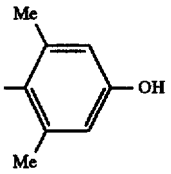 |
| 412 | 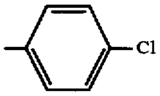 | Me | Me | Me | 2 | H | 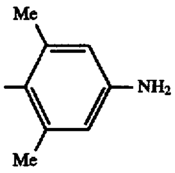 |
| 413 | 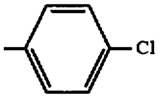 | Me | Me | Me | 2 | H | 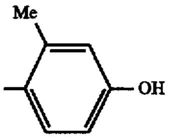 |
| 414 | 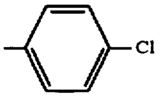 | Me | Me | Me | 2 | H | 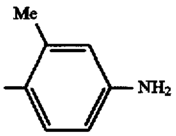 |

TABLE 27-continued
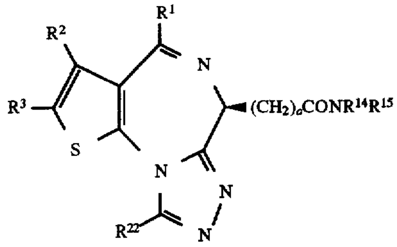
| No. | $R^1$ | $R^2$ | $R^3$ | $R^{22}$ | a | $R^{14}$ | $R^{15}$ |
|---|---|---|---|---|---|---|---|
| 415 | 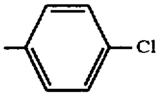 | Me | Me | Me | 2 | H | 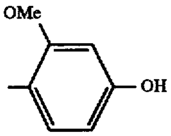 |
| 416 | 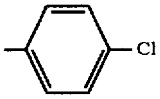 | Me | Me | Me | 2 | H | 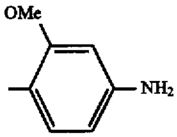 |
| 417 | 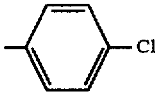 | Me | Me | Me | 2 | H | 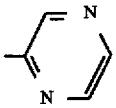 |
| 418 | 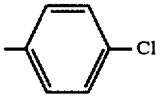 | Me | Me | Me | 2 | H | 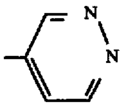 |
| 419 | 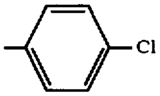 | Me | Me | Me | 2 | H | 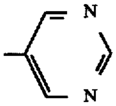 |
TABLE 28
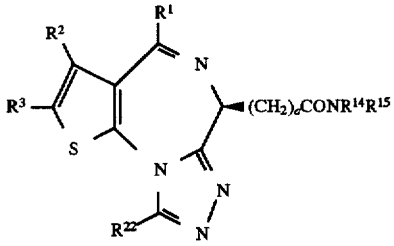
| No. | $R^1$ | $R^2$ | $R^3$ | $R^{22}$ | a | $R^{14}$ | $R^{15}$ |
|---|---|---|---|---|---|---|---|
| 421 | 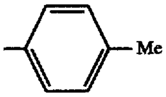 | Me | Me | Me | 1 | H | 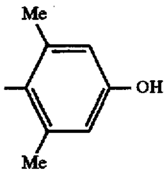 |

TABLE 28-continued
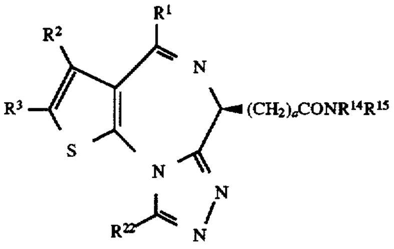
| No. | $R^1$ | $R^2$ | $R^3$ | $R^{22}$ | a | $R^{14}$ | $R^{15}$ |
|---|---|---|---|---|---|---|---|
| 422 | 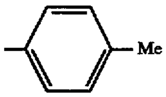 | Me | Me | Me | 1 | H | 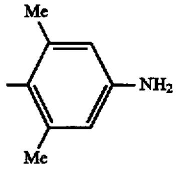 |
| 423 | 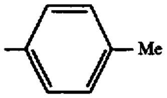 | Me | Me | Me | 1 | H | 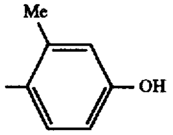 |
| 424 | 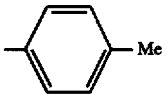 | Me | Me | Me | 1 | H | 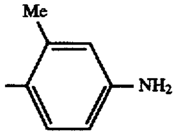 |
| 425 | 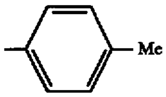 | Me | Me | Me | 1 | H | 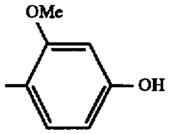 |
| 426 | 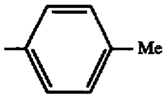 | Me | Me | Me | 1 | H | 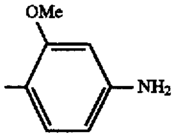 |
| 427 | 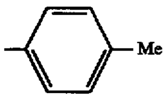 | Me | Me | Me | 1 | H | 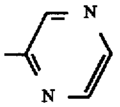 |
| 428 | 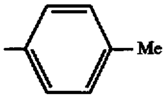 | Me | Me | Me | 1 | H | 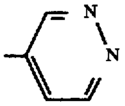 |
| 429 | 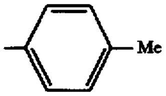 | Me | Me | Me | 1 | H | 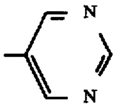 |

TABLE 29
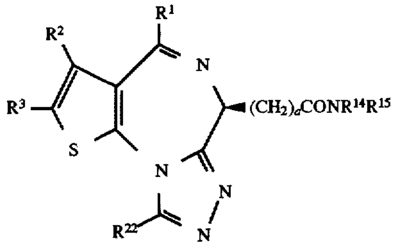
| No. | $R^1$ | $R^2$ | $R^3$ | $R^{22}$ | a | $R^{14}$ | $R^{15}$ |
|---|---|---|---|---|---|---|---|
| 431 | 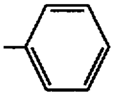 | Me | Me | Me | 1 | H | 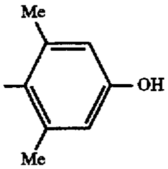 |
| 432 | 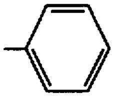 | Me | Me | Me | 1 | H | 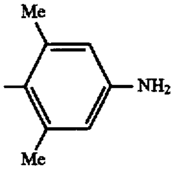 |
| 433 | 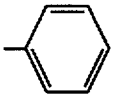 | Me | Me | Me | 1 | H | 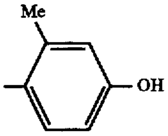 |
| 434 | 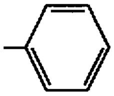 | Me | Me | Me | 1 | H | 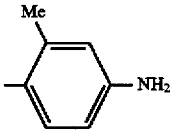 |
| 435 | 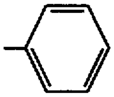 | Me | Me | Me | 1 | H | 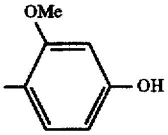 |
| 436 | 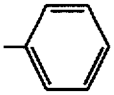 | Me | Me | Me | 1 | H | 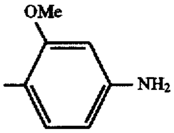 |
| 437 | 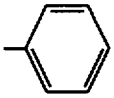 | Me | Me | Me | 1 | H | 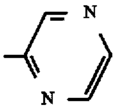 |
| 438 | 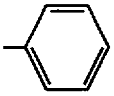 | Me | Me | Me | 1 | H | 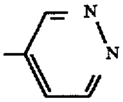 |
| 439 | 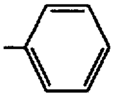 | Me | Me | Me | 1 | H | 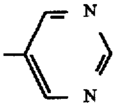 |

TABLE 30
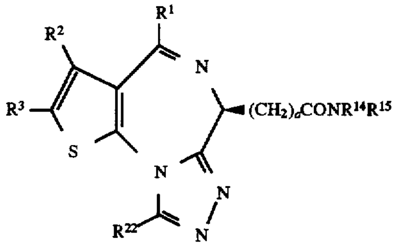
| No. | $R^1$ | $R^2$ | $R^3$ | $R^{22}$ | a | $R^{14}$ | $R^{15}$ |
|---|---|---|---|---|---|---|---|
| 441 | 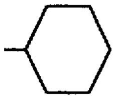 | Me | Me | Me | 1 | H | 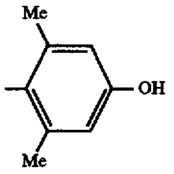 |
| 442 | 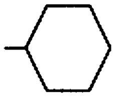 | Me | Me | Me | 1 | H | 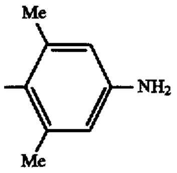 |
| 443 | 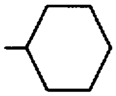 | Me | Me | Me | 1 | H | 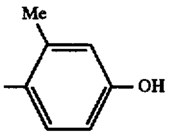 |
| 444 | 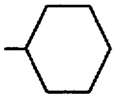 | Me | Me | Me | 1 | H | 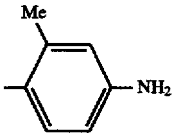 |
| 445 | 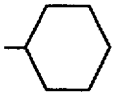 | Me | Me | Me | 1 | H | 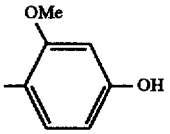 |
| 446 | 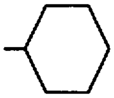 | Me | Me | Me | 1 | H | 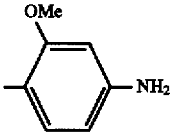 |
| 447 | 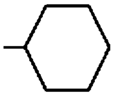 | Me | Me | Me | 1 | H | 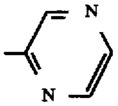 |
| 448 | 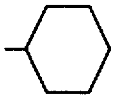 | Me | Me | Me | 1 | H | 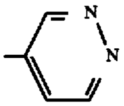 |
| 449 | 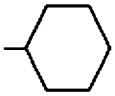 | Me | Me | Me | 1 | H | 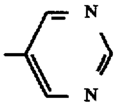 |

TABLE 31
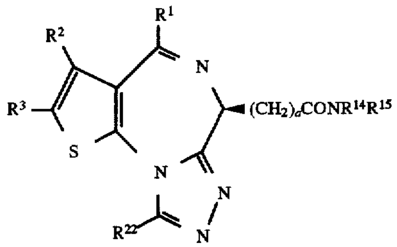
| No. | $R^1$ | $R^2$ | $R^3$ | $R^{22}$ | a | $R^{14}$ | $R^{15}$ |
|---|---|---|---|---|---|---|---|
| 451 | 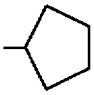 | Me | Me | Me | 1 | H | 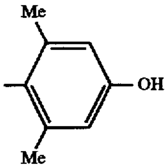 |
| 452 | 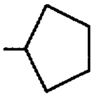 | Me | Me | Me | 1 | H | 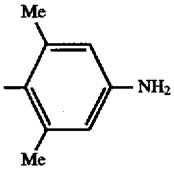 |
| 453 | 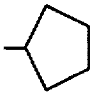 | Me | Me | Me | 1 | H | 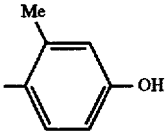 |
| 454 | 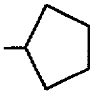 | Me | Me | Me | 1 | H | 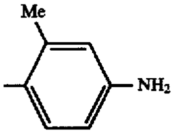 |
| 455 | 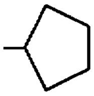 | Me | Me | Me | 1 | H | 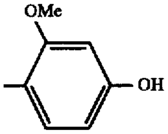 |
| 456 | 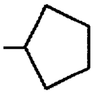 | Me | Me | Me | 1 | H | 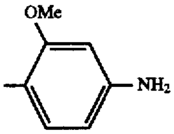 |
| 457 | 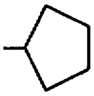 | Me | Me | Me | 1 | H | 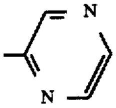 |
| 458 | 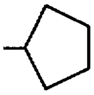 | Me | Me | Me | 1 | H | 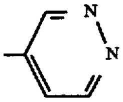 |
| 459 | 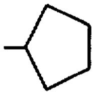 | Me | Me | Me | 1 | H | 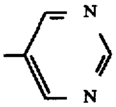 |
TABLE 32
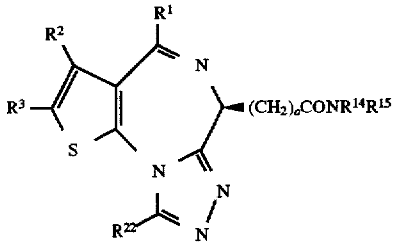
| No. | $R^1$ | $R^2$ | $R^3$ | $R^{22}$ | a | $R^{14}$ | $R^{15}$ |
|---|---|---|---|---|---|---|---|
| 461 | Me | Me | Me | Me | 1 | H | 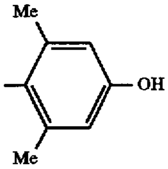 |
| 462 | Me | Me | Me | Me | 1 | H | 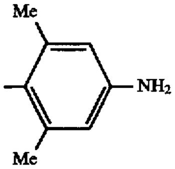 |
| 463 | Me | Me | Me | Me | 1 | H | 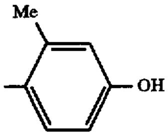 |
| 464 | Me | Me | Me | Me | 1 | H | 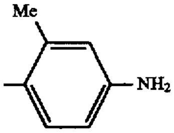 |
| 465 | Me | Me | Me | Me | 1 | H | 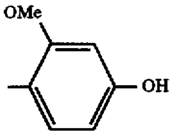 |
| 466 | Me | Me | Me | Me | 1 | H | 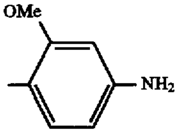 |
| 467 | Me | Me | Me | Me | 1 | H | 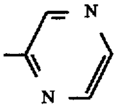 |
| 468 | Me | Me | Me | Me | 1 | H | 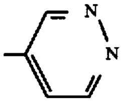 |
| 469 | Me | Me | Me | Me | 1 | H | 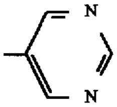 |

TABLE 33
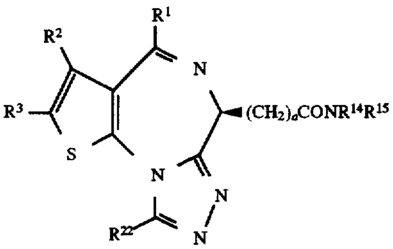
| No. | $R^1$ | $R^2$ | $R^3$ | $R^{22}$ | a | $R^{14}$ | $R^{15}$ |
|---|---|---|---|---|---|---|---|
| 501 | 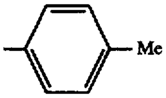 | Me | Me | Me | 1 | H | 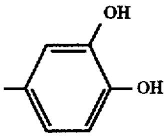 |
| 502 | 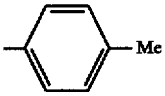 | Me | Me | Me | 1 | H | 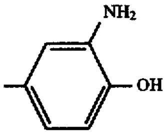 |
| 503 | 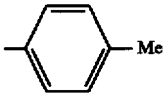 | Me | Me | Me | 1 | H | 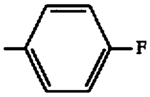 |
| 504 | 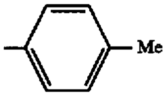 | Me | Me | Me | 1 | H | 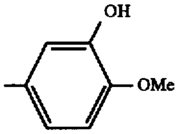 |
| 505 | 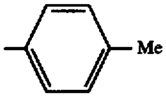 | Me | Me | Me | 1 | H | 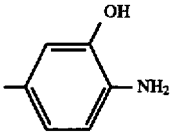 |
| 506 | 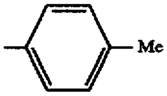 | Me | Me | Me | 1 | H | 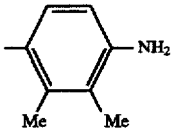 |
| 507 | 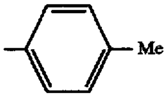 | Me | Me | Me | 1 | H | 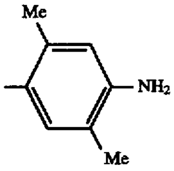 |
| 508 | 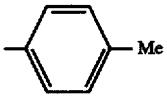 | Me | Me | Me | 1 | H | 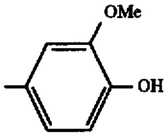 |
| 509 | 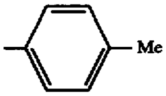 | Me | Me | Me | 1 | H | 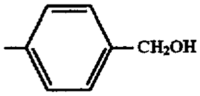 |

TABLE 33-continued
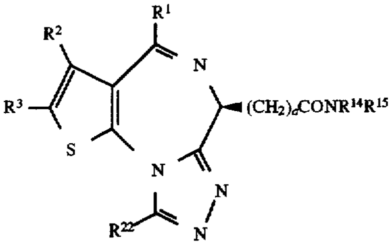
| No. | $R^1$ | $R^2$ | $R^3$ | $R^{22}$ | a | $R^{14}$ | $R^{15}$ |
|---|---|---|---|---|---|---|---|
| 510 | 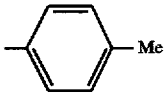 | Me | Me | Me | 1 | H | 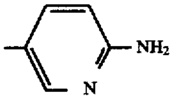 |
| 511 | 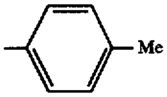 | Me | Me | Me | 1 | H | 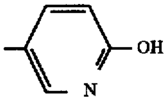 |
| 512 | 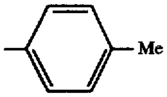 | Me | Me | Me | 1 | H | 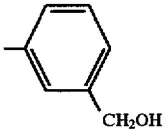 |
| 513 | 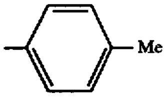 | Me | Me | Me | 1 | H | 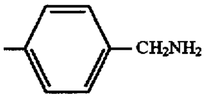 |
| 514 | 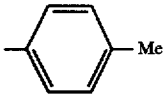 | Me | Me | Me | 1 | H | 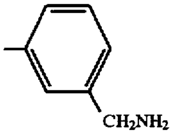 |
TABLE 34
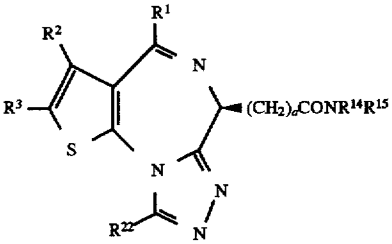
| No. | $R^1$ | $R^2$ | $R^3$ | $R^{22}$ | a | $R^{14}$ | $R^{15}$ |
|---|---|---|---|---|---|---|---|
| 521 | 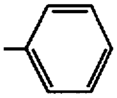 | Me | Me | Me | 1 | H | 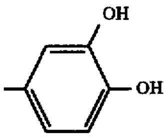 |
| 522 | 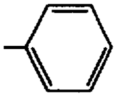 | Me | Me | Me | 1 | H | 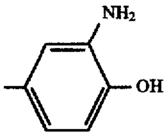 |

TABLE 34-continued
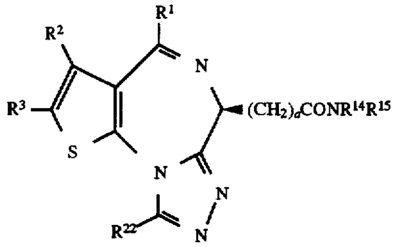
| No. | R1 | R2 | R3 | R22 | a | R14 | R15 |
|---|---|---|---|---|---|---|---|
| 523 | 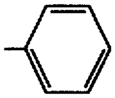 | Me | Me | Me | 1 | H | 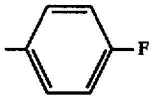 |
| 524 | 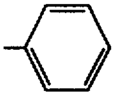 | Me | Me | Me | 1 | H | 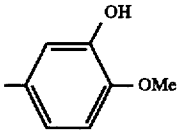 |
| 525 | 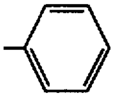 | Me | Me | Me | 1 | H | 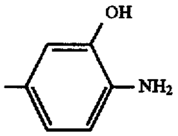 |
| 526 | 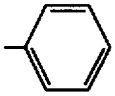 | Me | Me | Me | 1 | H | 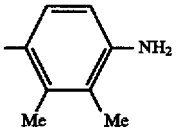 |
| 527 | 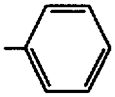 | Me | Me | Me | 1 | H | 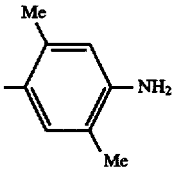 |
| 528 | 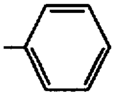 | Me | Me | Me | 1 | H | 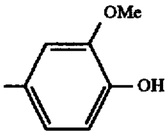 |
| 529 | 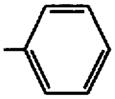 | Me | Me | Me | 1 | H | 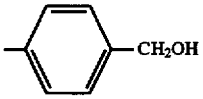 |
| 530 | 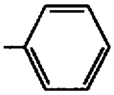 | Me | Me | Me | 1 | H | 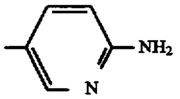 |
| 531 | 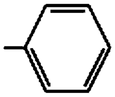 | Me | Me | Me | 1 | H | 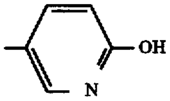 |
| 532 | 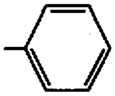 | Me | Me | Me | 1 | H | 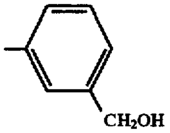 |

TABLE 34-continued
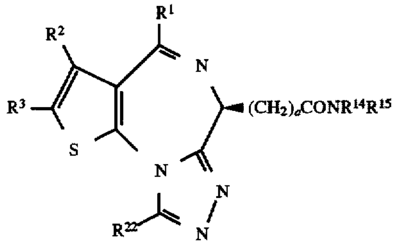
| No. | $R^1$ | $R^2$ | $R^3$ | $R^{22}$ | a | $R^{14}$ | $R^{15}$ |
|---|---|---|---|---|---|---|---|
| 533 | 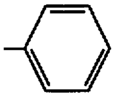 | Me | Me | Me | 1 | H | 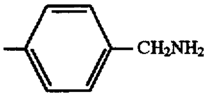 |
| 534 | 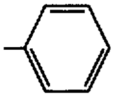 | Me | Me | Me | 1 | H | 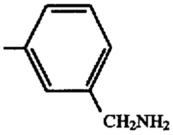 |
TABLE 35
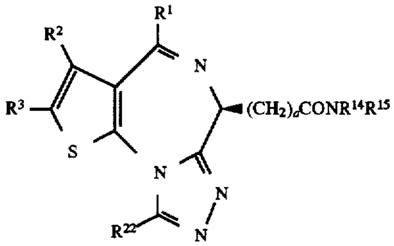
| No. | $R^1$ | $R^2$ | $R^3$ | $R^{22}$ | a | $R^{14}$ | $R^{15}$ |
|---|---|---|---|---|---|---|---|
| 541 | 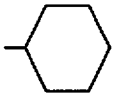 | Me | Me | Me | 1 | H | 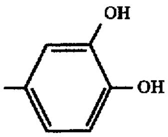 |
| 542 | 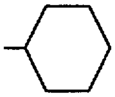 | Me | Me | Me | 1 | H | 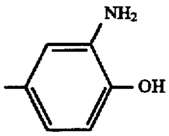 |
| 543 | 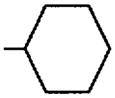 | Me | Me | Me | 1 | H | 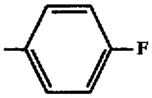 |
| 544 | 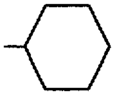 | Me | Me | Me | 1 | H | 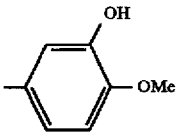 |

TABLE 35-continued
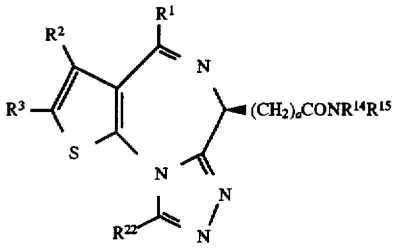
| No. | $R^1$ | $R^2$ | $R^3$ | $R^{22}$ | a | $R^{14}$ | $R^{15}$ |
|---|---|---|---|---|---|---|---|
| 545 | 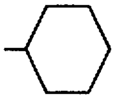 | Me | Me | Me | 1 | H | 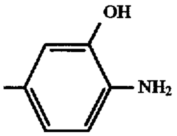 |
| 546 | 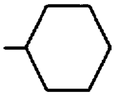 | Me | Me | Me | 1 | H | 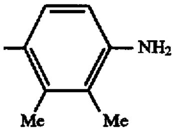 |
| 547 | 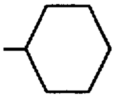 | Me | Me | Me | 1 | H | 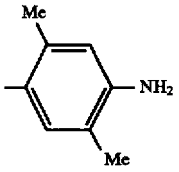 |
| 548 | 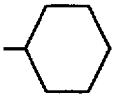 | Me | Me | Me | 1 | H | 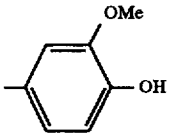 |
| 549 | 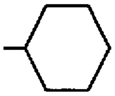 | Me | Me | Me | 1 | H | 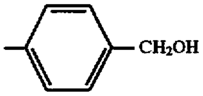 |
| 550 | 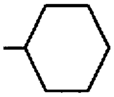 | Me | Me | Me | 1 | H | 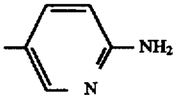 |
| 551 | 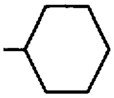 | Me | Me | Me | 1 | H | 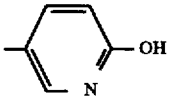 |
| 552 | 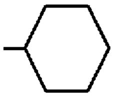 | Me | Me | Me | 1 | H | 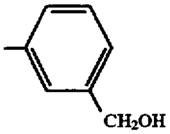 |
| 553 | 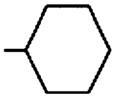 | Me | Me | Me | 1 | H | 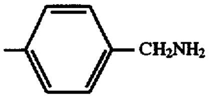 |

TABLE 35-continued
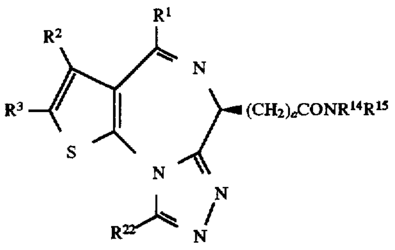
| No. | $R^1$ | $R^2$ | $R^3$ | $R^{22}$ | a | $R^{14}$ | $R^{15}$ |
|---|---|---|---|---|---|---|---|
| 554 | 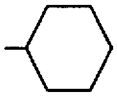 | Me | Me | Me | 1 | H | 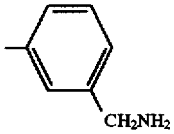 |
TABLE 36
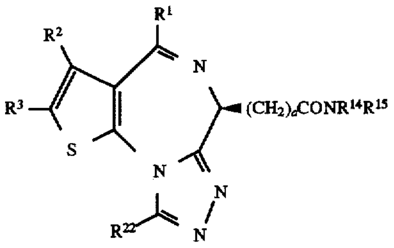
| No. | $R^1$ | $R^2$ | $R^3$ | $R^{22}$ | a | $R^{14}$ | $R^{15}$ |
|---|---|---|---|---|---|---|---|
| 561 | 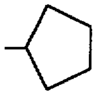 | Me | Me | Me | 1 | H | 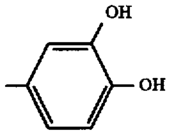 |
| 562 | 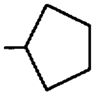 | Me | Me | Me | 1 | H | 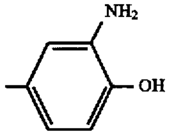 |
| 563 | 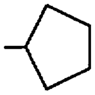 | Me | Me | Me | 1 | H | 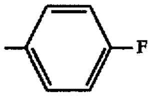 |
| 564 | 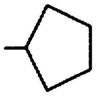 | Me | Me | Me | 1 | H | 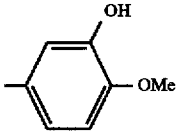 |
| 565 | 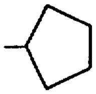 | Me | Me | Me | 1 | H | 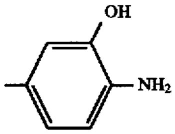 |

TABLE 36-continued
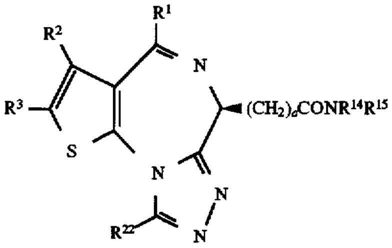
| No. | $R^1$ | $R^2$ | $R^3$ | $R^{22}$ | a | $R^{14}$ | $R^{15}$ |
|---|---|---|---|---|---|---|---|
| 566 | 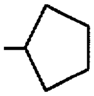 | Me | Me | Me | 1 | H | 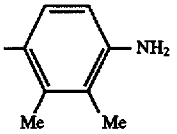 |
| 567 | 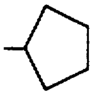 | Me | Me | Me | 1 | H | 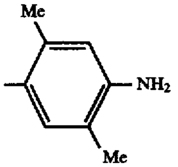 |
| 568 | 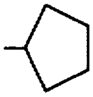 | Me | Me | Me | 1 | H | 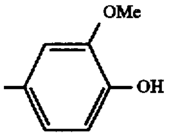 |
| 569 | 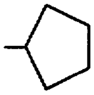 | Me | Me | Me | 1 | H | 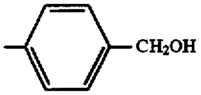 |
| 570 | 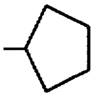 | Me | Me | Me | 1 | H | 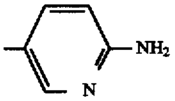 |
| 571 | 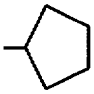 | Me | Me | Me | 1 | H | 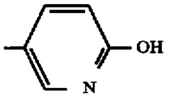 |
| 572 | 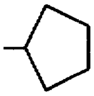 | Me | Me | Me | 1 | H | 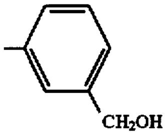 |
| 573 | 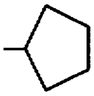 | Me | Me | Me | i | H | 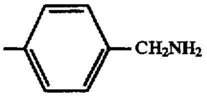 |
| 574 | 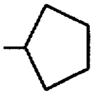 | Me | Me | Me | 1 | H | 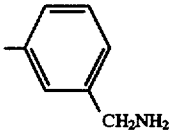 |

TABLE 37
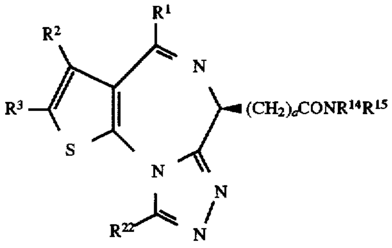
| No. | $R^1$ | $R^2$ | $R^3$ | $R^{22}$ | a | $R^{14}$ | $R^{15}$ |
|---|---|---|---|---|---|---|---|
| 581 | Me | Me | Me | Me | 1 | H | 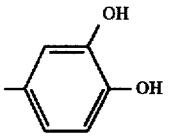 |
| 582 | Me | Me | Me | Me | 1 | H | 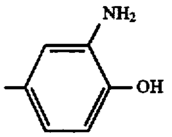 |
| 583 | Me | Me | Me | Me | 1 | H | 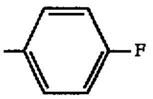 |
| 584 | Me | Me | Me | Me | 1 | H | 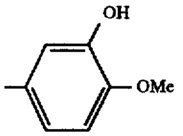 |
| 585 | Me | Me | Me | Me | 1 | H | 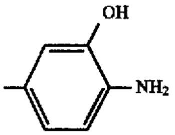 |
| 586 | Me | Me | Me | Me | 1 | H | 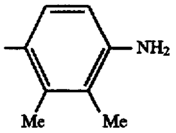 |
| 587 | Me | Me | Me | Me | 1 | H | 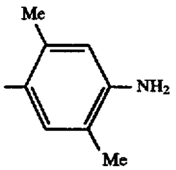 |
TABLE 37-continued
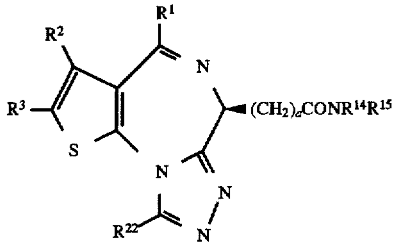
| No. | $R^1$ | $R^2$ | $R^3$ | $R^{22}$ | a | $R^{14}$ | $R^{15}$ |
|---|---|---|---|---|---|---|---|
| 588 | Me | Me | Me | Me | 1 | H | 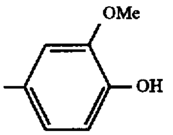 |
| 589 | Me | Me | Me | Me | 1 | H | 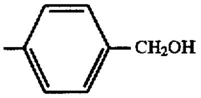 |
| 590 | Me | Me | Me | Me | 1 | H | 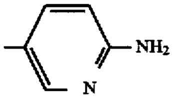 |
| 591 | Me | Me | Me | Me | 1 | H | 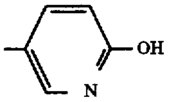 |
| 592 | Me | Me | Me | Me | 1 | H | 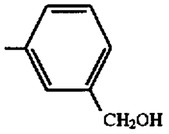 |
| 593 | Me | Me | Me | Me | 1 | H | 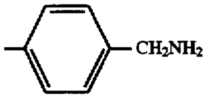 |
| 594 | Me | Me | Me | Me | 1 | H | 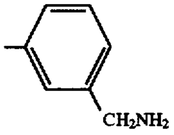 |

TABLE 38
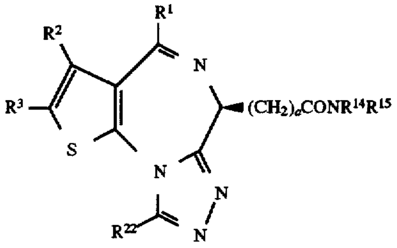
| No. | $R^1$ | $R^2$ | $R^3$ | $R^{22}$ | a | $R^{14}$ | $R^{15}$ |
|---|---|---|---|---|---|---|---|
| 601 | 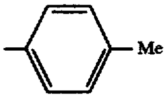 | Me | Me | Me | 1 | H | H |
| 602 | 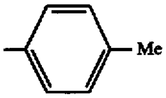 | Me | Me | Me | 1 | H | Me |
| 603 | 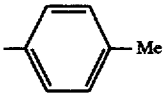 | Me | Me | Me | 1 | Me | Me |
| 604 | 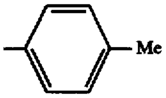 | Me | Me | Me | 1 | H | 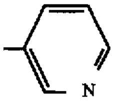 |
| 605 | 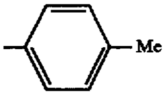 | Me | Me | Me | 1 | $-CH_2CH_2N(Me)CH_2CH_2-$ | |
| 606 | 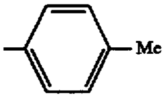 | Me | Me | Me | 1 | H | $CH_2CH_2OH$ |
| 607 | 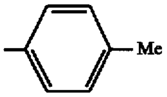 | Me | Me | Me | 1 | H | 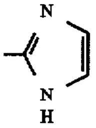 |
| 608 | 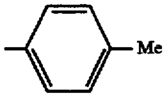 | Me | Me | Me | 1 | $-CH{=}CHC(NH_2){=}N-$ | |
| 609 | 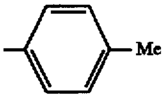 | Me | Me | Me | 1 | H | $CH_2CH_2OMe$ |
| 610 | 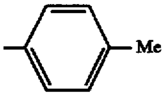 | Me | Me | Me | 1 | H | 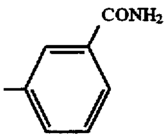 |
| 611 | 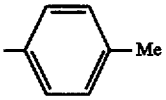 | Me | Me | Me | 1 | H | OH |

TABLE 38-continued
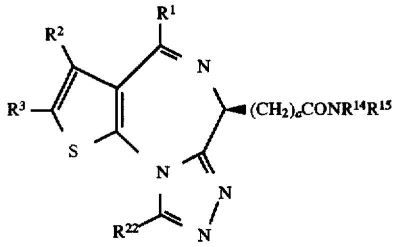
| No. | $R^1$ | $R^2$ | $R^3$ | $R^{22}$ | a | $R^{14}$ | $R^{15}$ |
|---|---|---|---|---|---|---|---|
| 612 | 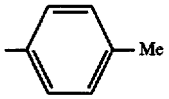 | Me | Me | Me | 1 | H | $CH_2CH_2NH_2$ |
| 613 | 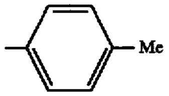 | Me | Me | Me | 1 | H | 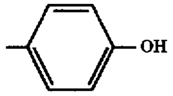 |
| 614 | 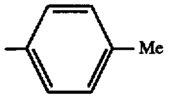 | Me | Me | Me | 1 | H | 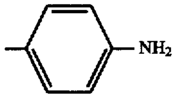 |
| 615 | 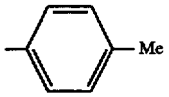 | Me | Me | Me | 1 | H | 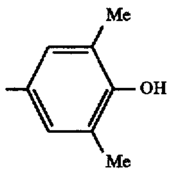 |
| 616 | 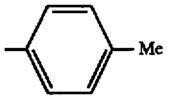 | Me | Me | Me | 1 | H | 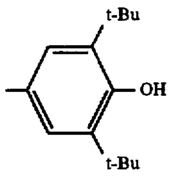 |
TABLE 39
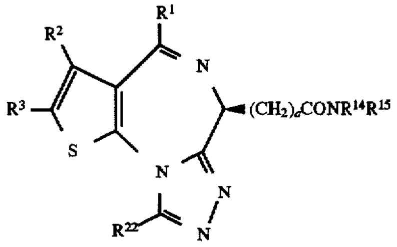
| No. | $R^1$ | $R^2$ | $R^3$ | $R^{22}$ | a | $R^{14}$ | $R^{15}$ |
|---|---|---|---|---|---|---|---|
| 621 | 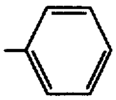 | Me | Me | Me | 1 | H | H |
| 622 | 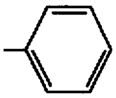 | Me | Me | Me | 1 | H | Me |

TABLE 39-continued
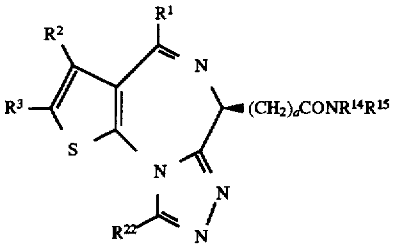
| No. | $R^1$ | $R^2$ | $R^3$ | $R^{22}$ | a | $R^{14}$ | $R^{15}$ |
|---|---|---|---|---|---|---|---|
| 623 | 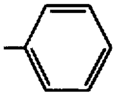 | Me | Me | Me | 1 | Me | Me |
| 624 | 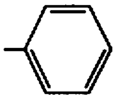 | Me | Me | Me | 1 | H | 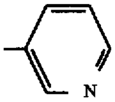 |
| 625 | 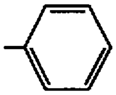 | Me | Me | Me | 1 | $-CH_2CH_2N(Me)CH_2CH_2-$ | |
| 626 | 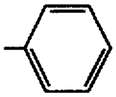 | Me | Me | Me | 1 | H | $CH_2CH_2OH$ |
| 627 | 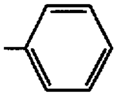 | Me | Me | Me | 1 | H | 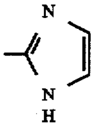 |
| 628 | 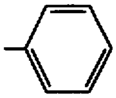 | Me | Me | Me | 1 | $-CH{=}CHC(NH_2){=}N-$ | |
| 629 | 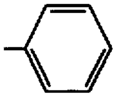 | Me | Me | Me | 1 | H | $CH_2CH_2OMe$ |
| 630 | 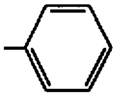 | Me | Me | Me | 1 | H | 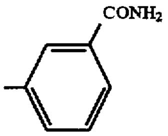 |
| 631 | 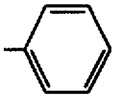 | Me | Me | Me | 1 | H | OH |
| 632 | 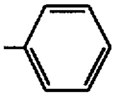 | Me | Me | Me | 1 | H | $CH_2CH_2NH_2$ |
| 633 | 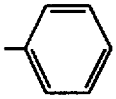 | Me | Me | Me | 1 | H | 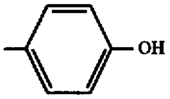 |

TABLE 39-continued
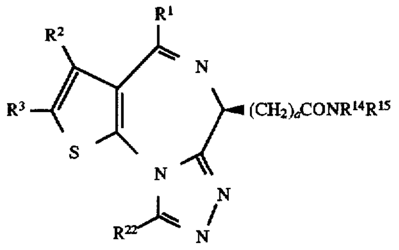
| No. | $R^1$ | $R^2$ | $R^3$ | $R^{22}$ | a | $R^{14}$ | $R^{15}$ |
|---|---|---|---|---|---|---|---|
| 634 | 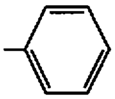 | Me | Me | Me | 1 | H | 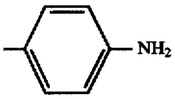 |
| 635 | 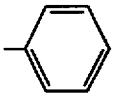 | Me | Me | Me | 1 | H | 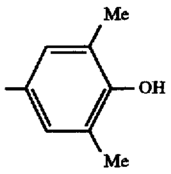 |
| 636 | 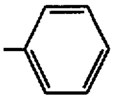 | Me | Me | Me | 1 | H | 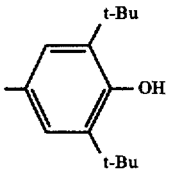 |
TABLE 40
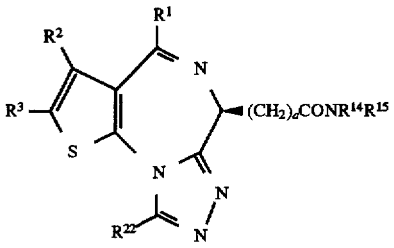
| No. | $R^1$ | $R^2$ | $R^3$ | $R^{22}$ | a | $R^{14}$ | $R^{15}$ |
|---|---|---|---|---|---|---|---|
| 641 | 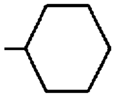 | Me | Me | Me | 1 | H | H |
| 642 | 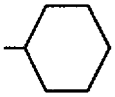 | Me | Me | Me | 1 | H | Me |
| 643 | 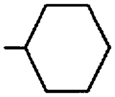 | Me | Me | Me | 1 | Me | Me |
| 644 | 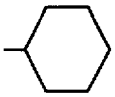 | Me | Me | Me | 1 | H | 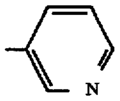 |

TABLE 40-continued
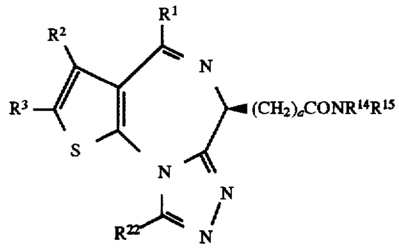
| No. | $R^1$ | $R^2$ | $R^3$ | $R^{22}$ | a | $R^{14}$ | $R^{15}$ |
|---|---|---|---|---|---|---|---|
| 645 | 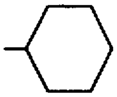 | Me | Me | Me | 1 | $-CH_2CH_2N(Me)CH_2CH_2-$ | |
| 646 | 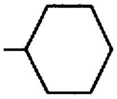 | Me | Me | Me | 1 | H | $CH_2CH_2OH$ |
| 647 | 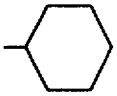 | Me | Me | Me | 1 | H | 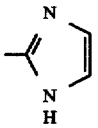 |
| 648 | 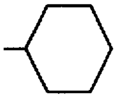 | Me | Me | Me | 1 | $-CH{=}CHC(NH_2){=}N-$ | |
| 649 | 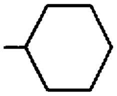 | Me | Me | Me | 1 | H | $CH_2CH_2OMe$ |
| 650 | 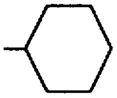 | Me | Me | Me | 1 | H | 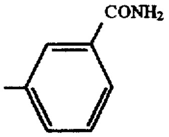 |
| 651 | 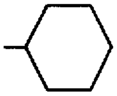 | Me | Me | Me | 1 | H | OH |
| 652 | 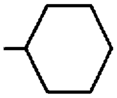 | Me | Me | Me | 1 | H | $CH_2CH_2NH_2$ |
| 653 | 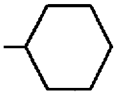 | Me | Me | Me | 1 | H | 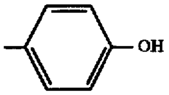 |
| 654 | 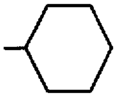 | Me | Me | Me | 1 | H | 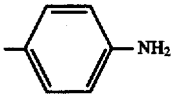 |

TABLE 40-continued
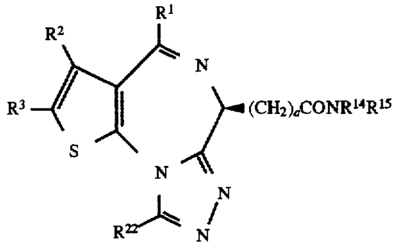
| No. | $R^1$ | $R^2$ | $R^3$ | $R^{22}$ | a | $R^{14}$ | $R^{15}$ |
|---|---|---|---|---|---|---|---|
| 655 | 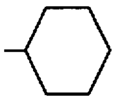 | Me | Me | Me | 1 | H | 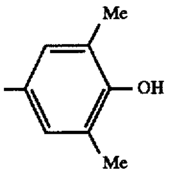 |
| 656 | 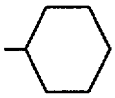 | Me | Me | Me | 1 | H | 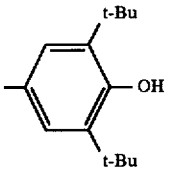 |
TABLE 41
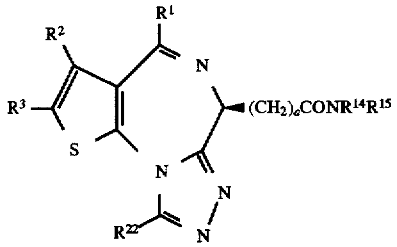
| No. | $R^1$ | $R^2$ | $R^3$ | $R^{22}$ | a | $R^{14}$ | $R^{15}$ |
|---|---|---|---|---|---|---|---|
| 661 | 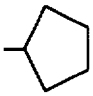 | Me | Me | Me | 1 | H | H |
| 662 | 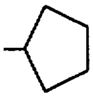 | Me | Me | Me | 1 | H | Me |
| 663 | 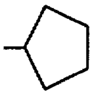 | Me | Me | Me | 1 | Me | Me |
| 664 | 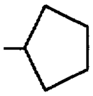 | Me | Me | Me | 1 | H | 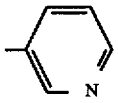 |
| 665 | 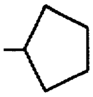 | Me | Me | Me | 1 | $-CH_2CH_2N(Me)CH_2CH_2-$ | |

TABLE 41-continued
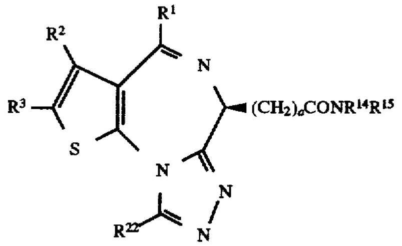
| No. | $R^1$ | $R^2$ | $R^3$ | $R^{22}$ | a | $R^{14}$ | $R^{15}$ |
|---|---|---|---|---|---|---|---|
| 666 | 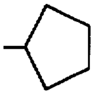 | Me | Me | Me | 1 | H | $CH_2CH_2OH$ |
| 667 | 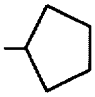 | Me | Me | Me | 1 | H | 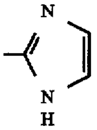 |
| 668 | 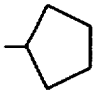 | Me | Me | Me | 1 | $-CH=CHC(NH_2)=N-$ | |
| 669 | 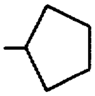 | Me | Me | Me | 1 | H | $CH_2CH_2OMe$ |
| 670 | 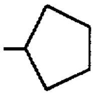 | Me | Me | Me | 1 | H | 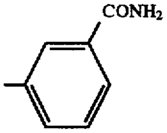 |
| 671 | 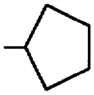 | Me | Me | Me | 1 | H | OH |
| 672 | 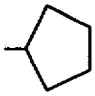 | Me | Me | Me | 1 | H | $CH_2CH_2NH_2$ |
| 673 | 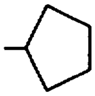 | Me | Me | Me | 1 | H | 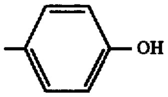 |
| 674 | 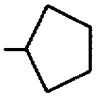 | Me | Me | Me | 1 | H | 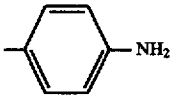 |
| 675 | 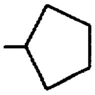 | Me | Me | Me | 1 | H | 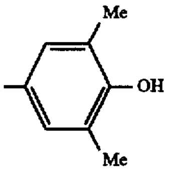 |

TABLE 41-continued

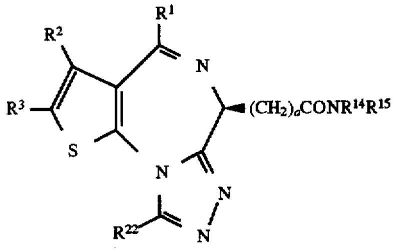

| No. | $R^1$ | $R^2$ | $R^3$ | $R^{22}$ | a | $R^{14}$ | $R^{15}$ |
|---|---|---|---|---|---|---|---|
| 676 | 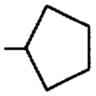 | Me | Me | Me | 1 | H | 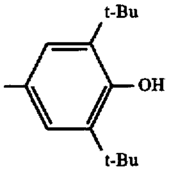 |

TABLE 42

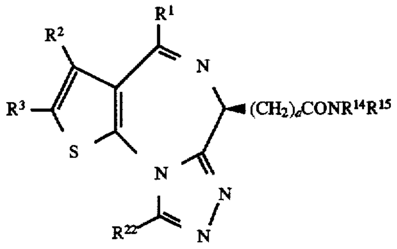

| No. | $R^1$ | $R^2$ | $R^3$ | $R^{22}$ | a | $R^{14}$ | $R^{15}$ |
|---|---|---|---|---|---|---|---|
| 681 | Me | Me | Me | Me | 1 | H | H |
| 682 | Me | Me | Me | Me | 1 | H | Me |
| 683 | Me | Me | Me | Me | 1 | Me | Me |
| 684 | Me | Me | Me | Me | 1 | H | 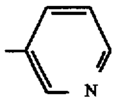 |
| 685 | Me | Me | Me | Me | 1 | $-CH_2CH_2N(Me)CH_2CH_2-$ | |
| 686 | Me | Me | Me | Me | 1 | H | $CH_2CH_2OH$ |
| 687 | Me | Me | Me | Me | 1 | H | 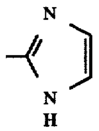 |
| 688 | Me | Me | Me | Me | 1 | $-CH{=}CHC(NH_2){=}N-$ | |
| 689 | Me | Me | Me | Me | 1 | H | $CH_2CH_2OMe$ |
| 690 | Me | Me | Me | Me | 1 | H | 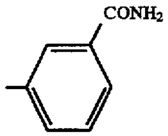 |
| 691 | Me | Me | Me | Me | 1 | H | OH |
| 692 | Me | Me | Me | Me | 1 | H | $CH_2CH_2NH_2$ |

TABLE 42-continued

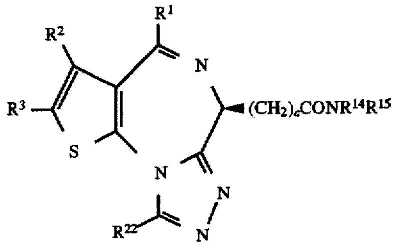

| No. | $R^1$ | $R^2$ | $R^3$ | $R^{22}$ | a | $R^{14}$ | $R^{15}$ |
|---|---|---|---|---|---|---|---|
| 693 | Me | Me | Me | Me | 1 | H | 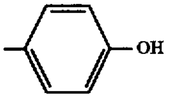 |
| 694 | Me | Me | Me | Me | 1 | H | 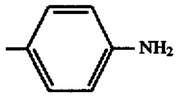 |
| 695 | Me | Me | Me | Me | 1 | H | 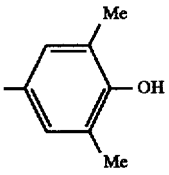 |
| 696 | Me | Me | Me | Me | 1 | H | 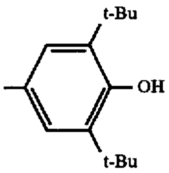 |

TABLE 43
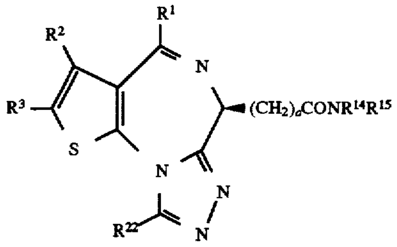
| No. | $R^1$ | $R^2$ | $R^3$ | $R^{22}$ | a | $R^{14}$ | $R^{15}$ |
|---|---|---|---|---|---|---|---|
| 701 | 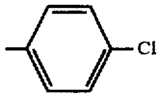 | Me | Me | Me | 1 | H | $CH_2CH_2CH_2NH_2$ |
| 702 | 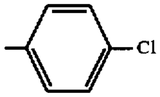 | Me | Me | Me | 1 | H | $CH_2CH_2CH_2CH_2NH_2$ |
| 703 | 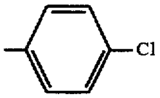 | Me | Me | Me | 1 | H | 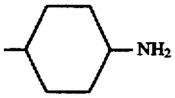 |
| 704 | 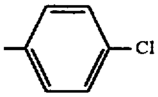 | Me | Me | Me | 1 | H | 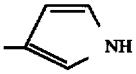 |
| 705 | 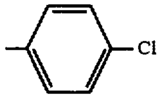 | Me | Me | Me | 1 | H | 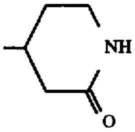 |
| 706 | 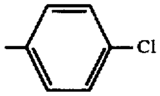 | Me | Me | Me | 1 | H | 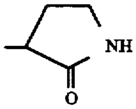 |
| 707 | 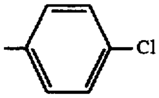 | Me | Me | Me | 1 | H | 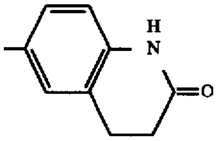 |
| 708 | 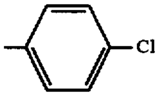 | Me | Me | Me | 1 | H | 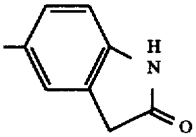 |
| 709 | 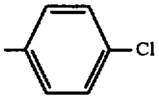 | Me | Me | Me | 1 | H | 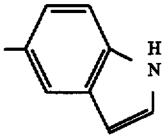 |
| 710 | 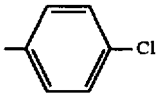 | Me | Me | Me | 1 | H | 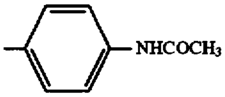 |

TABLE 44
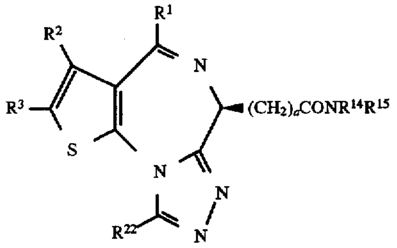
| No. | $R^1$ | $R^2$ | $R^3$ | $R^{22}$ | a | $R^{14}$ | $R^{15}$ |
|---|---|---|---|---|---|---|---|
| 711 | 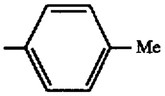 | Me | Me | Me | 1 | H | $CH_2CH_2CH_2NH_2$ |
| 712 | 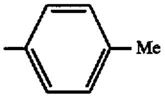 | Me | Me | Me | 1 | H | $CH_2CH_2CH_2CH_2NH_2$ |
| 713 | 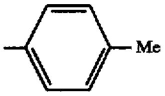 | Me | Me | Me | 1 | H | 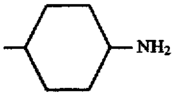 |
| 714 | 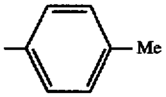 | Me | Me | Me | 1 | H | 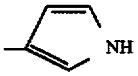 |
| 715 | 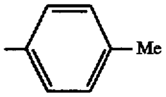 | Me | Me | Me | 1 | H | 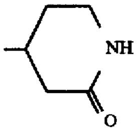 |
| 716 | 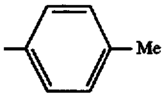 | Me | Me | Me | 1 | H | 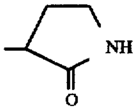 |
| 717 | 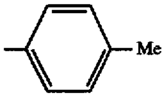 | Me | Me | Me | 1 | H | 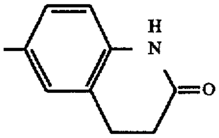 |
| 718 | 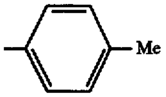 | Me | Me | Me | 1 | H | 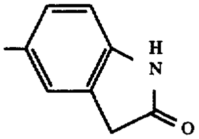 |
| 719 | 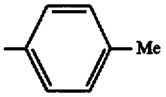 | Me | Me | Me | 1 | H | 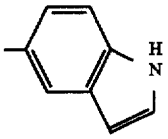 |
| 720 | 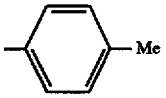 | Me | Me | Me | 1 | H | 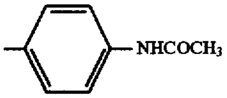 |

TABLE 45
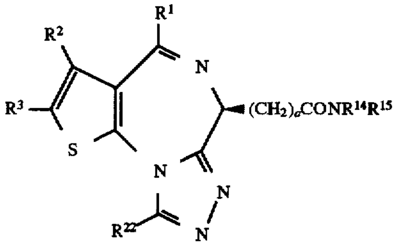
| No. | $R^1$ | $R^2$ | $R^3$ | $R^{22}$ | a | $R^{14}$ | $R^{15}$ |
|---|---|---|---|---|---|---|---|
| 721 | 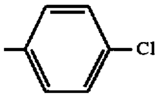 | Me | Me | MeO | 1 | H | $CH_2CH_2CH_2NH_2$ |
| 722 | 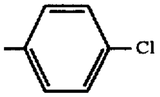 | Me | Me | MeO | 1 | H | $CH_2CH_2CH_2CH_2NH_2$ |
| 723 | 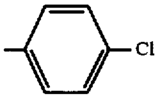 | Me | Me | MeO | 1 | H | 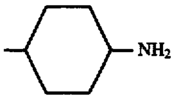 |
| 724 | 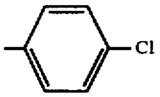 | Me | Me | MeO | 1 | H | 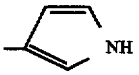 |
| 725 | 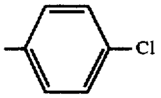 | Me | Me | MeO | 1 | H | 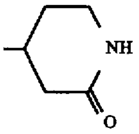 |
| 726 | 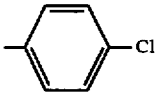 | Me | Me | MeO | 1 | H | 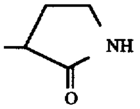 |
| 727 | 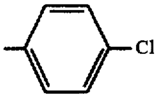 | Me | Me | MeO | 1 | H | 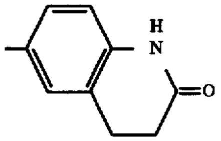 |
| 728 | 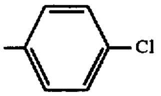 | Me | Me | MeO | 1 | H | 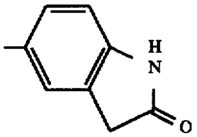 |
| 729 | 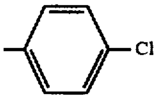 | Me | Me | MeO | 1 | H | 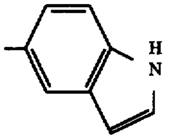 |
| 730 | 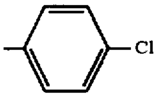 | Me | Me | MeO | 1 | H | 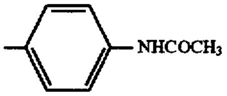 |

TABLE 46
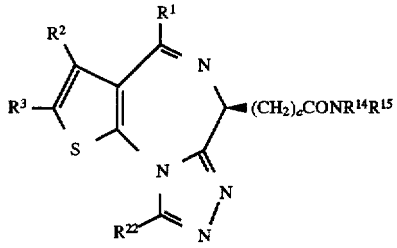
| No. | $R^1$ | $R^2$ | $R^3$ | $R^{22}$ | a | $R^{14}$ | $R^{15}$ |
|---|---|---|---|---|---|---|---|
| 731 | 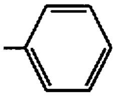 | Me | Me | Me | 1 | H | $CH_2CH_2CH_2NH_2$ |
| 732 | 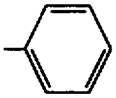 | Me | Me | Me | 1 | H | $CH_2CH_2CH_2CH_2NH_2$ |
| 733 | 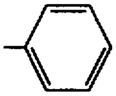 | Me | Me | Me | 1 | H | 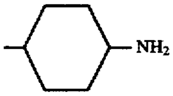 |
| 734 | 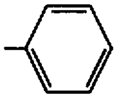 | Me | Me | Me | 1 | H | 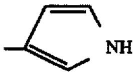 |
| 735 | 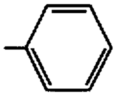 | Me | Me | Me | 1 | H | 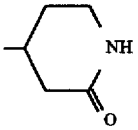 |
| 736 | 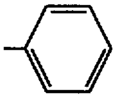 | Me | Me | Me | 1 | H | 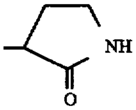 |
| 737 | 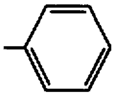 | Me | Me | Me | 1 | H | 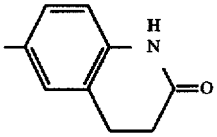 |
| 738 | 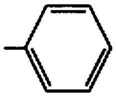 | Me | Me | Me | 1 | H | 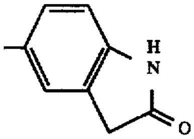 |
| 739 | 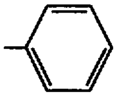 | Me | Me | Me | 1 | H | 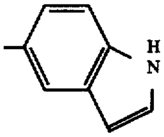 |
| 740 | 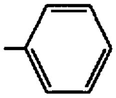 | Me | Me | Me | 1 | H | 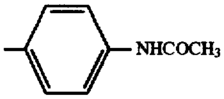 |

TABLE 47
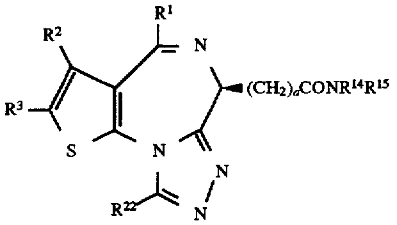
| No. | $R^1$ | $R^2$ | $R^3$ | $R^{22}$ | a | $R^{14}$ | $R^{15}$ |
|---|---|---|---|---|---|---|---|
| 741 | 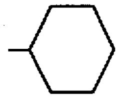 | Me | Me | Me | 1 | H | $CH_2CH_2CH_2NH_2$ |
| 742 | 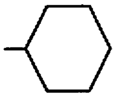 | Me | Me | Me | 1 | H | $CH_2CH_2CH_2CH_2NH_2$ |
| 743 | 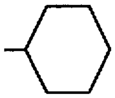 | Me | Me | Me | 1 | H | 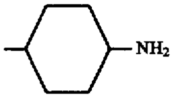 |
| 744 | 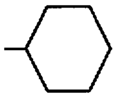 | Me | Me | Me | 1 | H | 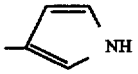 |
| 745 | 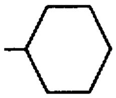 | Me | Me | Me | 1 | H | 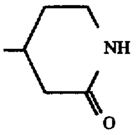 |
| 746 | 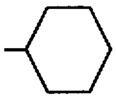 | Me | Me | Me | 1 | H | 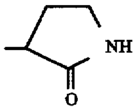 |
| 747 | 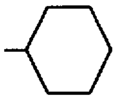 | Me | Me | Me | 1 | H | 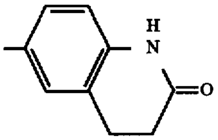 |
| 748 | 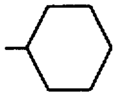 | Me | Me | Me | 1 | H | 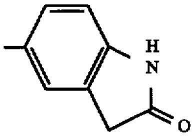 |
| 749 | 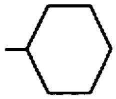 | Me | Me | Me | 1 | H | 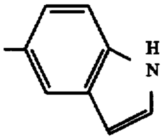 |
| 750 | 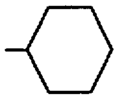 | Me | Me | Me | 1 | H | 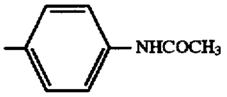 |

TABLE 48
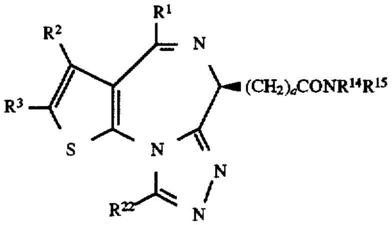
| No. | $R^1$ | $R^2$ | $R^3$ | $R^{22}$ | a | $R^{14}$ | $R^{15}$ |
|---|---|---|---|---|---|---|---|
| 751 | 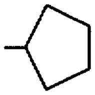 | Me | Me | Me | 1 | H | $CH_2CH_2CH_2NH_2$ |
| 752 | 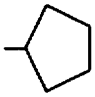 | Me | Me | Me | 1 | H | $CH_2CH_2CH_2CH_2NH_2$ |
| 753 | 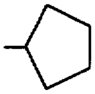 | Me | Me | Me | 1 | H | 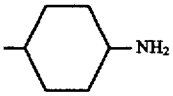 |
| 754 | 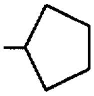 | Me | Me | Me | 1 | H | 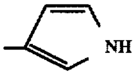 |
| 755 | 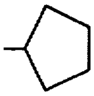 | Me | Me | Me | 1 | H | 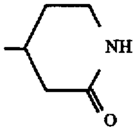 |
| 756 | 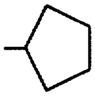 | Me | Me | Me | 1 | H | 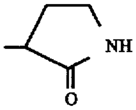 |
| 757 | 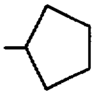 | Me | Me | Me | 1 | H | 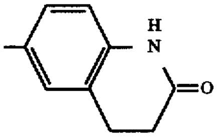 |
| 758 | 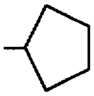 | Me | Me | Me | 1 | H | 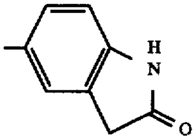 |
| 759 | 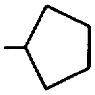 | Me | Me | Me | 1 | H | 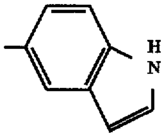 |
| 760 | 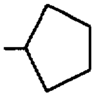 | Me | Me | Me | 1 | H | 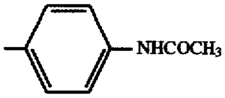 |

TABLE 49
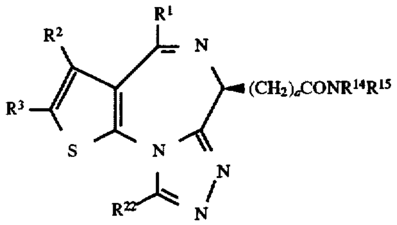
| No. | $R^1$ | $R^2$ | $R^3$ | $R^{22}$ | a | $R^{14}$ | $R^{15}$ |
|---|---|---|---|---|---|---|---|
| 761 | Me | Me | Me | Me | 1 | H | $CH_2CH_2CH_2NH_2$ |
| 762 | Me | Me | Me | Me | 1 | H | $CH_2CH_2CH_2CH_2NH_2$ |
| 763 | Me | Me | Me | Me | 1 | H | 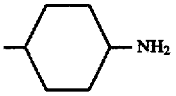 |
| 764 | Me | Me | Me | Me | 1 | H | 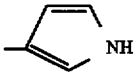 |
| 765 | Me | Me | Me | Me | 1 | H | 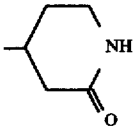 |
| 766 | Me | Me | Me | Me | 1 | H | 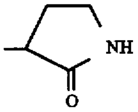 |
| 767 | Me | Me | Me | Me | 1 | H | 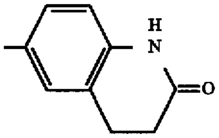 |
| 768 | Me | Me | Me | Me | 1 | H | 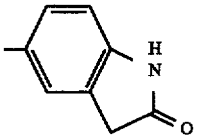 |
| 769 | Me | Me | Me | Me | 1 | H | 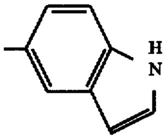 |
| 770 | Me | Me | Me | Me | 1 | H | 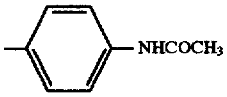 |

TABLE 50
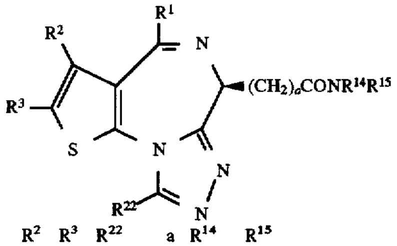
| No. | R1 | R2 | R3 | R22 | a | R14 | R15 |
|---|---|---|---|---|---|---|---|
| 801 | 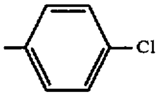 | Me | Me | Me | 1 | H | 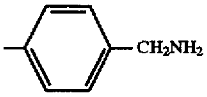 |
| 802 | 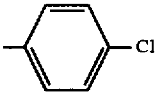 | Me | Me | Me | 1 | H | 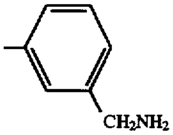 |
| 803 | 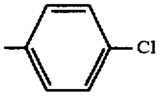 | Me | Me | Me | 1 | H | 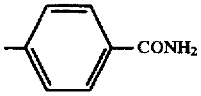 |
| 804 | 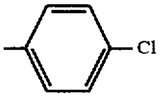 | Me | Me | Me | 1 | H | 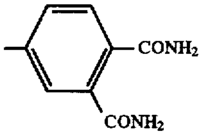 |
| 805 | 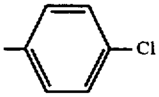 | Me | Me | Me | 1 | H | 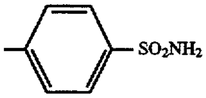 |
| 806 | 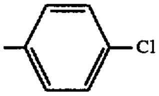 | Me | Me | Me | 1 | H | 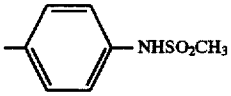 |
| 807 | 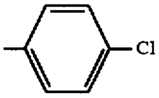 | Me | Me | Me | 1 | H | 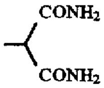 |
| 808 | 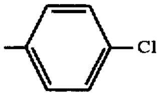 | Me | Me | Me | 1 | H | 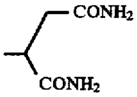 |
| 809 | 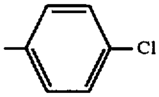 | Me | Me | Me | 1 | H | 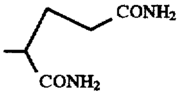 |
| 810 | 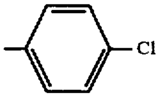 | Me | Me | Me | 1 | H | 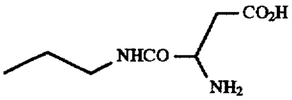 |
| 811 | 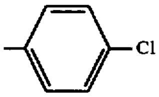 | Me | Me | Me | 1 | H | 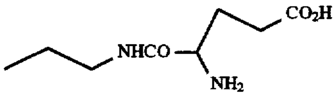 |
| 812 | 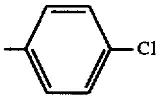 | Me | Me | Me | 1 | H | 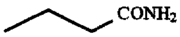 |

TABLE 50-continued
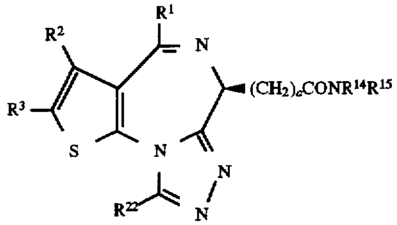
| No. | $R^1$ | $R^2$ | $R^3$ | $R^{22}$ | a | $R^{14}$ | $R^{15}$ |
|---|---|---|---|---|---|---|---|
| 813 | 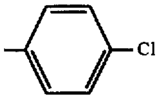 | Me | Me | Me | 1 | H | 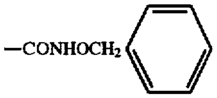 |
| 814 | 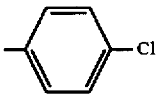 | Me | Me | Me | 1 | H | 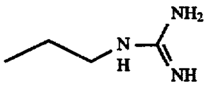 |
| 815 | 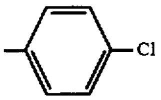 | Me | Me | Me | 1 | H | 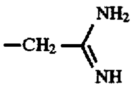 |
TABLE 51
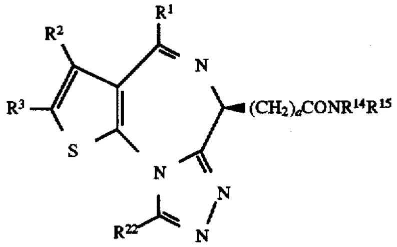
| No. | $R^1$ | $R^2$ | $R^3$ | $R^{22}$ | a | $R^{14}$ | $R^{15}$ |
|---|---|---|---|---|---|---|---|
| 821 | 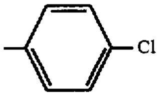 | Me | Me | Me | 2 | H | 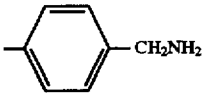 |
| 822 | 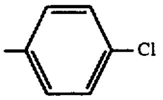 | Me | Me | Me | 2 | H | 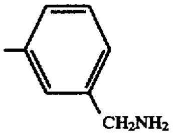 |
| 823 | 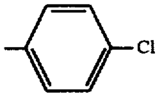 | Me | Me | Me | 2 | H | 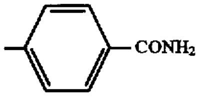 |
| 824 | 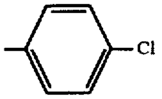 | Me | Me | Me | 2 | H | 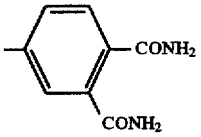 |
| 825 | 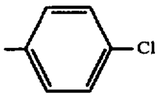 | Me | Me | Me | 2 | H | 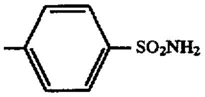 |

TABLE 51-continued
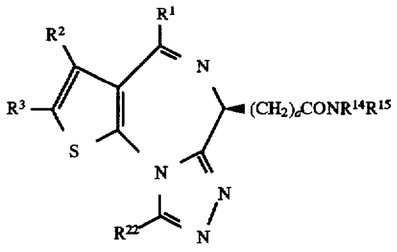
| No. | $R^1$ | $R^2$ | $R^3$ | $R^{22}$ | a | $R^{14}$ | $R^{15}$ |
|---|---|---|---|---|---|---|---|
| 826 | 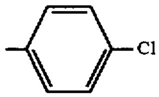 | Me | Me | Me | 2 | H | 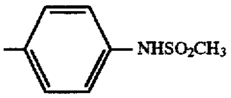 |
| 827 | 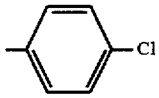 | Me | Me | Me | 2 | H | 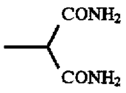 |
| 828 | 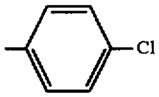 | Me | Me | Me | 2 | H | 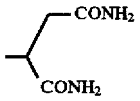 |
| 829 | 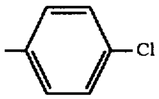 | Me | Me | Me | 2 | H | 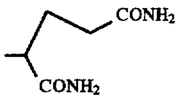 |
| 830 | 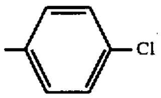 | Me | Me | Me | 2 | H | 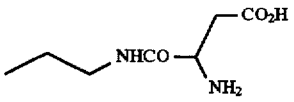 |
| 831 | 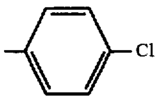 | Me | Me | Me | 2 | H | 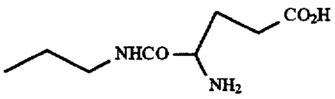 |
| 832 | 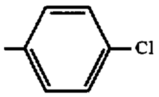 | Me | Me | Me | 2 | H | 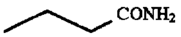 |
| 833 | 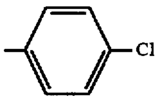 | Me | Me | Me | 2 | H | 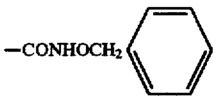 |
| 834 | 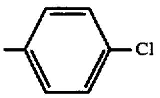 | Me | Me | Me | 2 | H | 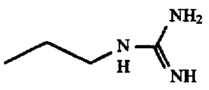 |
| 825 | 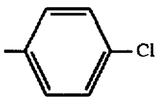 | Me | Me | Me | 2 | H | 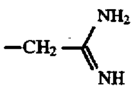 |

TABLE 52
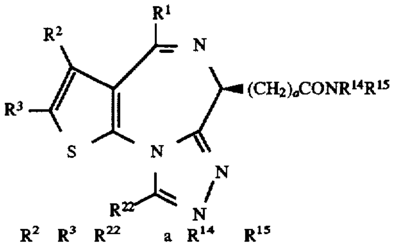
| No. | $R^1$ | $R^2$ | $R^3$ | $R^{22}$ | a | $R^{14}$ | $R^{15}$ |
|---|---|---|---|---|---|---|---|
| 841 | 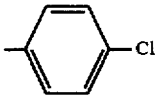 | Me | Me | Me | 3 | H | 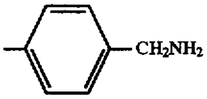 |
| 842 | 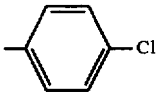 | Me | Me | Me | 3 | H | 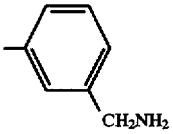 |
| 843 | 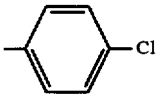 | Me | Me | Me | 3 | H | 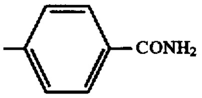 |
| 844 | 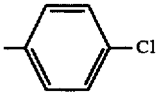 | Me | Me | Me | 3 | H | 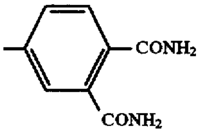 |
| 845 | 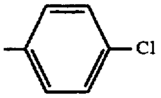 | Me | Me | Me | 3 | H | 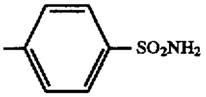 |
| 846 | 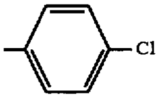 | Me | Me | Me | 3 | H | 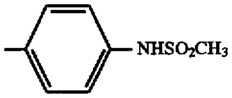 |
| 847 | 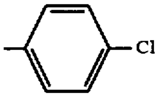 | Me | Me | Me | 3 | H | 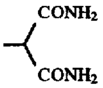 |
| 848 | 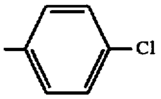 | Me | Me | Me | 3 | H | 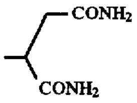 |
| 849 | 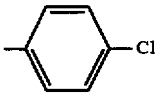 | Me | Me | Me | 3 | H | 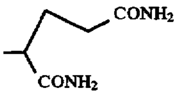 |
| 850 | 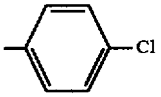 | Me | Me | Me | 3 | H | 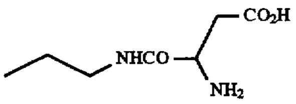 |
| 851 | 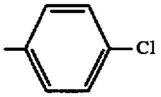 | Me | Me | Me | 3 | H | 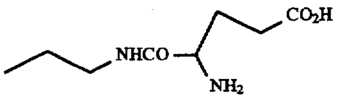 |
| 852 | 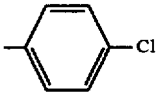 | Me | Me | Me | 3 | H | 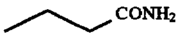 |

TABLE 52-continued
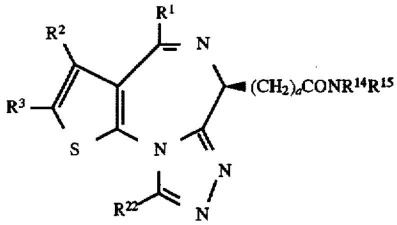
| No. | R¹ | R² | R³ | R²² | a | R¹⁴ | R¹⁵ |
|---|---|---|---|---|---|---|---|
| 853 | 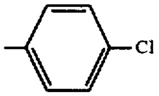 | Me | Me | Me | 3 | H | 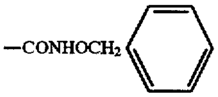 |
| 854 | 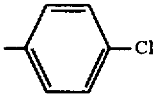 | Me | Me | Me | 3 | H | 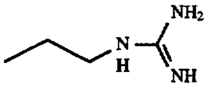 |
| 855 | 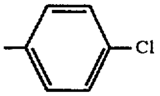 | Me | Me | Me | 3 | H | 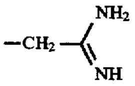 |
TABLE 53
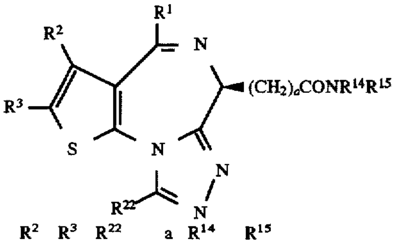
| No. | R¹ | R² | R³ | R²² | a | R¹⁴ | R¹⁵ |
|---|---|---|---|---|---|---|---|
| 861 | 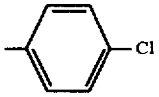 | Me | Me | MeO | 1 | H | 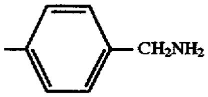 |
| 862 | 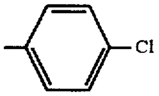 | Me | Me | MeO | 1 | H | 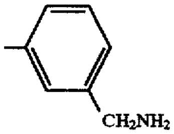 |
| 863 | 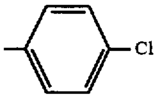 | Me | Me | MeO | 1 | H | 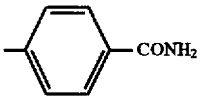 |
| 864 | 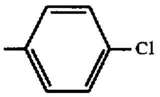 | Me | Me | MeO | 1 | H | 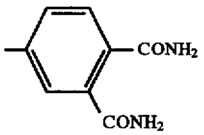 |
| 865 | 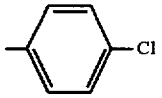 | Me | Me | MeO | 1 | H | 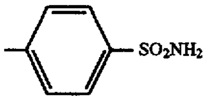 |

TABLE 53-continued
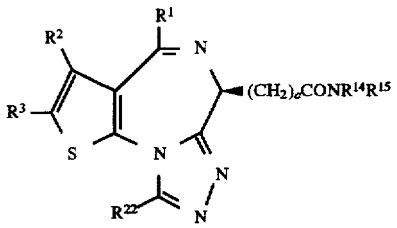
| No. | $R^1$ | $R^2$ | $R^3$ | $R^{22}$ | a | $R^{14}$ | $R^{15}$ |
|---|---|---|---|---|---|---|---|
| 866 | 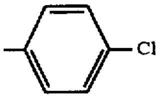 | Me | Me | MeO | 1 | H | 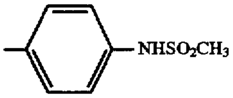 |
| 867 | 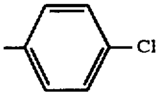 | Me | Me | MeO | 1 | H | 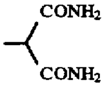 |
| 868 | 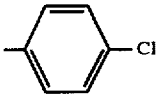 | Me | Me | MeO | 1 | H | 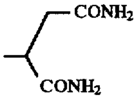 |
| 869 | 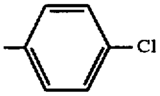 | Me | Me | MeO | 1 | H | 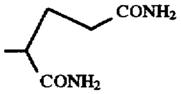 |
| 870 | 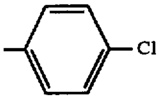 | Me | Me | MeO | 1 | H | 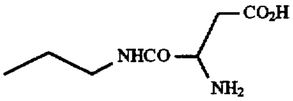 |
| 871 | 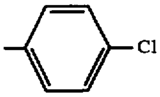 | Me | Me | MeO | 1 | H | 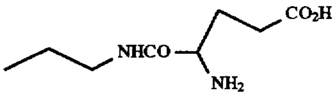 |
| 872 | 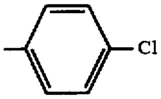 | Me | Me | MeO | 1 | H | 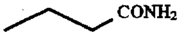 |
| 873 | 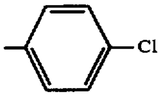 | Me | Me | MeO | 1 | H | 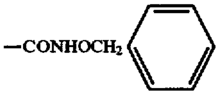 |
| 874 | 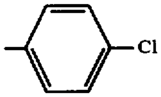 | Me | Me | MeO | 1 | H | 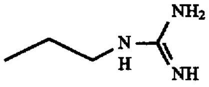 |
| 875 | 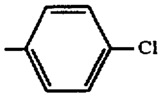 | Me | Me | MeO | 1 | H | 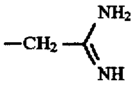 |

TABLE 54
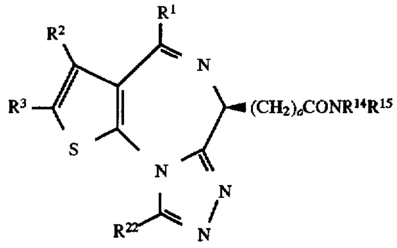
| No. | $R^1$ | $R^2$ | $R^3$ | $R^{22}$ | a | $R^{14}$ | $R^{15}$ |
|---|---|---|---|---|---|---|---|
| 901 | 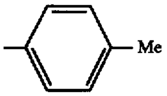 | Me | Me | Me | 1 | H | 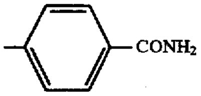 |
| 902 | 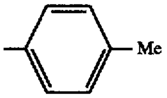 | Me | Me | Me | 1 | H | 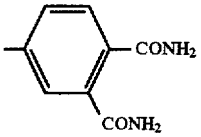 |
| 903 | 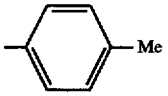 | Me | Me | Me | 1 | H | 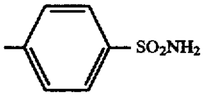 |
| 904 | 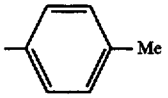 | Me | Me | Me | 1 | H | 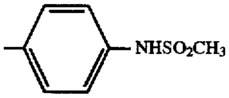 |
| 905 | 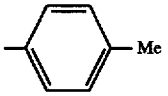 | Me | Me | Me | 1 | H | 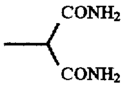 |
| 906 | 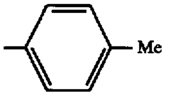 | Me | Me | Me | 1 | H | 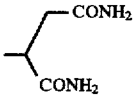 |
| 907 | 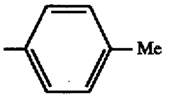 | Me | Me | Me | 1 | H | 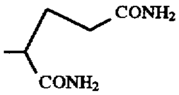 |
| 908 | 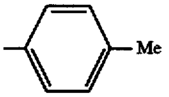 | Me | Me | Me | 1 | H | 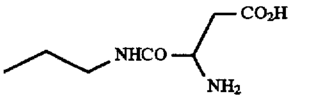 |
| 909 | 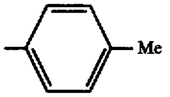 | Me | Me | Me | 1 | H | 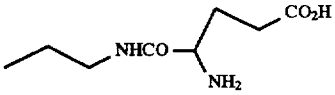 |
| 910 | 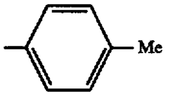 | Me | Me | Me | 1 | H | 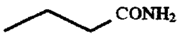 |
| 911 | 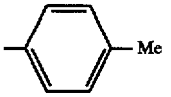 | Me | Me | Me | 1 | H | 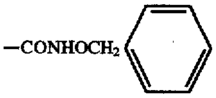 |

TABLE 54-continued
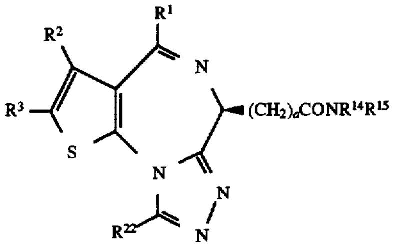
| No. | R¹ | R² | R³ | R²² | a | R¹⁴ | R¹⁵ |
|---|---|---|---|---|---|---|---|
| 912 | 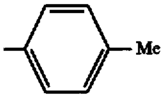 | Me | Me | Me | 1 | H | 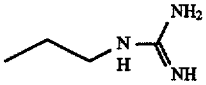 |
| 913 | 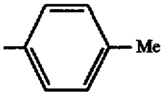 | Me | Me | Me | 1 | H | 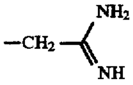 |
| 914 | 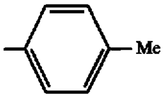 | Me | Me | Me | 1 | H | 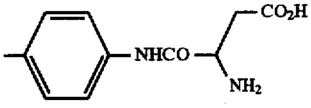 |
| 915 | 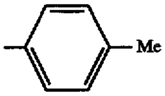 | Me | Me | Me | 1 | H | 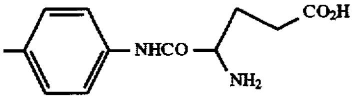 |
| 916 | 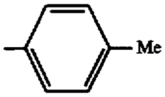 | Me | Me | Me | 1 | H | 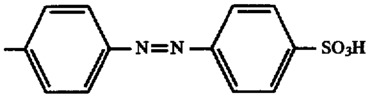 |
| 917 | 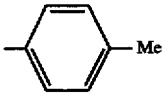 | Me | Me | Me | 1 | H | 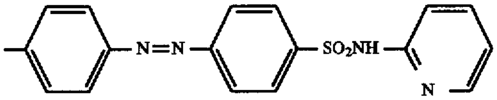 |
| 918 | 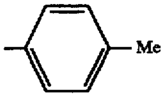 | Me | Me | Me | 1 | H | 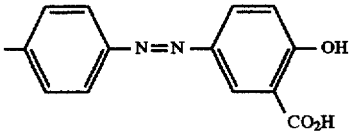 |
TABLE 55
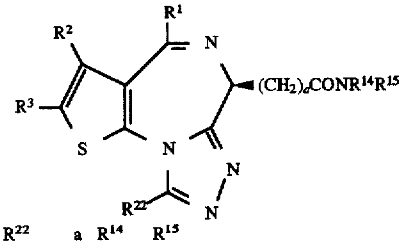
| No. | R¹ | R² | R³ | R²² | a | R¹⁴ | R¹⁵ |
|---|---|---|---|---|---|---|---|
| 921 | 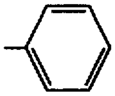 | Me | Me | Me | 1 | H | 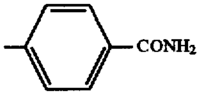 |

TABLE 55-continued
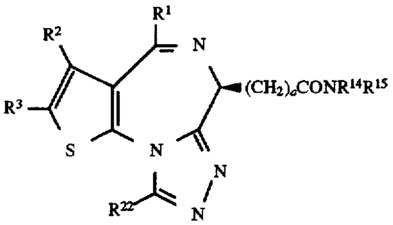
| No. | $R^1$ | $R^2$ | $R^3$ | $R^{22}$ | a | $R^{14}$ | $R^{15}$ |
|---|---|---|---|---|---|---|---|
| 922 | 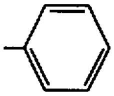 | Me | Me | Me | 1 | H | 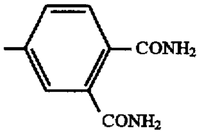 |
| 923 | 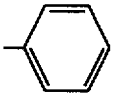 | Me | Me | Me | 1 | H | 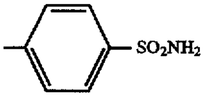 |
| 924 | 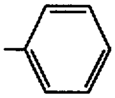 | Me | Me | Me | 1 | H | 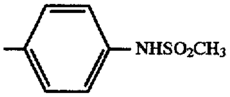 |
| 925 | 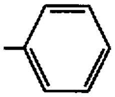 | Me | Me | Me | 1 | H | 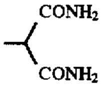 |
| 926 | 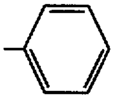 | Me | Me | Me | 1 | H | 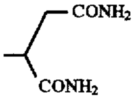 |
| 927 | 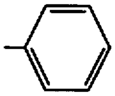 | Me | Me | Me | 1 | H | 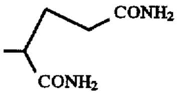 |
| 928 | 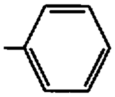 | Me | Me | Me | 1 | H | 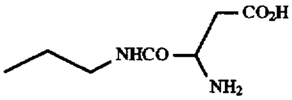 |
| 929 | 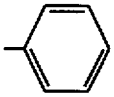 | Me | Me | Me | 1 | H | 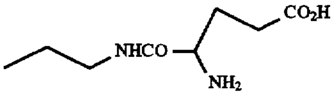 |
| 930 | 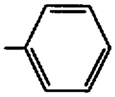 | Me | Me | Me | 1 | H | 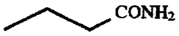 |
| 931 | 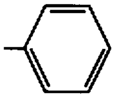 | Me | Me | Me | 1 | H | 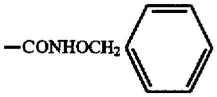 |
| 932 | 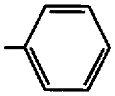 | Me | Me | Me | 1 | H | 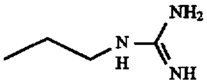 |
| 933 | 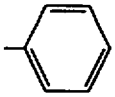 | Me | Me | Me | 1 | H | 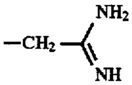 |

TABLE 55-continued
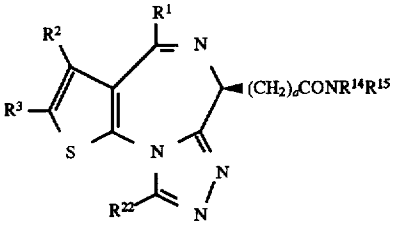
| No. | $R^1$ | $R^2$ | $R^3$ | $R^{22}$ | a | $R^{14}$ | $R^{15}$ |
|---|---|---|---|---|---|---|---|
| 934 | 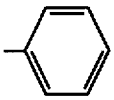 | Me | Me | Me | 1 | H | 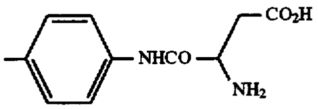 |
| 935 | 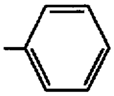 | Me | Me | Me | 1 | H | 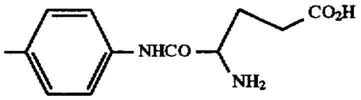 |
| 936 | 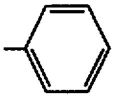 | Me | Me | Me | 1 | H | 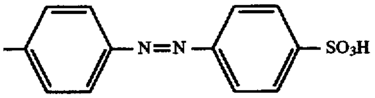 |
| 937 | 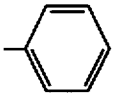 | Me | Me | Me | 1 | H | 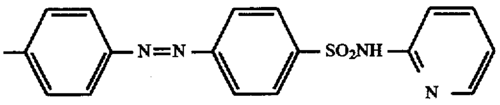 |
| 938 | 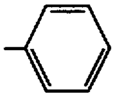 | Me | Me | Me | 1 | H | 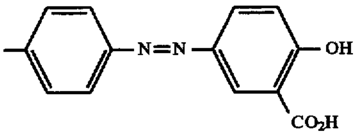 |
TABLE 56
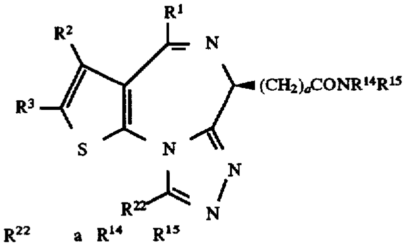
| No. | $R^1$ | $R^2$ | $R^3$ | $R^{22}$ | a | $R^{14}$ | $R^{15}$ |
|---|---|---|---|---|---|---|---|
| 941 | 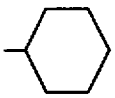 | Me | Me | Me | 1 | H | 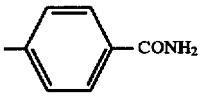 |
| 942 | 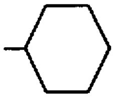 | Me | Me | Me | 1 | H | 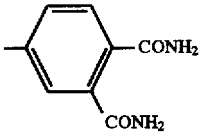 |
| 943 | 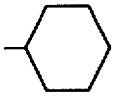 | Me | Me | Me | 1 | H | 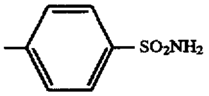 |

TABLE 56-continued
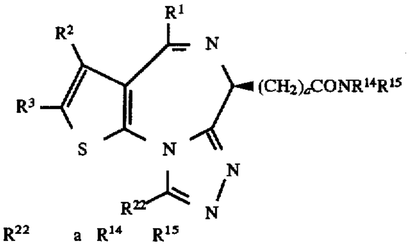
| No. | R¹ | R² | R³ | R²² | a | R¹⁴ | R¹⁵ |
|---|---|---|---|---|---|---|---|
| 944 | 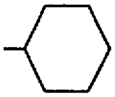 | Me | Me | Me | 1 | H | 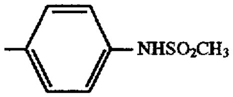 |
| 945 | 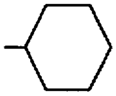 | Me | Me | Me | 1 | H | 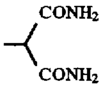 |
| 946 | 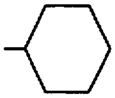 | Me | Me | Me | 1 | H | 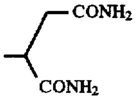 |
| 947 | 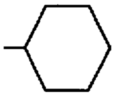 | Me | Me | Me | 1 | H | 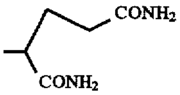 |
| 948 | 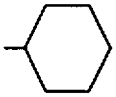 | Me | Me | Me | 1 | H | 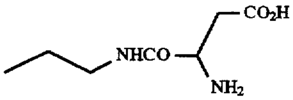 |
| 949 | 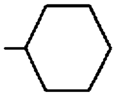 | Me | Me | Me | 1 | H | 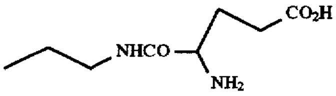 |
| 950 | 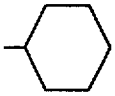 | Me | Me | Me | 1 | H | 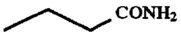 |
| 951 | 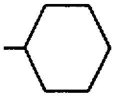 | Me | Me | Me | 1 | H | 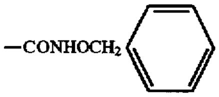 |
| 952 | 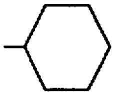 | Me | Me | Me | 1 | H | 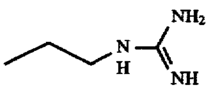 |
| 953 | 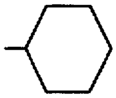 | Me | Me | Me | 1 | H | 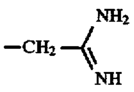 |
| 954 | 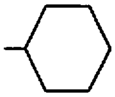 | Me | Me | Me | 1 | H | 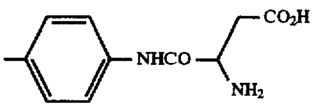 |
| 955 | 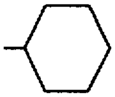 | Me | Me | Me | 1 | H | 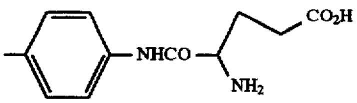 |

TABLE 56-continued
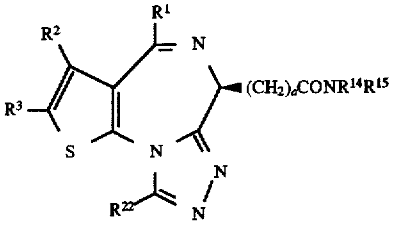
| No. | $R^1$ | $R^2$ | $R^3$ | $R^{22}$ | a | $R^{14}$ | $R^{15}$ |
|---|---|---|---|---|---|---|---|
| 956 | 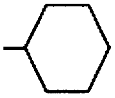 | Me | Me | Me | 1 | H | 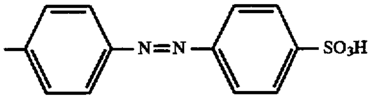 |
| 957 | 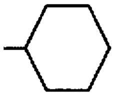 | Me | Me | Me | 1 | H | 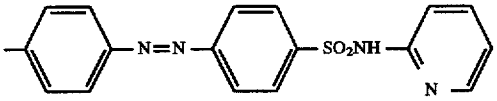 |
| 958 | 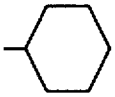 | Me | Me | Me | 1 | H | 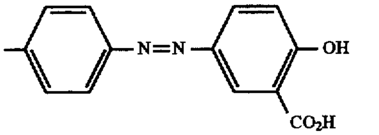 |
TABLE 57
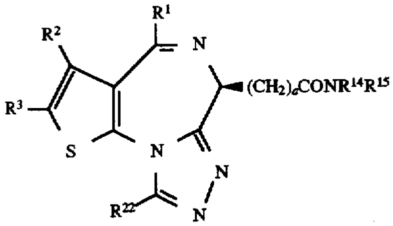
| No. | $R^1$ | $R^2$ | $R^3$ | $R^{22}$ | a | $R^{14}$ | $R^{15}$ |
|---|---|---|---|---|---|---|---|
| 961 | 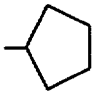 | Me | Me | Me | 1 | H | 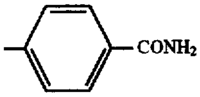 |
| 962 | 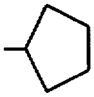 | Me | Me | Me | 1 | H | 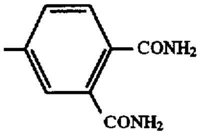 |
| 963 | 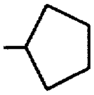 | Me | Me | Me | 1 | H | 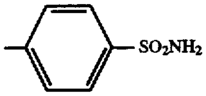 |
| 964 | 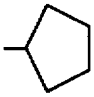 | Me | Me | Me | 1 | H | 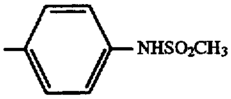 |
| 965 | 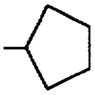 | Me | Me | Me | 1 | H | 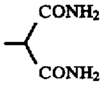 |

TABLE 57-continued
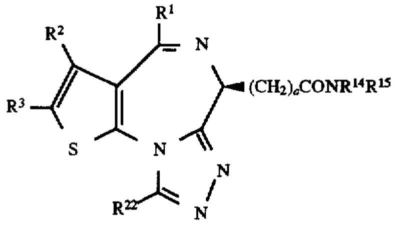
| No. | $R^1$ | $R^2$ | $R^3$ | $R^{22}$ | a | $R^{14}$ | $R^{15}$ |
|---|---|---|---|---|---|---|---|
| 966 | 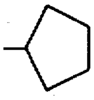 | Me | Me | Me | 1 | H | 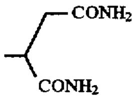 |
| 967 | 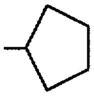 | Me | Me | Me | 1 | H | 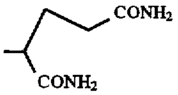 |
| 968 | 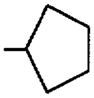 | Me | Me | Me | 1 | H | 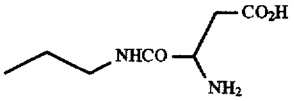 |
| 969 | 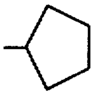 | Me | Me | Me | 1 | H | 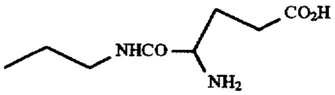 |
| 970 | 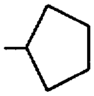 | Me | Me | Me | 1 | H | 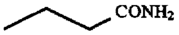 |
| 971 | 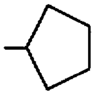 | Me | Me | Me | 1 | H | 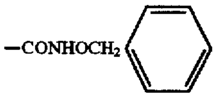 |
| 972 | 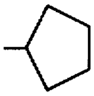 | Me | Me | Me | 1 | H | 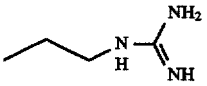 |
| 973 | 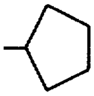 | Me | Me | Me | 1 | H | 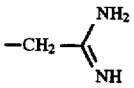 |
| 974 | 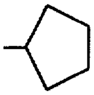 | Me | Me | Me | 1 | H | 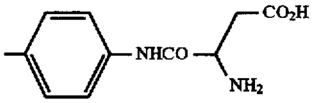 |
| 975 | 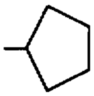 | Me | Me | Me | 1 | H | 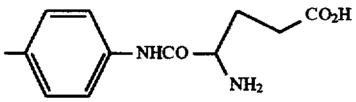 |
| 976 | 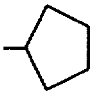 | Me | Me | Me | 1 | H | 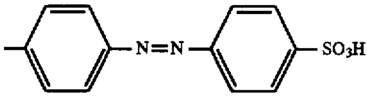 |
| 977 | 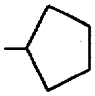 | Me | Me | Me | 1 | H | 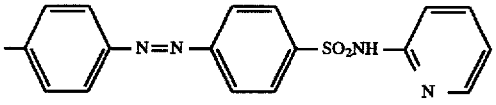 |

TABLE 57-continued
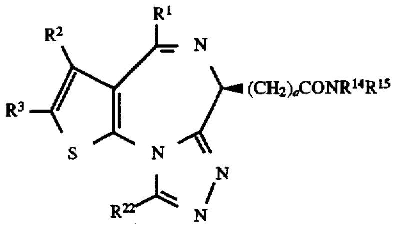
| No. | $R^1$ | $R^2$ | $R^3$ | $R^{22}$ | a | $R^{14}$ | $R^{15}$ |
|---|---|---|---|---|---|---|---|
| 978 | 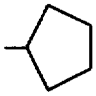 | Me | Me | Me | 1 | H | 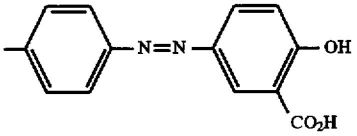 |
TABLE 58
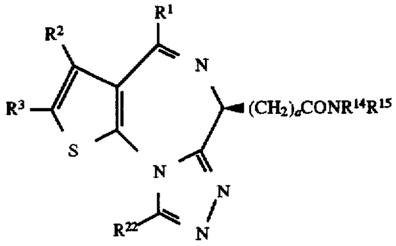
| No. | $R^1$ | $R^2$ | $R^3$ | $R^{22}$ | a | $R^{14}$ | $R^{15}$ |
|---|---|---|---|---|---|---|---|
| 981 | Me | Me | Me | Me | 1 | H | 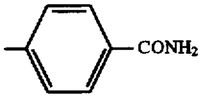 |
| 982 | Me | Me | Me | Me | 1 | H | 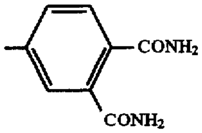 |
| 983 | Me | Me | Me | Me | 1 | H | 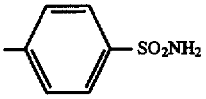 |
| 984 | Me | Me | Me | Me | 1 | H | 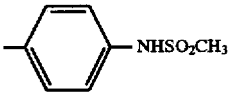 |
| 985 | Me | Me | Me | Me | 1 | H | 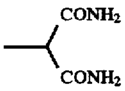 |
| 986 | Me | Me | Me | Me | 1 | H | 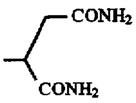 |

TABLE 58-continued
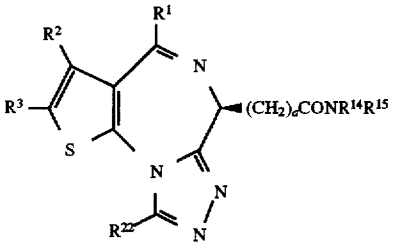
| No. | $R^1$ | $R^2$ | $R^3$ | $R^{22}$ | a | $R^{14}$ | $R^{15}$ |
|---|---|---|---|---|---|---|---|
| 987 | Me | Me | Me | Me | 1 | H | 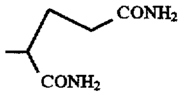 |
| 988 | Me | Me | Me | Me | 1 | H | 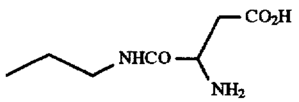 |
| 989 | Me | Me | Me | Me | 1 | H | 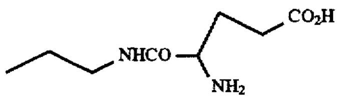 |
| 990 | Me | Me | Me | Me | 1 | H | 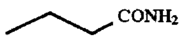 |
| 991 | Me | Me | Me | Me | 1 | H | 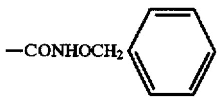 |
| 992 | Me | Me | Me | Me | 1 | H | 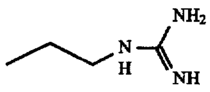 |
| 993 | Me | Me | Me | Me | 1 | H | 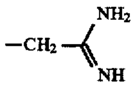 |
| 994 | Me | Me | Me | Me | 1 | H | 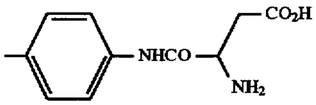 |
| 995 | Me | Me | Me | Me | 1 | H | 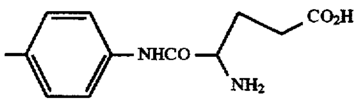 |
| 996 | Me | Me | Me | Me | 1 | H | 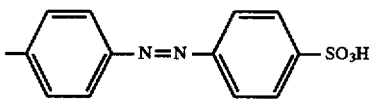 |
| 997 | Me | Me | Me | Me | 1 | H | 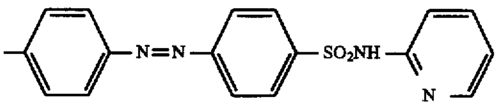 |
| 998 | Me | Me | Me | Me | 1 | H | 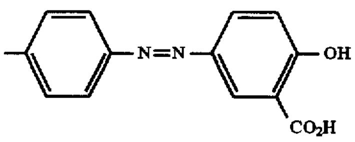 |

TABLE 59
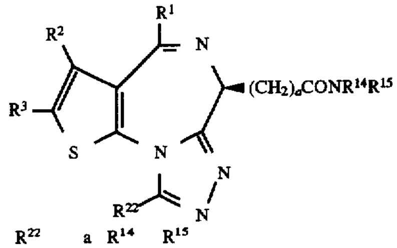
| No. | $R^1$ | $R^2$ | $R^3$ | $R^{22}$ | a | $R^{14}$ | $R^{15}$ |
|---|---|---|---|---|---|---|---|
| 1001 | 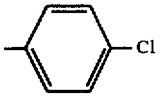 | Me | Me | Me | 1 | H | 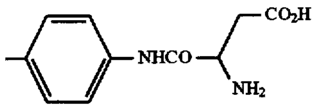 |
| 1002 | 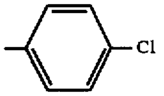 | Me | Me | Me | 1 | H | 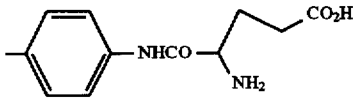 |
| 1003 | 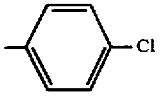 | Me | Me | Me | 1 | H | 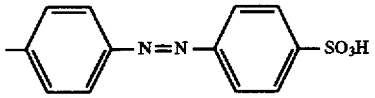 |
| 1004 | 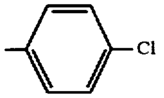 | Me | Me | Me | 1 | H | 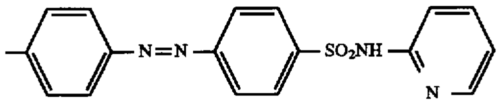 |
| 1005 | 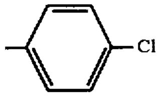 | Me | Me | Me | 1 | H | 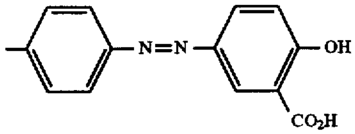 |
TABLE 60
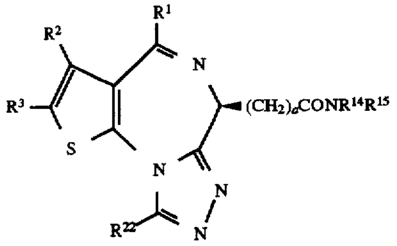
| No. | $R^1$ | $R^2$ | $R^3$ | $R^{22}$ | a | $R^{14}$ | $R^{15}$ |
|---|---|---|---|---|---|---|---|
| 1011 | 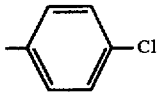 | Me | Me | Me | 2 | H | 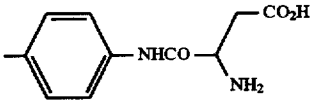 |
| 1012 | 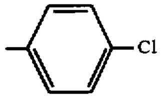 | Me | Me | Me | 2 | H | 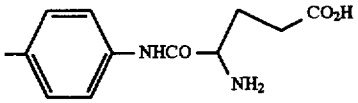 |
| 1013 | 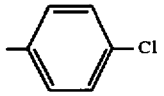 | Me | Me | Me | 2 | H | 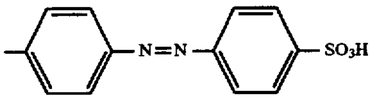 |

TABLE 60-continued
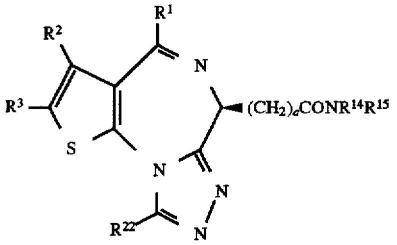
| No. | $R^1$ | $R^2$ | $R^3$ | $R^{22}$ | a | $R^{14}$ | $R^{15}$ |
|---|---|---|---|---|---|---|---|
| 1014 | 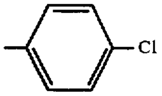 | Me | Me | Me | 2 | H | 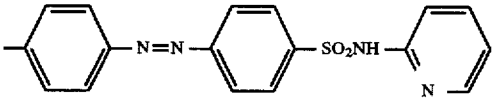 |
| 1015 | 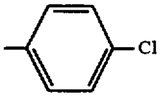 | Me | Me | Me | 2 | H | 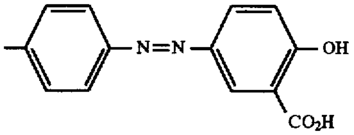 |
TABLE 61
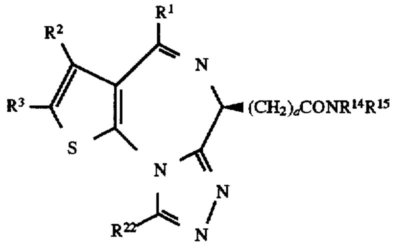
| No. | $R^1$ | $R^2$ | $R^3$ | $R^{22}$ | a | $R^{14}$ | $R^{15}$ |
|---|---|---|---|---|---|---|---|
| 1021 | 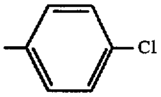 | Me | Me | Me | 3 | H | 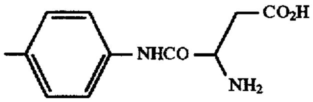 |
| 1022 | 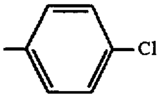 | Me | Me | Me | 3 | H | 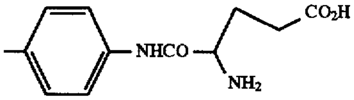 |
| 1023 | 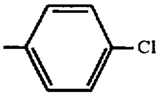 | Me | Me | Me | 3 | H | 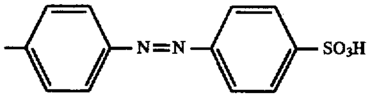 |
| 1024 | 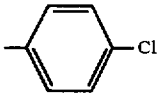 | Me | Me | Me | 3 | H | 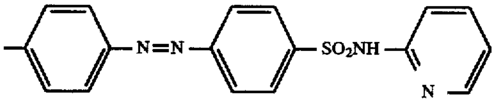 |
| 1025 | 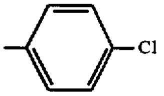 | Me | Me | Me | 3 | H | 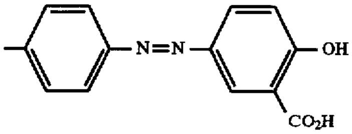 |

TABLE 62
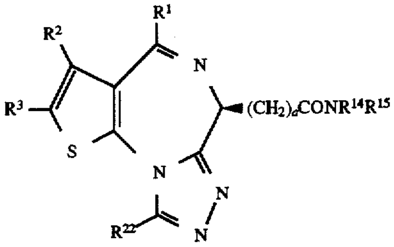
| No. | R¹ | R² | R³ | R²² | a | R¹⁴ | R¹⁵ |
|---|---|---|---|---|---|---|---|
| 1031 | 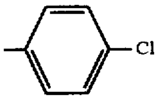 | Me | Me | MeO | 1 | H | 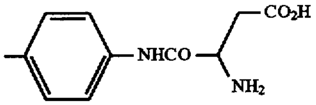 |
| 1032 | 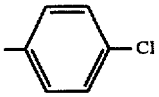 | Me | Me | MeO | 1 | H | 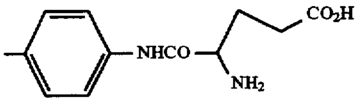 |
| 1033 | 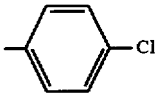 | Me | Me | MeO | 1 | H | 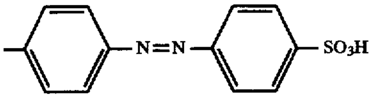 |
| 1034 | 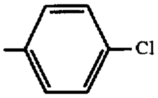 | Me | Me | MeO | 1 | H | 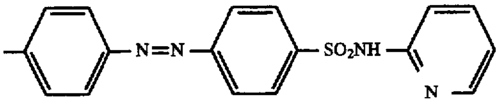 |
| 1035 | 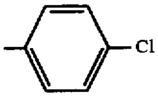 | Me | Me | MeO | 1 | H | 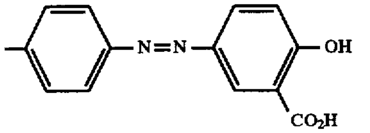 |
TABLE 63
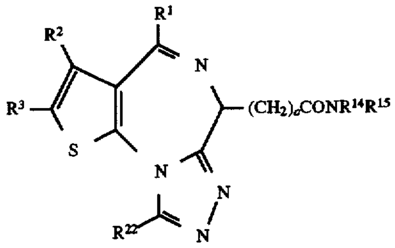
| No. | R¹ | R² | R³ | R²² | a | R¹⁴ | R¹⁵ |
|---|---|---|---|---|---|---|---|
| 1041 | 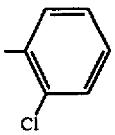 | H | Et | Me | 1 | H | 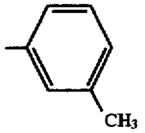 |
| 1042 | 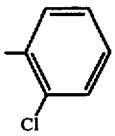 | H | Et | Me | 1 | H | 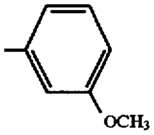 |

TABLE 63-continued
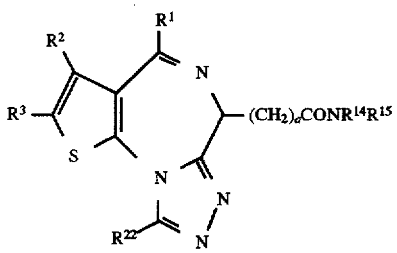
| No. | $R^1$ | $R^2$ | $R^3$ | $R^{22}$ | a | $R^{14}$ | $R^{15}$ |
|---|---|---|---|---|---|---|---|
| 1043 | 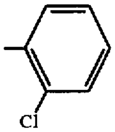 | H | Et | Me | 1 | H | 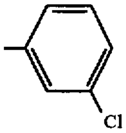 |
| 1044 | 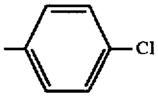 | H | Et | Me | 1 | H | 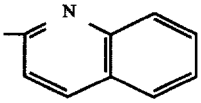 |
| 1045 | 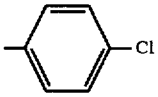 | H | Pr | Me | 1 | H | 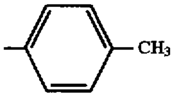 |
| 1046 | 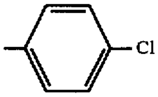 | H | $C_6H_{13}$ | Me | 1 | H | 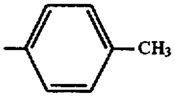 |
| 1047 | 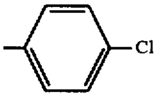 | H | $C_{16}H_{33}$ | Me | 1 | H | 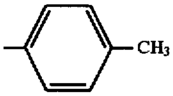 |
| 1048 | 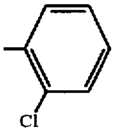 | H | 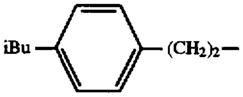 | Me | 1 | H | 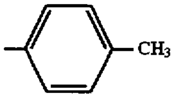 |
| 1049 | 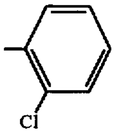 | Me | Me | Me | 1 | H | 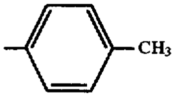 |
| 1050 | 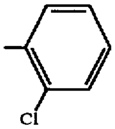 | | $-(CH_2)_4-$ | Me | 1 | H | 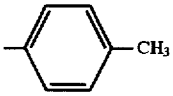 |

TABLE 64

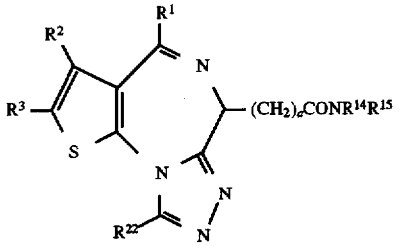

| No. | $R^1$ | $R^2$ | $R^3$ | $R^{22}$ | a | $R^{14}$ | $R^{15}$ |
|---|---|---|---|---|---|---|---|
| 1051 | 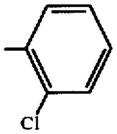 | H | Et | Me | 3 | H | 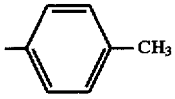 |
| 1052 | 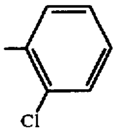 | H | Et | Me | 4 | H | 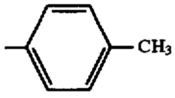 |
| 1053 | 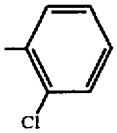 | H | Et | Me | 1 | Bu | 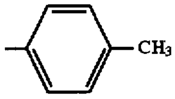 |
| 1054 | 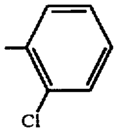 | H | Et | c-$C_6H_{11}$ | 1 | H | 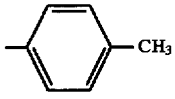 |
| 1055 | 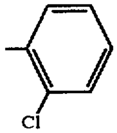 | H | Et | 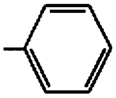 | 1 | H | 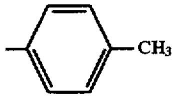 |
| 1056 | 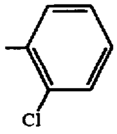 | H | Et | $(CH_2)_2COOH$ | 1 | H | 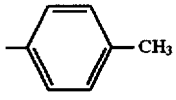 |
| 1057 | 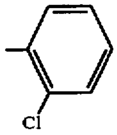 | H | Et | 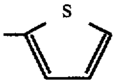 | 1 | H | 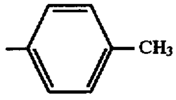 |
| 1058 | 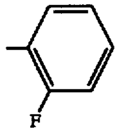 | H | Et | Me | 1 | H | 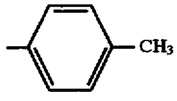 |

Formulation Example

The formulation examples of the pharmaceutical of the present invention are given in the following.

(1) Tablet

The above-mentioned compound (I) (0.5 part), lactose (25 parts), crystalline cellulose (35 parts) and corn starch (3 parts) were thoroughly admixed, and kneaded well with a binder prepared from corn starch (2 parts). The kneaded product was passed through a 16-mesh sieve, dried in an oven at 50° C. and passed through a 24-mesh sieve. The kneaded product thus obtained, corn starch (8 parts), crystalline cellulose (11 parts) and talc (9 parts) were kneaded well, compressed into tablets containing 0.5 mg of the active ingredient per tablet.

(2) 1% Powder

The above-mentioned compound (I) (1 part) and lactose (90 parts) were thoroughly admixed, and kneaded well with a binder prepared from a suitable amount of methylcellulose. The kneaded product was passed through a 16-mesh sieve and dried in an oven at 50° C. The dried granules were forced to pass through a 32-mesh sieve, and admixed well with an appropriate amount of silicon dioxide to give a 1% powder.

What is claimed is:

1. A thienotriazolodiazepine compound of the formula (1)

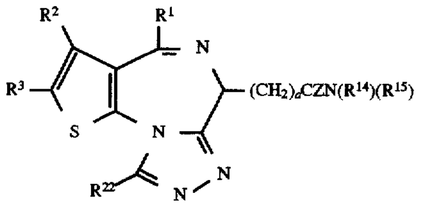
(1)

wherein $R^1$ is a phenyl substituted at the 4-position with a substituent selected from the group consisting of (i) halogen, (ii) alkyl having 1 to 20 carbon atoms, (iii) alkyl having 1 to 6 carbon atoms which is substituted with 1 to 3 substituents selected from alkoxy having 1 to 6 carbon atoms, halogen, hydroxy, sulfo, mercapto, alkylthio, arylthio, aralkylthio, amidino, guanidino, amino, nitro, cyano, carboxy, alkoxycarbonyl, oxo, sulfamoyl, and carbamoyl, (iv) alkoxy having 1 to 6 carbon atoms, (v) hydroxy, (vi) nitro and (vii) cyano, $R^2$ is an alkyl having 1 to 4 carbon atoms;

$R^3$ is an alkyl having 1 to 4 carbon atoms;

a is an integer of 1 to 4;

$R^{14}$ and $R^{15}$ are the same or different and each is (a) a hydrogen, (b) an alkyl having 1 to 20 carbon atoms, (c) an alkenyl having a 2 to 20 carbon atoms, (d) an aryl selected from the group consisting of phenyl, 1-naphthyl and 2-naphthyl, said aryl being optionally substituted with 1 to 3 substituents selected from the group consisting of (i) halogen, (ii) alkyl having 1 to 20 carbon atoms, (iii) alkyl having 1 to 6 carbon atoms which is substituted with 1 to 3 substituents selected from alkoxy having 1 to 6 carbon atoms, halogen, hydroxy, sulfo, mercapto, alkylthio, arylthio, aralkylthio, amidino, guanidino, amino, nitro, cyano, alkoxycarbonyl, oxo, sulfamoyl, and carbamoyl, (iv) alkoxy having 1 to 6 carbon atoms, (v) hydroxy, (vi) mercapto, (vii) alkylthio, (viii) arylthio, (ix) aralkylthio, (x) sulfamoyl which is optionally substituted with, on its nitrogen atom, 1 to 2 substituents selected from alkyl having 1 to 6 carbon atoms, (xi) amino which is optionally substituted with, on its nitrogen atom, 1 to 2 substituents selected from alkyl having 1 to 6 carbon atoms and alkylcarbonyl having 1 to 20 carbon atoms, (xii) nitro, (xiii) cyan, (xiv) sulfo, (xv) alkoxycarbonyl, and (xvi) carbamoyl which is optionally substituted with, on its nitrogen atom, 1 to 2 substituents selected from alkyl having 1 to 6 carbon atoms, or (e) a heterocyclic ring selected from the group consisting of pyridyl, quinolyl, imidazolyl, pyrrolyl, isoquinolyl, triazolyl, 1-pyrazolyl, 2-oxo-1,2,3,4-tetrahydroquinolin-5, 6 or 7-yl, 2-oxoindolin-5 or 6-yl, 2-oxopyrolidine-3 or 4-yl, 2-oxopiperidin-4-yl, 1-benzylpiperidin-4-yl, pyridazinyl, pyrimidinyl, pyrazinyl, indolyl, thienyl, furyl, benzofuranyl, 1H-benzimidazol-2-yl, 2-thiazolyl, 2-benzothiazolyl, 4-methylpiperazin-1-yl, 1 -piperazinyl and 1-perhydropyridazinyl, said heterocyclic group being optionally substituted with 1 to 3 substituents selected from halogen, alkyl, alkoxy having 1 to 6 carbon atoms, hydroxy, mercapto, amino, aminosulfonyl, nitro, cyano, alkoxycarbonyl having 1 to 6 carbon atoms, and carbamoyl;

Z is an oxygen atom; and $R^{22}$ is an alkyl having 1 to 4 carbon atoms, or a pharmaceutically acceptable salt thereof.

2. The compound of claim 1, wherein each symbol denotes the following:

$R^1$ is a 4-chlorophenyl;

$R^2$ is a methyl;

$R^3$ is a methyl;

a is 1;

$R^{14}$ is a hydrogen;

$R^{15}$ is (a) a hydrogen, (b) an alkyl having 1 to 20 carbon atoms, (c) an alkenyl having 2 to 20 carbon atoms, (d) a phenyl which is optionally substituted with 1 to 3 substituents selected from the optionally consisting of (i) halogen, (ii) alkyl having 1 to 20 carbons atoms, (iii) alkyl having 1 to 6 carbon atoms which is substituted with 1 to 3 substituents selected from alkoxy having 1 to 6 carbon atoms, halogen, hydroxy, sulfo, mercapto, alkylthio, arylthio, aralkylthio, amidino, guanidino, amino, nitro, cyano, alkoxycarbonyl, oxo, sulfamoyl, and carbamoyl, (iv) alkoxy having 1 to 6 carbon atoms, (v) hydroxy, (vi) mercapto, (vii) alkylthio, (viii) arylthio, (ix) aralkylthio, (x) sulfamoyl which is optionally substituted with, on its nitrogen atom, 1 to 2 substituents selected from alkyl having 1 to 6 carbon atoms, (xi) amine which is optionally substituted with, on its nitrogen atom, 1 to 2 substituents selected from alkyl having 1 to 6 carbon atoms and alkylcarbonyl having 1 to 6 carbon atoms, (xii) nitro, (xiii) cyano, (xiv) sulfo, (xv) alkoxycarbonyl, and (xvi) carbamoyl which is optionally substituted with, on its nitrogen atom, 1 to 9 substituents selected from alkyl having 1 to 6 carbon atoms, or (e) a heterocyclic ring selected from the group consisting of pyridyl, quinolyl, imidazolyl, pyrrolyl, isoquinolyl, triazolyl, 1-pyrazolyl, 2-oxo-1,2,3,4-tetrahydroquinolin-5, 6 or 7-yl, 2-oxoindolin-5 or 6-yl, 2- oxopyrolidine-3 or 4-yl, 2-oxopiperidin-4-yl, 1-benzylpiperidin-4-yl, pyridazinyl, pyrimidinyl, pyrazinyl, indolyl, thienyl, furyl, benzofuranyl, 1H-benzimidazol-2-yl, 2-thiazolyl, 2-benzothiazolyl, 4-methylpiperazin-1-yl, 1-piperazinyl and 1-perhydropyridazinyl, said heterocyclic group being optionally substituted with 1 to 3 substituents selected from halogen, alkyl having 1 to 6 carbon atoms, alkoxy having 1 to 6 carbon atoms, hydroxy, mercapto, amino, aminosulfonyl, nitro, cyano, alkoxycarbonyl having 1 to 6 carbon atoms and carbamoyl;

Z is an oxygen atom; and $R^{22}$ is a methyl.

3. The compound of claim 1, wherein the compound of the formula (1) is an optically active compound having an S configuration, which is represented by the following formula

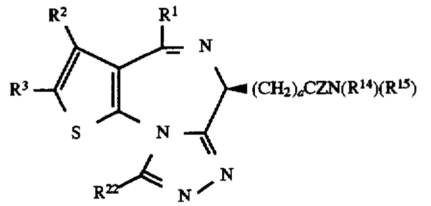

(1a)

wherein all symbols are as defined above.

4. The compound of claim 1, wherein the compound of the formula (1) is a member selected from the group consisting of (±)-N-(3-pyridazinyl)-4-(4-chlorophenyl)-2,3,9-trimethyl-6H-thieno[3,2-f][1,2,4]triazolo[4,3-a][1,4]diazepine-6-acetamide, (±)-N-(4-pyridazinyl)-4-(4-chlorophenyl)-2,3,9-trimethyl-6H-thieno[3,2-f][1,2,4]triazolo[4,3-a][1,4]diazepine-6-acetamide, (±)-N-(3-pyridyl)-4-(4-chlorophenyl)-2,3,9-trimethyl-6H-thieno[3,2-f][1,2,4]triazolo[4,3-a][1,4]diazepine-6-acetamide, (±)-N-methyl-4-(4-chlorophenyl)-2,3,9-trimethyl-6H-thieno[3,2-f][1,2,4]triazolo[4,3-a][1,4]diazepine-6-acetamide, (±)-N-(3-hydroxyphenyl)-4-(4-chlorophenyl)-2,3,9-trimethyl-H-thieno[3,2-f][1,2,4]triazolo[4,3-a][1,4]diazepine-6-acetamide, (S)-N-(4-hydroxyphenyl)-4-(4-chlorophenyl)-2,3,9-trimethyl-6-H-thieno[3,2-f][1,2,4]triazolo[4,3-a][1,4]diazepine-6-acetamide, (±)-N-(4-hydroxyphenyl)-4-(4-chlorophenyl)-2,3,9-trimethyl-H-thieno[3,2-f][1,2,4]triazolo[4,3-a][1,4]diazepine-6-acetamide, (±)-N-(3-aminophenyl)-4-(4-chlorophenyl)-2,3,9-trimethyl-6H-thieno [3,2-f][1,2,4]triazolo[4,3-a][1,4]diazepine-6-acetamide, (±)-N-(4-aminophenyl)-4-(4-chlorophenyl)-2,3,9-trimethyl-6H-thieno [3,2-f][1,2,4]triazolo[4,3-a][1,4]diazepine-6-acetamide, (S)-N-(4-aminophenyl)-4-(4-chlorophenyl)-2,3,9-trimethyl-6H-thieno[3,2-f][1,2,4]triazolo[4,3-a][1,4]diazepine-6-acetamide, (S)-N-methyl-4-(4-chlorophenyl)-2,3,9-trimethyl-6H-thieno[3,2-f][1,2,4]triazolo[4,3-a][1,4]diazepine-6-acetamide, (R)-N-methyl-4-(4-chlorophenyl)-2,3,9-trimethyl-6H-thieno[3,2-f][1,2,4]triazolo[4,3-a][1,4]diazepine-6-acetamide, (±)-N-pyradinyl-4-(4-chlorophenyl)-2,3,9-trimethyl-6H-thieno[3,2-f][1,2,4]triazolo[4,3-a][1,4]diazepine-6-acetamide, (±)-N-(5-pyrimidinyl)-4-(4-chlorophenyl)-2,3,9-trimethyl-6H-thieno[3,2-f][1,2,4]triazolo[4,3-a][1,4]diazepine-6-acetamide, (S)-N-(2-methoxy-3-pyridyl)-4-(4-chlorophenyl)-2,3,9-trimethyl-6H-thieno[3,2-f][1,2,4]triazolo[4,3-a][1,4]diazepine-6-acetamide, (S)-N-(3-pyridyl)-4-(4-chlorophenyl)-2,3,9-trimethyl-6H-thieno[3,2-f][1,2,4]triazolo[4,3-a][1,4]diazepine-6-acetamide, (±)-N-(2-imidazolyl)-4-(4-chlorophenyl)-2,3,9-trimethyl-6H-thieno[3,2-f][1,2,4]triazolo[4,3-a][1,4]diazepine-6-acetamide, and (±)-N-(3-carbamoylphenyl)-4-(4-chlorophenyl)-2,3,9-trimethyl-6H-thieno[3,2-f][1,2,4]triazolo[4,3-a][1,4]diazepine-6-acetamide.

5. The compound of claim 1, wherein the compound of the formula (1) is a member selected from the group consisting of (S)-N-(4-hydroxyphenyl)-4-(4-chlorophenyl)-2,3,9-trimethyl-6H-thieno[3,2-f][1,2,4]triazolo[4,3-a][1,4]diazepine-6-acetamide, (S)-N-(4-aminophenyl)-4-(4-chlorophenyl)-2,3,9-trimethyl-6H-thieno[3,2-f][1,2,4]triazolo[4,3-a][1,4]diazepine-6-acetamide, (S)-N-methyl-4-(4-chlorophenyl)-2,3,9-trimethyl-6H-thieno[3,2-f][1,2,4]triazolo[4,3-a][1,4]diazepine-6-acetamide, (S)-N-(2-methoxy-3-pyridyl)-4-(4-chlorophenyl)-2,3,9-trimethyl-6H-thieno[3,2-f][1,2,4]triazolo[4,3-a][1,4]diazepine-6-acetamide, and (S)-N-(3-pyridyl)-4-(4-chlorophenyl)-2,3,9-trimethyl-6H-thieno[3,2-f][1,2,4]triazolo[4,3-a][1,4]diazepine-6-acetamide.

6. A pharmaceutical composition comprising a therapeutically effective amount of a compound of claim 1 and a pharmaceutically acceptable additive.

7. A method for treating inflammatory diseases caused by cell adhesion, comprising administering an effective amount of a compound of claim 1 to a patient in need of treatment thereof.

8. A method for treating allergic diseases caused by cell adhesion, comprising administering an effective amount of a compound of claim 1 to a patient in need of treatment thereof.

9. The compound of claim 1, wherein $R^1$ is 4-chlorophenyl.

10. The method of claim 7 for treating inflammatory diseases caused by cell adhesion, wherein the compound is (S)-N-(4-hydroxyphenyl)-4-(4-chlorophenyl)-2,3,9-trimethyl-6H-thieno[3,2-f][1,2,4]triazolo[4,3-a][1,4]diazepine-6-acetamide or a pharmaceutically acceptable salt thereof.

11. The method of claim 8 for treating allergic diseases caused by cell adhesion, wherein the compound is (S)-N-(4-hydroxyphenyl)-4-(4-chlorophenyl)-2,3,9-trimethyl-6H-thieno[3,2-f][1,2,4]triazolo[4,3-a][1,4]diazepine-6-acetamide or a pharmaceutically acceptable salt thereof.

12. The compound of claim 1, having the formula

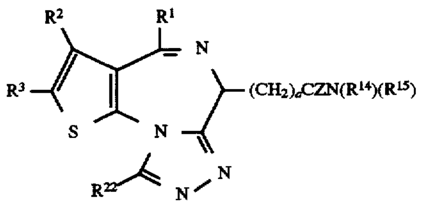

wherein $R^1$ is 4-chlorophenyl, $R^2$ is methyl, $R^3$ is methyl, $R^{22}$ is methyl, and a, Z, $R^{14}$ and $R^{15}$ are as defined in claim 1.

* * * * *